(12) United States Patent
Razavi-Shirazi et al.

(10) Patent No.: US 10,752,528 B2
(45) Date of Patent: *Aug. 25, 2020

(54) WATER TREATMENT PROCESSES USING BIOCATALYSTS

(71) Applicant: Microvi Biotech, Inc., Hayward, CA (US)

(72) Inventors: Fatemeh Razavi-Shirazi, Hayward, CA (US); Mohammad Ali Dorri, Milpitas, CA (US); Farhad Dorri-Nowkoorani, Union City, CA (US); Ameen Razavi, Fremont, CA (US)

(73) Assignee: MICROVI BIOTECH, INC., Hayward, CA (US)

( * ) Notice: Subject to any disclaimer, the term of this patent is extended or adjusted under 35 U.S.C. 154(b) by 441 days.

This patent is subject to a terminal disclaimer.

(21) Appl. No.: 14/407,893

(22) PCT Filed: Jun. 14, 2013

(86) PCT No.: PCT/US2013/046037
§ 371 (c)(1),
(2) Date: Dec. 12, 2014

(87) PCT Pub. No.: WO2013/188858
PCT Pub. Date: Dec. 19, 2013

(65) Prior Publication Data
US 2015/0191715 A1   Jul. 9, 2015

Related U.S. Application Data

(60) Provisional application No. 61/689,921, filed on Jun. 15, 2012, provisional application No. 61/689,922, (Continued)

(51) Int. Cl.
| | | |
|---|---|---|
| *C02F 3/34* | (2006.01) |
| *C02F 3/06* | (2006.01) |
| *C02F 3/08* | (2006.01) |
| *C02F 101/12* | (2006.01) |
| *C02F 101/16* | (2006.01) |
| *C02F 101/20* | (2006.01) |
| *C02F 101/34* | (2006.01) |
| *C02F 3/30* | (2006.01) |
| *C02F 101/10* | (2006.01) |
| *C02F 3/00* | (2006.01) |
| *C12P 5/02* | (2006.01) |
| *C12P 7/46* | (2006.01) |
| *C12P 7/06* | (2006.01) |

(Continued)

(52) U.S. Cl.
CPC ............ *C02F 3/108* (2013.01); *C02F 3/28* (2013.01); *C02F 3/308* (2013.01); *C02F 3/34* (2013.01); *C02F 3/348* (2013.01); *C12N 11/04* (2013.01); *C12N 11/08* (2013.01); *C12N 11/10* (2013.01); *C12P 5/023* (2013.01); *C12P 7/06* (2013.01); *C12P 7/16* (2013.01); *C12P 7/46* (2013.01); *C02F 3/06* (2013.01); *C02F 3/085* (2013.01); *C02F 3/307* (2013.01); *C02F 2003/001* (2013.01); *C02F 2101/105* (2013.01); *C02F 2101/12* (2013.01); *C02F 2101/16* (2013.01); *C02F 2101/163* (2013.01); *C02F 2101/166* (2013.01); *C02F 2101/20* (2013.01); *C02F 2101/34* (2013.01); *C02F 2301/08* (2013.01); *C02F 2301/106* (2013.01); *C02F 2303/02* (2013.01); *C02F 2303/20* (2013.01); *C12P 3/00* (2013.01); *C12P 7/065* (2013.01); *C12P 7/08* (2013.01); *C12P 7/6463* (2013.01); *C12P 39/00* (2013.01); *Y02E 50/10* (2013.01); *Y02E 50/17* (2013.01); *Y02E 50/343* (2013.01); *Y02W 10/12* (2015.05); *Y02W 10/15* (2015.05); *Y02W 10/37* (2015.05)

(58) Field of Classification Search
None
See application file for complete search history.

(56) References Cited

U.S. PATENT DOCUMENTS 3,595,804 A   7/1971 Martin
3,957,678 A   5/1976 Dikhoff et al.
(Continued)

FOREIGN PATENT DOCUMENTS

EP   0446948 A2   9/1991
EP   0465131 A2   1/1992
(Continued)

OTHER PUBLICATIONS

Qureshi, N. et al. 2005. Biofilm reactors for industrial bioconversion processes: employing potential of enhanced reaction rates. Microbial Cell Factories 4(24): 1-21. specif. p. 1.*
Office Action dated Mar. 28, 2017 corresponding to Japanese Patent Application No. 2015-517473, 4 pages.
English translation of Office Action dated Mar. 28, 2017 corresponding to Japanese Patent Application No. 2015-517473, 3 pages.
Written Opinion dated Feb. 20, 2017 corresponding to Singapore Patent Application No. 11201408356V, 5 pages.
Extended European Search Report dated Feb. 22, 2016 corresponding to European Patent Application No. 13804982.0, 7 pages.
(Continued)

Primary Examiner — Thomas J. Visone
Assistant Examiner — Sharon M. Papciak
(74) Attorney, Agent, or Firm — Dentons US LLP

(57) ABSTRACT

The microorganism-containing biocatalysts disclosed have a large population of the microorganisms irreversibly retained in the interior of the biocatalysts. The biocatalysts possess a surprisingly stable population of microorganisms and have an essential absence of debris generation from metabolic activity of the microorganisms. The biocatalysts are composed of highly hydrophilic polymer and have an internal, open, porous structure that promotes community phenotypic changes.

10 Claims, 9 Drawing Sheets

Related U.S. Application Data filed on Jun. 15, 2012, provisional application No. 61/689,923, filed on Jun. 15, 2012, provisional application No. 61/689,924, filed on Jun. 15, 2012, provisional application No. 61/689,925, filed on Jun. 15, 2012, provisional application No. 61/689,929, filed on Jun. 15, 2012, provisional application No. 61/689,930, filed on Jun. 15, 2012, provisional application No. 61/689,932, filed on Jun. 15, 2012, provisional application No. 61/689,933, filed on Jun. 15, 2012, provisional application No. 61/689,935, filed on Jun. 15, 2012, provisional application No. 61/689,939, filed on Jun. 15, 2012, provisional application No. 61/689,940, filed on Jun. 15, 2012, provisional application No. 61/689,943, filed on Jun. 15, 2012, provisional application No. 61/689,945, filed on Jun. 15, 2012, provisional application No. 61/689,953, filed on Jun. 15, 2012, provisional application No. 61/849,725, filed on Feb. 1, 2013, provisional application No. 61/850,631, filed on Feb. 20, 2013, provisional application No. 61/851,467, filed on Mar. 8, 2013, provisional application No. 61/852,451, filed on Mar. 15, 2013.

(51) Int. Cl.

| | | |
|---|---|---|
| C12P 7/16 | (2006.01) | |
| C12P 7/08 | (2006.01) | |
| C12P 7/64 | (2006.01) | |
| C12P 39/00 | (2006.01) | |
| C02F 3/28 | (2006.01) | |
| C12N 11/04 | (2006.01) | |
| C12N 11/10 | (2006.01) | |
| C12N 11/08 | (2020.01) | |
| C02F 3/10 | (2006.01) | |
| C12P 3/00 | (2006.01) | |

(56) References Cited

U.S. PATENT DOCUMENTS

| | | | |
|---|---|---|---|
| 4,148,689 A | 4/1979 | Hino et al. | |
| 4,195,129 A | 3/1980 | Fukui et al. | |
| 4,546,081 A | 10/1985 | Yamada et al. | |
| 4,727,030 A | 2/1988 | Ishimura et al. | |
| 4,743,545 A | 5/1988 | Torobin | |
| 4,791,061 A | 12/1988 | Sumino et al. | |
| 5,071,747 A | 12/1991 | Hough et al. | |
| 5,279,745 A * | 1/1994 | Jeffers | B01J 13/025 210/681 |
| 5,290,693 A | 3/1994 | Chen et al. | |
| 5,424,006 A | 6/1995 | Murayama et al. | |
| 5,439,858 A | 8/1995 | Konishi et al. | |
| 5,486,292 A | 1/1996 | Bair et al. | |
| 5,839,718 A | 11/1998 | Hase et al. | |
| 5,885,483 A | 3/1999 | Hao et al. | |
| 6,107,067 A | 8/2000 | Miller et al. | |
| 6,117,362 A | 9/2000 | Yen et al. | |
| 6,267,911 B1 | 7/2001 | Yen et al. | |
| 6,268,191 B1 | 7/2001 | Prud'homme et al. | |
| 6,610,205 B2 | 8/2003 | Sato et al. | |
| 6,699,696 B2 | 3/2004 | Woods et al. | |
| 6,953,536 B2 | 10/2005 | Yen et al. | |
| 7,384,777 B2 | 6/2008 | Willuweit et al. | |
| 7,682,821 B2 | 3/2010 | Woods et al. | |
| 2002/0185437 A1* | 12/2002 | Haridas | C02F 3/06 210/617 |
| 2006/0063217 A1 | 3/2006 | Omura et al. | |
| 2006/0263869 A1 | 11/2006 | Evans | |
| 2006/0270024 A1* | 11/2006 | Uphoff | C02F 3/06 435/292.1 |
| 2009/0104676 A1 | 4/2009 | Tsai et al. | |
| 2009/0155873 A1 | 6/2009 | Kashiyama et al. | |
| 2009/0215142 A1* | 8/2009 | Tsai | C12M 21/12 435/170 |
| 2009/0215163 A1 | 8/2009 | Tsai et al. | |
| 2010/0089825 A1 | 4/2010 | Canzano et al. | |
| 2010/0105116 A1 | 4/2010 | Datta et al. | |
| 2010/0143993 A1 | 6/2010 | Erdner-Tindall et al. | |
| 2010/0147763 A1 | 6/2010 | Tsou et al. | |
| 2010/0279354 A1 | 11/2010 | De Crecy | |
| 2011/0072714 A1 | 3/2011 | Gaertner | |
| 2011/0165639 A1 | 7/2011 | Ascon et al. | |
| 2011/0185017 A1 | 7/2011 | Rezaiifar | |
| 2011/0297527 A1 | 12/2011 | Fruchey et al. | |
| 2012/0301937 A1 | 11/2012 | Nilsson | |
| 2013/0010539 A1 | 1/2013 | Shim et al. | |
| 2013/0122563 A1 | 5/2013 | Burk et al. | |

FOREIGN PATENT DOCUMENTS

| | | | |
|---|---|---|---|
| EP | 0962492 A1 | 12/1999 | |
| GB | 1556584 A | 11/1979 | |
| JP | 03-83585 A | 4/1991 | |
| JP | 04-211373 A | 8/1992 | |
| JP | 2002-519056 A | 7/2002 | |
| JP | 2011-512795 A | 4/2011 | |
| WO | 00/01803 A1 | 1/2000 | |
| WO | 2007/084477 A1 | 7/2007 | |
| WO | WO-2009089185 A1 * | 7/2009 | C12M 21/02 |

OTHER PUBLICATIONS

Office Action dated Nov. 6, 2015 corresponding to Chinese Patent Application No. 201380043413.1, 9 pages.

English Translation of Office Action dated Nov. 6, 2015 corresponding to Chinese Patent Application No. 201380043413.1, 13 pages.

International Search Report dated Jan. 23, 2014 corresponding to International Patent Application No. PCT/US2013/046037, 5 pages.

Written Opinion of the International Searching Authority dated Jan. 23, 2014 corresponding to International Patent Application No. PCT/US2013/046037, 11 pages.

Kim, Jae-Han, et al., "Simultaneous consumption of pentose and hexose sugars: an optimal microbial phenotype of efficient fermentation of lignocellulosic biomass," Appl Microbiol Biotechnol , 2010, 88, pp. 1077-1085.

International Preliminary Report on Patentability dated Dec. 16, 2014 corresponding to International Patent Application No. PCT/US2013/046037, 12 pages.

Coates, John D. et al., "Ubiquity and Diversity of Dissimilatory (Per)chlorate-Reducing Bacteria", Applied and Environmental Microbiology, vol. 65, No. 12, pp. 5234-5241 (1999).

Ben-Jacob, Eshel et al., "Self-engineering capabilities of bacteria", Journal of the Royal Society Interface, vol. 3, pp. 197-214 (2005).

Cho, HoJung et al., in "Self-Organization in High-Density Bacterial Colonies: Efficient Crowd Control", PLOS Biology, vol. 5, Issue 11, Nov. 2007, pp. 2614-2623.

Davison, Brian H. et al., "Succinic Acid Adsorption from Fermentation Broth and Regeneration", Applied Biochemistry and Biotechnology, vol. 113-116, Mar. 2004, pp. 653-669.

Li, Qiang et al., "Separation of Succinic Acid from Fermentation Broth Using Weak Alkaline Anion Exchange Adsorbents", Ind. Eng. Chem. Res.,vol. 48, pp. 3595-3599 (2009).

Heinzelman , Pete et al., "A family of thermostable fungal cellulases created by structure-guided recombination", PNAS (Proceedings of the National Academy of Sciences of the United States of America), vol. 106, pp. 5610-5615 (Apr. 7, 2009).

Kamiński, Wladyslaw, et al., "Biobutanol—Production and Purification Methods", Ecological Chemistry and Engineering S, vol. 18, No. 1, pp. 31-37 (2011).

Tracy, Bryan P., "Improving Butanol Fermentation to Enter the Advanced Biofuel Market", downloaded from mbio.asm.org, vol. 3, No. 6, Nov./Dec. 2012, 3 pages.

Tuson, Hannah H. et al., "Bacteria-surface Interactions", Soft Matter, vol. 1, No. 608, pp. 4368-4380 (2013).

(56) References Cited

OTHER PUBLICATIONS

Zhou, Lincheng et al., "Recent Patents on Immobilized Microorganisms Technology and Its Engineering Application in Wastewater Treatment", Recent Patents on Engineering, vol. 2, pp. 28-35 (2008).

Nagadomi, Hisashi et al., in "Treatment of Aquarium Water by Denitrifying Photosynthetic Bacteria Using Immobilized Polyvinyl Alcohol Beads", Journal of Bioscience and Bioengineering, vol. 87, No. 2, pp. 189-193 (1999).

Tischer, Wilhelm et al., "Immobilized Enzymes: Methods and Applications", Topics in Current Chemistry, vol. 200. p. 95-126, 1999.

* cited by examiner

BIOREACTOR SEQUENCING

| TIME<br>BIOREACTOR | PERIOD 1 | PERIOD 2 | PERIOD 3 | PERIOD 4 | PERIOD 5 |
|---|---|---|---|---|---|
| A | ANAEROBIC PHA GENERATION MODE | POLISHING AEROBIC PO₄ REMOVAL MODE | PRIMARY AEROBIC PO₄ REMOVAL MODE | PURGE MODE | ANAEROBIC PO₄ RELEASE MODE |
| B | PRIMARY AEROBIC PO₄ REMOVAL MODE | PURGE MODE | ANAEROBIC PO₄ RELEASE MODE | ANAEROBIC PHA GENERATION MODE | POLISHING AEROBIC PO₄ REMOVAL MODE |
| C | POLISHING AEROBIC PO₄ REMOVAL MODE | PRIMARY AEROBIC PO₄ REMOVAL MODE | PURGE MODE | ANAEROBIC PO₄ RELEASE MODE | ANAEROBIC PHA GENERATION MODE |
| D | PURGE MODE | ANAEROBIC PO₄ RELEASE MODE | ANAEROBIC PHA GENERATION MODE | POLISHING AEROBIC PO₄ REMOVAL MODE | PRIMARY AEROBIC PO₄ REMOVAL MODE |
| E | ANAEROBIC PO₄ RELEASE MODE | ANAEROBIC PHA GENERATION MODE | POLISHING AEROBIC PO₄ REMOVAL MODE | PRIMARY AEROBIC PO₄ REMOVAL MODE | PURGE MODE |

FIGURE 8

WATER TREATMENT PROCESSES USING BIOCATALYSTS

CROSS-REFERENCE TO PRIOR APPLICATIONS

This application is a National Stage of PCT/US2013/046037, filed Jun. 14, 2013, and designating the United States (published on Dec. 19, 2013, as WO 2013/188858 A2), which claims priority under 35 U.S.C. § 119 to United States Provisional Patent Application Nos.:

61/689,921, filed on Jun. 15, 2012;
61/689,922, filed on Jun. 15, 2012;
61/689,923, filed on Jun. 15, 2012;
61/689,924, filed on Jun. 15, 2012;
61/689,925, filed on Jun. 15, 2012;
61/689,929, filed on Jun. 15, 2012;
61/689,930, filed on Jun. 15, 2012;
61/689,932, filed on Jun. 15, 2012;
61/689,933, filed on Jun. 15, 2012;
61/689,935, filed on Jun. 15, 2012;
61/689,939, filed on Jun. 15, 2012;
61/689,940, filed on Jun. 15, 2012;
61/689,943, filed on Jun. 15, 2012;
61/689,945, filed on Jun. 15, 2012;
61/689,953, filed on Jun. 15, 2012;
61/849,725, filed on Feb. 1, 2013;
61/850,631, filed on Feb. 20, 2013;
61/851,467, filed on Mar. 8, 2013; and
61/852,451, filed on Mar. 15, 2013,
each hereby expressly incorporated by reference in its entirety and each assigned to the assignee hereof.

STATEMENT REGARDING FEDERALLY SPONSORED RESEARCH OR DEVELOPMENT

The use of biocatalysts for the continuous degradation of 1,4-dioxane in ultralow concentrations in water was first reduced to practice using Government support under Contract 1R43ES022123-01, awarded by the National Institutes of Health. The Government has certain rights thereto.

FIELD OF THE INVENTION

This invention pertains to novel biocatalysts and their use.

BACKGROUND

Metabolic processes have long been proposed for anabolic and catabolic bioconversions. Microorganisms of various types have been proposed for these bioconversions and include bacteria and archaea, both of which are prokaryotes; fungi; and algae. Metabolic processes are used by nature, and some have been adapted to use by man for millennia for anabolic and catabolic bioconversions ranging from culturing yogurt and fermentation of sugars to produce alcohol to treatment of water to remove contaminants. Metabolic processes offer the potential for low energy consumption, high efficiency bioconversions in relatively inexpensive processing equipment and thus may be and are often viable alternatives to chemical synthesis and degradation methods. Often anabolic processes can use raw materials that are preferred from a renewable or environmental standpoint but are not desirable for chemical synthesis, e.g., the conversion of carbon dioxide to biofuels and other bioproducts. Catabolic bioconversions can degrade substrates and have long been used for waste water treatment. Considerable interests exist in improving metabolic processes for industrial use and expanding the variety of metabolic process alternatives to chemical syntheses and degradations.

Numerous types of process techniques have been proposed for anabolic and catabolic bioconversions. These processes include the use of suspended microorganisms, i.e., planktonic processes. Also, process techniques have been disclosed where the microorganisms are located on or within a solid support.

Workers are faced with various challenges in improving metabolic processes and in providing metabolic processes that are sufficiently economically viable to be of commercial interest. Some problems may be inherent with the feedstock itself including the presence of toxins, phages, and adventitious competitive microorganisms. Other problems may arise from the microorganism to be used for the bioconversion such as low metabolic conversion rate, low population growth rate, automutation, significant consumption of substrate to support population growth, the need for inducers, co-metabolites, promoters and performance enhancing additives, and the lack of a microorganism that has the sought metabolic conversion. And yet further problems may arise from the process used for the bioconversion such as costs in recovering bioproducts from an aqueous fermentation broth. Especially with supported microorganisms, problems can arise from instability of the biofilms, including their physical degradation; overgrowth of the population of microorganisms causing suffocation; sloughing off of the microorganisms from the support; and susceptibility to competitive microorganisms. Additionally, metabolic processes are characterized as generating solid debris from dead or lysed cells, and the debris needs to be accommodated in the process to remove these solids. In some instances, the debris have value as feed supplements such as distillers grains from the manufacturing of ethanol, but in other metabolic processes such as for the treatment of municipal waste water, costs may have to be incurred to dispose of the debris in an environmentally acceptable manner. Genetic engineering, which has been proposed to overcome one or more of these problems, can itself be problematic.

Microorganisms, including but not limited to, bacteria, archaea, fungi and algae, are capable of becoming attached or adhered to a surface. Studies have been conducted pertaining to the effect of a change from planktonic growth to growth of microorganisms on surfaces, including the formation of biofilms on surfaces. A number of workers have investigated preventing or degrading biofilms in an animal or human body to enhance the efficacy of antibiotic treatments to cure the animal or human body.

Tuson, et al., in "Bacteria-surface Interactions", Soft Matter, Vol. 1, issue 608 (2013) citable as DOI: 10.1039/c3sm27705d, provide a review of work in the field of bacterial-surface interactions. The authors describe the processes involved in attaching a microorganism to a surface and recite that attachment to surfaces causes phenotypic switches in the cells and that the surface can provide benefits to the attached cells. The authors recite that organic matter can concentrate at horizontal surfaces stimulating growth of bacteria associated with the surface, and increasing substrate surface area provides more area on which nutrients can absorb, enabling cells to grow at nutrient concentrations that would normally be too low to support growth. The authors further state that in addition to surface attachment facilitating nutrient capture, some bacteria obtain necessary metabolites and co-factors directly from the surfaces to which they adhere.

Some of the observations reported in this article include that nucleating cell growth into communities on surfaces protect cells from predation and other environmental threats and facilitate the conservation of the genotype. The authors recite that where the microorganisms form biofilms, resistance to antibiotic treatment has been observed. This resistance has been attributed to one or more of the barrier function of the biofilm matrix; the presence of dormant persister cells and highly resistant colony variants, and upregulation of several biofilm-specific antibiotic resistance genes. One group of workers have postulated that some adhering cells not associated with biofilms have resistance to antibiotics due to primary mechanisms of reducing the net negative charge on bacterial cells and enhancing the stability of the membrane. Tuson, et al., points to a conclusion drawn in one article that the attachment of bacteria to surfaces alters their metabolic state and reduces antibiotic susceptibility, which is a common feature of bacteria during the stationary phase of cell growth.

In respect of cell activities pertaining to association of bacteria with surfaces, the authors discuss that surface sensing is a precursor to swarming which is an important adaptive behavior in which contact between cells and surfaces programs morphological changes that facilitate cooperative behavior, rapid community growth, and migration of communities. The cells in bacterial communities such as swarms or biofilms interact with each other in several different ways. Bacteria are able to communicate through the use of small molecule chemical messengers in a process referred to as quorum sensing.

"The dense packing of cells in bacterial communities facilitates and increase in the concentration of small molecules that transfer information between cells and trigger physiological changes. The shape of chemical gradients in close proximity to surfaces enhances the exchange of chemical information within biofilms and communities attached to surfaces."

Cho, et al., in "Self-Organization in High-Density Bacterial Colonies: Efficient Crowd Control", PLOS Biology, Vol. 5, Issue 11, November 2007, pages 2614 to 2623, relate their findings that *E. coli* in microchambers communicate to provide colony growth towards an escape from the confines of the microchambers without a potentially "stampede"-like blockage of the exit and to provide channels to facilitate nutrient transport into the colony.

Tuson, et al., further describe the steps for the formation of an attachment of a cell to a surface. The initial attachment is reversible and involves hydrodynamic and electrostatic interactions and the second step of the attachment is irreversible and involves van der Waals interactions between the hydrophobic region of the outer cell wall and the surface. Irreversible attachment is facilitated by the production of extracellular polymeric substance.

"Thermodynamics plays a central role in regulating the binding of bacteria to surfaces. Cells attach preferentially to hydrophilic materials (i.e., materials with a large surface energy) when the surface energy of the bacterium is larger than surface energy of the liquid in which they are suspended. The surface energy of bacteria is typically smaller than the surface energy of liquids in which the cells are suspended, and this mismatch causes cells to attach preferentially to hydrophobic materials (i.e., materials with lower surface energies). Bacteria are able to attach to a wide variety of different materials, including glass, aluminum, stainless steel, various organic polymers, and for needed materials such as Teflon™."

Tuson, et al., report that surface sensing triggers a variety of cellular changes. Many of the changes are morphological and facilitate attachment to surfaces. They state:

"Interestingly, the physical properties of surfaces may influence cell morphology and community structure." . . . "Cells adhere uniformly to hydrophobic surfaces, form microcolonies, and grow into tightly packed multi-layer biofilms. Fewer cells attach to hydrophilic surfaces, and changes in cell division lead to the formation of chains of cells that are >100 µm long. These chains become loosely entangled to form relatively unstructured and less densely packed biofilms."

Tuson, et al., in their concluding remarks state:

"Our understanding of the interaction of bacteria was surfaces is remarkably incomplete. This topic seems ideally suited for collaborations between microbiologist and materials scientists, chemists, and engineers as it is poised to benefit from multidisciplinary approaches that are formulated to penetrate into a range of areas, including: (1) identifying the properties of surfaces that are sensed by bacteria; (2) elucidating the molecular mechanisms bacteria used to send surfaces and their biochemical responses; and (3) determining how to modulate surface properties to provoke a desired cellular response, including changes in morphology, alterations in bioenergetics, or cell death."

Many proposals exist for using a solid carrier or support for microorganisms to effect a plethora of anabolic and catabolic bioconversions; however, despite the potential process advantages provided by using a solid, commercial success has been limited to a relatively few applications. Proposals have been proffered for the microorganisms to be supported on the surface of a carrier or in pores of a carrier and for the microorganisms to be located within the carrier. See, for instance, Zhou, et al., "Recent Patents on Immobilized Microorganisms Technology and Its Engineering Application in Wastewater Treatment, Recent Patents on Engineering, 2008, 2, 28-35.

As a general rule, solid debris are generated as a result of the biological activity, e.g., from the instability of the biofilm formed on the carrier and from the death and deterioration of cell mass. For instance, Sato, et al., in U.S. Pat. No. 6,610,205, disclose processes for nitrifying and denitrifying organic waste water using a thermoplastic microbe carrier. The patentees assert that a single carrier can affect both bioconversions requiring aerobic and anaerobic conditions. The carrier, once formed, is contacted with activated sludge containing microorganisms. The patentees state that the nitrifying bacteria are "thickly grown" on the surface of the carrier and the denitrifying bacteria are "adsorbed onto the carrier and thereby are firmly immobilized thereon". Their FIG. 1 depicts an apparatus using the carrier and includes settling tank 9 to remove sludge. Accordingly, such processes appear to require a means to remove debris from the support or carrier.

Several workers have formed an aqueous mixture of microorganisms and polymer as a solution, dispersion or emulsion. Some workers spray dried the mixture and others proposed crosslinking to obtain a solid structure containing microorganisms within the interior of the solid structure. The following discussion is provided as an illustration of proposals to form solid structures from an aqueous medium also containing microorganisms.

Hino, et al., in U.S. Pat. No. 4,148,689 disclose the use of microorganisms in a hydrophilic complex gel by dispersing microorganisms in a certain homogeneous sol and then gelling the mixture and treating it chemically or by drying to obtain a xerogel. The xerogel is said to possess desired strength and is composed of gelled water soluble polymer, such as natural polymers, polyvinyl alcohol, polyethylene glycol and polyethylene imine, and silica. The xerogels used in the examples appear to provide bioconversion, but at lesser activities than suspended cell fermentations. Most of the examples appear to demonstrate bioactivity over a short duration, e.g., less than 30 hours. Those examples that appear to report activity over longer durations also indicate deactivation over time. Indeed, the patentees contemplate that an advantage of their xerogel is that the polymer can be recovered and recycled upon deactivation. See column 9, lines 66 et seq.

Fukui, et al., in U.S. Pat. No. 4,195,129, disclose mixing microbial cells with photo-curable resin and irradiating the mixture to provide a cured product containing immobilized cells. The product, according to the examples, does not have the bioactivity of a free cell suspension. The patentees do not provide any data regarding the performance of the immobilized cells over a long duration.

Yamada, et al., in U.S. Pat. No. 4,546,081 disclose a process for continuous fermentation with yeast to produce alcohol. The yeast is immobilized in a thin film which is then positioned within a vessel for the fermentation. The patentees recite a number of different techniques for making the film containing the yeast. Although a process in which a mixture of yeast and polyvinyl alcohol is gelled by radiation and formed into the desired shape, no performance differences among the films prepared by the various techniques are specifically recited in the patent.

Ishimura, et al., in U.S. Pat. No. 4,727,030, have as an objective obtaining a molded, porous article containing microbial cells. They disclose a process for immobilizing enzymes or cells wherein the enzymes or cells are mixed with polyvinyl alcohol and activated carbon, and then the mixture is partially dried then molded and further dehydrated under specified conditions. The porous gel is said to have little expansion upon hydration.

In the 1990's a process was developed in Japan called the Pegasus Process, see, for instance, Stowa Pagasus/Pegazur/Bio-tube Process Sheets, Jun. 13, 2006, that uses organic gel pellets composed of a mixture of polyethylene glycol and nitrifying activated sludge. See also, U.S. Pat. No. 4,791,061 which is in the same patent family as KR9312103 referenced in this document. The pellets are said to have a diameter of 3 millimeters and a polyethylene glycol fraction of 15 percent and a microorganism fraction of 2 percent with a biofilm thickness of about 60 micrometers. The patent discloses preparing the pellets from a mixture containing an activated sludge and prepolymer and dropping the mixture into a water solution of polyvalent metal ion and persulfate to form particles with immobilized microorganisms. The process is asserted to reduce the loss in activity of the microorganisms in forming the pellets.

Chen, et al., in U.S. Pat. No. 5,290,693 immobilizing microorganisms or enzymes on beads of polyvinyl alcohol. They form a mixture of polyvinyl alcohol and microorganisms and then conduct a two stage gelation and hardening step using boric acid and then phosphoric acid or phosphate. The patentees state that their process provides strong beads without being detrimental to the microorganisms or enzymes immobilized. The examples are instructive. Example 1, for instance, pertains to making and using beads for denitrification of water containing 100 ppm potassium nitrate. They state at column 5, lines 7 to 11:

"On the seventh day, denitrification rate of the immobilized microorganisms reached 0.65 mg $NO_3^1$-N/g gel/h (sic), which remained unchanged until the $30^{th}$ day. The biochemical vitality of microorganisms remained stable."

The solution used to make the beads contained about 25 g/L of denitrifying sludge microorganisms. This example appears to indicate that 7 days of growth of the population of microorganisms were required to achieve the activity, and that after 30 days, the stable activity was lost. The comparative control reported in this example, which used boric acid only to gel and harden the PVA, provided a denitrification rate of 0.55 mg $NO_3^-$—N/g gel/h and became unstable after 15 days. Examples 2 and 3 report data for continuous operations that extended for 10 and 20 days respectively. Example 4 pertains to the production of ethanol using *Sacchramyces cerevisa* (about 15 g/L in the mixture with the polyvinyl alcohol) and only 8 hours of use were reported with the beads containing the immobilized microorganisms being slightly inferior in ethanol production than unsupported yeast.

Nagadomi, et al., in "Treatment of Aquarium Water by Denitrifying Photosynthetic Bacteria Using Immobilized Polyvinyl Alcohol Beads", Journal of Bioscience and Bioengineering, 87, 2, 189-193 (1999), confirm the observations of Chen, et al. They found that boric acid is deleterious to microorganisms. They also observed the growth of the population of microorganisms immobilized in alginate beads and in polyvinyl alcohol beads. The data reported by the authors did not extend much over 15 days of operation.

Willuwait, et al., in U.S. Pat. No. 7,384,777 B2, immobilize bacteria in polymeric matrices. The matrices are used for the controlled release of the microorganisms. As explained at column 3, lines 63 to 67:

"By means of the cleaning process, the microorganisms multiply until the holding capacity of the capsules/spheres or the gel has been reached and the wall bursts, i.e., the microorganisms are released."

It is not surprising, therefore, that the large bulk of activities directed towards improving metabolic processes have focused on changing the genotype of the microorganism, e.g., through genetic engineering. Genotypic alterations often come at significant expense and require substantial time to obtain the sought performance from a microorganism. Typically most genetically engineered microorganisms lack robustness, e.g., are slow growing and are competitively disadvantaged against invasive microorganisms and are subject to losing plasmids during scale up for quantities sufficient to fill commercial-scale bioreactors and during the bioconversion process itself. Additionally, genetically engineered microorganisms may have to be carefully contained so as not to escape to the environment, and disposal of debris from metabolic processes using genetically engineered microorganisms may be treated as hazardous waste.

SUMMARY

The microorganism-containing biocatalysts of this invention have a large population of the microorganisms irreversibly retained in the interior of the biocatalysts, and the biocatalysts possess a surprisingly stable population of microorganisms, and hence stable bioactivity, and an essential absence of debris generation from metabolic activity of the microorganisms, and the biocatalysts can exhibit these phenomenon over extended periods of time. These phenomena are contrary to conventional expectations are that microorganisms either escape from physically restricted regions or that the physically restricted region becomes clogged or over populated leading to loss of metabolic activity and ultimate death of the population of microorganisms.

The microorganisms in the biocatalysts of this invention exhibit phenotypic alterations that, in combination with an internal, cavity-containing structure of the biocatalyst, provide highly advantageous biocatalysts including, but not limited to, a metabolic shift from growth of the microorganisms and their population to bioconversion activity (anabolic or catabolic); enhanced tolerance to toxins; enhanced ability to enter a substantial state of stasis even for extended periods of time; and enhanced ability to efficiently bioconvert substrate. These phenotypic changes significantly add to the fact that the microorganisms effecting the bioconversion are retained in the interior of the biocatalyst to provide advantageous metabolic processes, especially metabolic processes where the biocatalysts of this invention provide desirable bioconversion activity over extended periods of time, preferably at least about 3, preferably at least about 6, and frequently in excess of 12 or 24, months, and sometimes as much as 5 years or more.

While not wishing to be limited to theory, it is believed that the ability of the biocatalysts of this invention to possess the stable population of microorganisms in its interior is due to phenotypic changes to the microorganisms that occur during making the biocatalysts. These phenotype changes are believed to be due to the confluence of three primary factors. First is the use of a high concentration of microorganisms to make the biocatalyst, e.g., at least about 60, preferably at least about 100, grams of cells per liter, such that communication can occur among the cells at the time of formation of the biocatalyst. All references herein to the mass of cells are to the mass of wet cells. The high concentration of cells is also preferred as upon the phenotypic change occurring, little, if any, net growth in the population of the microorganisms occurs in the biocatalyst. In some instances, the net growth in population of microorganisms can be up to three or four fold until the steady-state population occurs. However, in most instances, the population of microorganisms at steady-state is plus or minus about 50, frequently plus or minus about 30, percent of the concentration of the cells initially used in preparing the biocatalyst.

The second major factor is that the biocatalyst when formed contains microorganisms in a plurality of interconnected major cavities of between about 5 and 100 microns in the smallest dimension. Preferably on a volumetric basis, at least about 20, and preferably at least about 50, percent of the interior structure of the biocatalyst (excluding the microorganisms) is composed of major cavities in this range. Although larger major cavities may be present, preferably less than about 25 percent of the interior of the solid structure is composed of these larger major cavities. Preferably the interconnected cavities in the biocatalyst are quiescent. It is believed that the high preponderance of the interconnected major cavities have a smallest dimension of between about 5 and 100 microns enhances the ability of the microorganisms located in the cavities to communicate such that the microorganisms, as a community, undergo phenotypic alteration.

The third major factor resides in the polymeric material component of the biocatalyst being hydrated and hydrophilic. It is believed that the microorganisms located in the interior of the biocatalyst as it is being made, especially those in the major cavities and smaller cavities, sense the hydrophilicity of the surface and this sensing of the environment also contributes to the phenotype change. The polymeric material is highly hydrated but yet contains sufficient hydrophobicity that the polymeric material in the biocatalyst is not dissolved or dispersed in water under the anticipated conditions of use. The hydrophilicity and the hydrophobicity of the polymer are such that the microorganisms become substantially irreversibly retained in the interior of the biocatalyst. As the retention of the microorganisms in the biocatalyst is due to a sensing by the microorganisms and their response, this irreversibly retention can be described as a metabolic retention. The biocatalysts can be characterized by having a Hydration Expansion Volume (HEV) of at least about 1,000, preferably at least about 5,000, and most often at least about 10,000. The Hydration Expansion Volume is indicative of the hydrophilicity of the polymeric material, and the higher the HEV, the greater is the hydrophilicity of the polymeric material.

Accordingly, in its broad aspects, the biocatalyst composition of this invention comprises:

a solid structure of hydrated hydrophilic polymer defining an interior structure having a plurality of interconnected major cavities having a smallest dimension of between about 5 and 100 microns and an HEV of at least about 1000, preferably at least about 5000, and a population of microorganisms substantially irreversibly retained in the interior structure, said microorganisms being in a concentration of at least about 60 grams per liter based upon the volume defined by the exterior of the solid structure when fully hydrated, wherein the microorganisms maintain a their population substantially stable.

Preferably the hydrophilic polymer also forms a skin on the exterior of the biocatalyst composition. Although the microorganisms have been found to become substantially irreversibly retained in the interior of the biocatalyst, generally the case is that the microorganisms are not significantly, if at all, in direct contact with the polymer although they can be in contact through fibrils, e.g., of extracellular polymeric substance, or strands of polymer. It is believed that the high hydrophilicity of the polymer reduces the ability of the microorganisms to adhere to the exterior surfaces of the biocatalyst under conditions of physical stress such as the flow of fluid over the exterior of the biocatalyst.

Another broad aspect of this invention pertains to methods for making biocatalyst compositions comprising:

a. forming a liquid dispersion, preferably an aqueous dispersion, of solubilized precursor for hydrophilic polymer and microorganisms for said biocatalyst wherein the concentration of microorganisms in the liquid dispersion is at least about 60, preferably at least about 100, grams per liter;

b. subjecting said dispersion to solidification conditions to form a solid structure of the hydrophilic polymer wherein the solid structure has an interior structure having a plurality of interconnected major cavities containing said microorganisms, said major cavities having a smallest dimension of between about 5 and 100 microns and wherein the solid structure has an HEV of at least about 1000, preferably at least about 5000, said solidification conditions not unduly adversely affecting the population of said microorganisms; and c. maintaining the solid structure containing microorganisms under conditions that do not adversely affect the population of said microorganisms in the interior of the solid structure for a time sufficient to enable the microorganisms to undergo a phenotypic alteration to maintain their population substantially stable and to become substantially irreversibly retained in the interior of the solid structure.

The solidification conditions may, in some instances, include the presence of a cross-linking agent, and the precursor is a solubilized prepolymer. Alternatively, the solidification conditions may comprise a reduction in temperature of the liquid dispersion such that polymer becomes solidified to form the solid structure. Often, the liquid dispersion not encompassed within the solid structure formed in step (b) is separated during or prior to step (c).

Other broad aspects of this invention pertain to metabolic processes in which the biocatalysts of this invention are subjected to metabolic conditions including the presence of substrate to bioconvert said substrate to bioproduct. The metabolic processes may be anabolic or catabolic. In the preferred processes, the microorganisms evidence a metabolic shift as compared to planktonic metabolism under substantially the same metabolic conditions.

BRIEF DESCRIPTION OF THE DRAWINGS

FIG. 8 depicts the sequencing of the modes of operation of each bioreactor assembly contained in the apparatus illustrated in FIG. 6.

DETAILED DESCRIPTION

Figure 1:
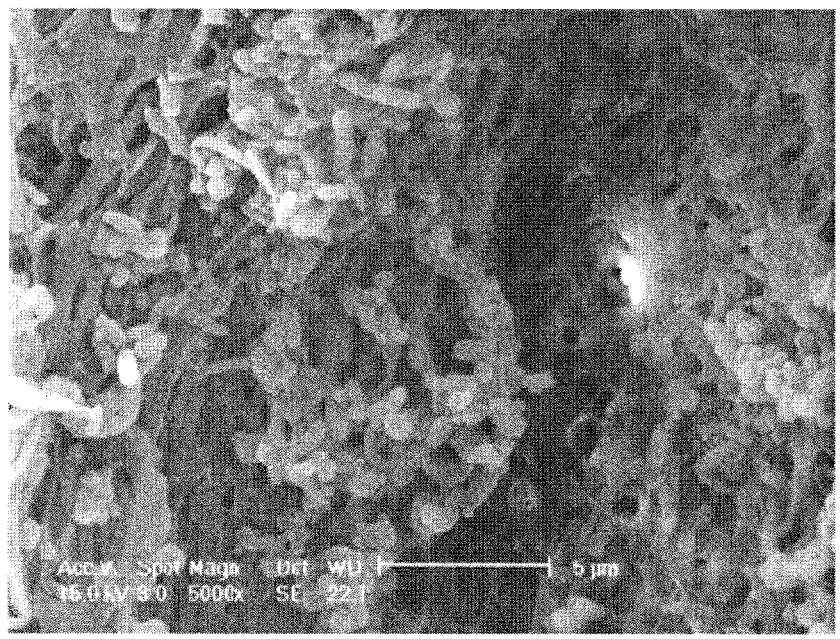
FIG. 1 is an SEM image of a portion of a cross-section of a biocatalyst in accordance with this invention.

All patents, published patent applications and articles referenced in this detailed description are hereby incorporated by reference in their entireties.

Definitions

As used herein, the following terms have the meanings set forth below unless otherwise stated or clear from the context of their use.

The use of the terms "a" and "an" is intended to include one or more of the element described. Lists of exemplary elements are intended to include combinations of one or more of the element described. The term "may" as used herein means that the use of the element is optional and is not intended to provide any implication regarding operability.

Adhering to the solid structure of the biocatalyst means that the microorganisms are located in cavities in the interior of the biocatalyst and are substantially irreversibly retained therein although extraordinary conditions and treatments (i.e., not normal bioconversion conditions for bioconversion using the microorganisms) might be able in some instances to cause the microorganism to exit the biocatalyst. Adhering includes surface attachment to the polymer forming the walls of the porous matrix as well as where the retained microorganisms are proximate to a polymeric surface, e.g., within about 10 or 20 microns, but not directly contacting the surface. Adhering thus includes physical and electrostatic adherence. In some instances, the polymer used to make the biocatalyst may become embedded in the extracellular polymeric substance around a cell or even in or on the cell wall of the microorganism.

Ammonium cation includes ammonium cation and dissolved ammonia. One test for determining ammonium cation concentration is the salicylate method test N tube, Hach Method 10031, DOC316.53.01079, $7^{th}$ edition.

BTT Test is a batch toxicity tolerance test. The BTT Test compares the tolerance of a free suspension of the microorganism to a toxin in an aqueous medium under metabolic conditions with the tolerance of the same microorganism but provided in a substantially the same aqueous medium under substantially the same metabolic conditions but in porous matrices to provide substantially the same starting cell density. The subject toxin is added to the aqueous medium at a concentration such that the bioconversion of the substrate after 24 hours is approximately 50 percent of that in the absence of the toxin (or in the case of a substrate that can be toxic, a concentration having substantially no adverse effect on the microorganism). It is not essential that the bioconversion be precisely 50 percent less, but it should be in the range of between about 35 and 65 percent of that in the absence of the toxin. The same concentration of the toxin is added to the aqueous medium containing the microorganisms in the porous matrices and the bioconversion of the substrate after 24 hours is determined. It is understood that the metabolic conditions may, in some instances, affect how much of an effect the toxin has on the microorganism. In such instances, the metabolic conditions should be selected to be generally midrange of those suitable for the bioconversion. Also, it is understood that the degree of improvement provided by this invention can vary with different toxins. Accordingly, the toxin used should be the toxin at issue for the specific metabolic process. For instance, if the process is to make isobutanol as the bioproduct, the toxin used should be contained in the aqueous medium for the bioconversion and should not be a toxin such as sodium hypochlorite which is not expected to be in the medium. For phage as toxins, the toxin added may be infected cells.

Biochemical oxygen demand (BOD) is the amount of oxygen required for metabolic conversion of organic carbon in water to carbon dioxide and is an indication of the organic compounds available for food. BOD is reported as milligrams per liter. BOD can be determined by Standard Method 5210B, revision Nov. 16, 1999, as published by the U.S. Environmental Protection Agency Bioconversion activity is the rate of consumption of substrate per hour per gram of microorganism. Where an increase or decrease in bioconversion activity is referenced herein, such increase or decrease is ascertained under similar bioconversion conditions including concentration of substrate and product in the aqueous medium. Bioconversion activity to bioproduct is the rate of production of the bioproduct per hour per gram of microorganism.

Biofilm means an aggregate of microorganisms embedded within an extracellular polymeric substance (EPS) generally composed of polysaccharides, and may contain other components such as one or more of proteins, extracellular DNA and the polymer used to make the biocatalyst. The thickness of a biofilm is determined by the size of the aggregate contained within a continuous EPS structure, but a continuous EPS structure does not include fibrils that may extend between separated biofilms. In some instances, the biofilm extends in a random, three dimensional manner, and the thickness is determined as the maximum, straight line distance between the distal ends. A thin biofilm is a biofilm which does not exceed about 10 microns in any given direction.

Bioproduct means a product of a bioconversion which may be an anabolic product or a catabolic product and includes, but is not limited to, primary and secondary metabolites.

Contaminating microorganisms are microorganisms that compete with the microorganisms for the bioconversion of substrate and may be adventitious or from an up-stream bioconversion process. With reference to the biocatalysts of this invention, contaminating microorganisms also include those that can foul the surface of the biocatalyst even though they may not compete for substrate.

Chemical oxygen demand (COD) is the amount of oxygen required to convert organic carbon in water to carbon dioxide and thus is an indication of the organic compound content of the water. COD is reported as milligrams per liter. One procedure for determining COD is Hach Method 8000, February 2009, Ninth Edition.

A state of essential stasis means that a microorganism population has undergone a substantial cessation of all metabolic bioconversion activity but can be revived. The existence of an essential stasis condition can be ascertained by measuring bioconversion activity. The essential stasis condition may be aerobic, anoxic or anaerobic which may or may not be the same as that of normal operating conditions for the microorganism. Where stasis is sought, the temperature is typically in the range of about 0° C. to 25° C., say, 4° C. to 15° C. which may be different from the temperatures used at normal operating conditions.

An exo-network is a community of spaced-apart microorganisms that can be in the form of individual cells or biofilms that are interconnected by extracellular polymeric substance in the form of strands. The spacing between the microorganisms or biofilms in the exo-network is sufficient to enable the passage of nutrients and substrates there between and is often at least about 0.25, say, at least about 0.5, micron and may be as large as 5 or 10 microns or more.

Exterior skin is an exterior layer of polymer on the biocatalyst that is less open than the major channels in the interior structure of the biocatalyst. A biocatalyst may or may not have a skin. Where a skin is present, it may or may not have surface pores. Where no surface pores are present, fluids diffuse through the skin. Where pores are present, they often have an average diameter of between about 1 and 10 microns.

Fully hydrated means that a biocatalyst is immersed in water at 25° C. until no further expansion of the superficial volume of the biocatalyst is perceived.

The "Hydration Expansion Volume" (HEV) for a biocatalyst is determined by hydrating the biocatalyst in water at 25° C. until the volume of the biocatalyst has stabilized and measuring the superficial volume of the biocatalyst ($V_w$), removing the biocatalyst from water and removing excess water from the exterior, but without drying, and immersing the biocatalyst in ethanol at 25° C. for a time sufficient that the volume of the biocatalyst has stabilized and then measuring the superficial volume of the biocatalyst ($V_s$).

The HEV in volume percent is calculated as the amount of $[V_w/V_s] \times 100\%$.

To assure dehydration with the ethanol, either a large volume ratio of ethanol to biocatalyst is used or successive immersions of the biocatalyst in fresh ethanol are used. The ethanol is initially dehydrated ethanol.

Irreversibly retained and substantially irreversibly retained mean that the microorganisms are adhering to polymeric structures defining open, porous cavities. Irreversibly retained microorganisms do not include microorganisms located on the exterior surface of a biocatalyst. A microorganisms is irreversibly retained even if the biocatalyst has exterior pores of sufficient size to permit egress of the microorganisms.

Highly hydrophilic polymers are polymers to which water is attracted, i.e., are hydroscopic. Often the polymers exhibit, when cast as a film, a water contact angle of less than about 60°, and sometimes less than about 45°, and in some instances less than about 10°, as measured by the sessile drop method using a 5 microliter drop of pure distilled water.

Highly hydrated means that the volume of the biocatalyst (excluding the volume of the microorganisms) is at least about 90 percent water.

An isolated enzyme is an enzyme removed from a cell and may or may not be in a mixture with other metabolically active or inactive materials.

Macroorganisms include, but are not limited to, mollusks, such as bivalve mollusks including mussels and clams; barnacles; bryozoan; polychette; and macroalgae.

A matrix is an open, porous, polymeric structure and is an article of manufacture having an interconnected plurality of channels or cavities (herein "major cavities") defined by polymeric structures, said cavities being between about 5 and 100 microns in the smallest dimension (excluding any microorganisms contained therein), wherein fluid can enter and exit the major cavities from and to the exterior of the matrix. The porous matrix may contain larger and smaller channels or cavities than the major cavities, and may contain channels and cavities not open to the exterior of the matrix. The major cavities, that is, open, interconnected regions of between about 5 or 10 to 70 or 100 microns in the smallest dimension (excluding any microorganism contained therein) have nominal major dimensions of less than about 300, preferably less than about 200, microns, and sometimes a smallest dimension of at least about 10 microns. The term open, porous thus refers to the existence of channels or cavities that are interconnected by openings therebetween.

Metabolic conditions include conditions of temperature, pressure, oxygenation, pH, and nutrients (including micronutrients) and additives required or desired for the microorganisms in the biocatalyst. Nutrients and additives include growth promoters, buffers, antibiotics, vitamins, minerals, nitrogen sources, and sulfur sources and carbon sources where not otherwise provided.

A metalate is an oxyanion, hydroxyl or salt of a metal or semiconductor element.

Municipal wastewater is collected wastewater from two or more sources wherein wastewater is generated by human activity including, but not limited to, human and animal excrement; domestic, commercial, agricultural, mining and industrial wastes and drainage; storm runoff; foodstuffs; and product, intermediate and raw materials disposal.

Oxygenated organic product means a product containing one or more oxygenated organic compounds having 2 to 100, and frequently 2 to 50, carbons and at least one moiety selected from the group consisting of hydroxyl, carbonyl, ether and carboxyl.

Permeable means that a component can enter or exit the major cavities from or to the exterior of the biocatalyst.

Population of microorganisms refers to the number of microorganisms in a given volume and includes substantially pure cultures (axenic) and mixed cultures.

A phenotypic change or alternation or phenotypic shift is a change in a microorganism's traits or characteristics from environmental factors and is thus different from a change in the genetic make-up of the microorganism.

Quiescent means that the aqueous medium in a biocatalyst is still; however, flows of nutrients and substrates and bioproducts can occur through the aqueous medium via diffusion and capillary flow.

Retained solids means that solids are retained in the interior of the biocatalyst. The solids can be retained by any suitable mechanism including, but not limited to, restrained by not being able to pass through pores in the skin of a biocatalyst, by being captured in a biofilm or a polysaccharide structure formed by microorganisms, by being retained in the polymeric structure of the biocatalyst, or by being sterically entangled within the structure of the biocatalyst or the microorganisms.

Smallest dimension means the maximum dimension of the shortest of the maximum dimensions defining the length, width and height of a major cavity. Usually a preponderance of the major cavities in a matrix are substantially width and height symmetrical. Hence the smallest dimension can be approximated by the maximum width of a cavity observed in a two dimensional cross section, e.g., by optical or electronic microscopy.

A solubilized precursor for the polymer is a monomer or prepolymer or the polymer itself that is dissolved or dispersed such that solids cannot be seen by the naked eye and is stable. For instance, a solid can be highly hydrated and be suspended in an aqueous medium even though the solid is not dissolved.

Sorption means any physical or chemical attraction and can be adsorption or absorption and may be relatively weak, e.g., about 10 kilojoules per mole or a chemical interaction with a sorbent. Preferably the sorptive attraction by the sorbent is greater than that between water and the substrate, but not so great that undue energy is required to desorb the substrate. Frequently the sorptive strength is between about 10 and 70, say, 15 and 60, kilojoules per mole. A sorbent is a solid having sorptive capacity for at least one substrate.

A stable population of microorganisms means that the population of microorganisms does not decrease by more than 50 percent nor increase by more than 400 percent. The stability of the microorganism population can usually be ascertained from the change, or lack of change, in bioconversion activity of the biocatalyst in its intended use.

Sterilization means any process that kills all forms of microbial life, and a sterilizing agent means one or more chemicals or processes that can effect sterilization. Sterilization is thus a nonselective process as it affects all forms of microbial life. Disinfection may be sterilization or may affect microbial life without killing the microorganisms. A disinfecting agent means one or more chemicals or processes that can effect disinfection.

Substrates are carbon sources, electron donors, electron acceptors and other chemicals that can be metabolized by a microorganism, which chemicals, may or may not provide sustaining value to the microorganisms.

Sugar means carbohydrates having 5 to 12 carbon atoms and includes, but is not limited to, D-glyceraldehyde, L-glyceraldehyde, D-erythrose, L-erythrose, D-threose, L-threose, D-ribose, L-ribose, D-lyxose, L-lyxose, D-allose, L-allose, D-altrose, L-altrose 2-keto-3-deoxy D-gluconate (KDG), D-mannitol, guluronate, mannuronate, mannitol, lyxose, xylitol, D-glucose, L-glucose, D-mannose, L-mannose, D-gluose, L-gluose, D-idose, L-idose, D-galactose, L-galactose, D-xylose, L-xylose, D-arabinose, L-arabinose, D-talose, L-talose, glucuronate, galacturonate, rhamnose, fructooligosaccharide (FOS), galactooligosaccharide (GOS), inulin, mannan oligosaccharide (MOS), oligoalginate, mannuronate, guluronate, alpha-keto acid, or 4-deoxy-L-erythro-hexoselulose uronate (DEHU).

Typical Bioreactor Systems are those operated on a continuous, semi-continuous or batch mode of operation and include bioreactor designs such as, but are not limited to, ponds (in the case of photosynthetic processes), bubble column reactors, stirred reactors, packed bed reactors, trickle bed reactors, fluidized bed reactors, plug flow (tubular) reactors, and membrane (biofilm) reactors. In conducting photosynthetic bioconversions, the reactors may be designed to permit the transfer of photo energy. The biocatalyst may be freely mobile in the aqueous medium or fixed, e.g., to a structure in the reactor vessel, or may itself provide a fixed structure. More than one reactor vessel may be used. For instance, reactor vessels may be in parallel or in sequential flow series.

Typical Mesophilic Conditions are metabolic conditions that include a temperature in the range of between about 0° C. and 50° C. or more depending upon the temperature tolerance of the microorganism, most frequently, about 5° C. or 10° C. to 40° C. or 45° C.; a pressure in the ranges from about 70 to 500, say, 90 to 300, kPa absolute due to equipment configurations although higher and lower pressures could find applicability; and a pH in the range of between about 3 and 9. The Typical Mesophilic Conditions can be aerobic or anaerobic.

Typical Separation Techniques for chemical products include phase separation for gaseous chemical products, the use of a still, a distillation column, phase separation (liquid-liquid and solid-liquid), gas stripping, flow-through centrifuge, Karr column for liquid-liquid extraction, mixer-settler, or expanded bed adsorption. Separation and purification steps may proceed by any of a number of approaches combining various methodologies, which may include centrifugation, filtration, reduced pressure evaporation, liquid/liquid phase separation, membranes, distillation, and/or other methodologies recited herein. Principles and details of standard separation and purification steps are known in the art, for example in "Bioseparations Science and Engineering," Roger G. Harrison et al., Oxford University Press (2003), and Membrane Separations in the Recovery of Biofuels and Biochemicals—An Update Review, Stephen A. Leeper, pp. 99-194, in Separation and Purification Technology, Norman N. Li and Joseph M. Calo, Eds., Marcel Dekker (1992).

The wet weight or wet mass of cells is the mass of cells from which free water has been removed, i.e., are at the point of incipient wetness.

References to organic acids herein shall be deemed to include corresponding salts and esters.

References to biocatalyst dimensions and volumes herein are of fully hydrated biocatalyst unless otherwise stated or clear from the context.

Biocatalyst

A. Biocatalyst Overview

The biocatalysts of this invention have a polymeric structure (matrix) defining interconnected major cavities, i.e., are open, porous matrices, in which the microorganisms are metabolically retained in the interior of the matrices, that is, the microorganisms promote the adherence rather than being physically restrained by an external structure. In the biocatalysts of this invention, the microorganisms and their communities, inter alia, regulate their population. Also, in conjunction with the sensed nature of the microenvironment in the matrices, it is believed that the microorganisms establish a spatial relationship among the members of the community.

The community communication among the microorganisms and the behavior of the microorganisms thus are important to achieving and maintaining the metabolically retained microorganisms. The communication among the microorganisms is believed to occur through emitting chemical agents, including, but not limited to, autoinducers, and communication includes communications for community behavior and for signaling. Often, the preparation of the biocatalysts used in the processes of this invention can result in a population of microorganisms being initially located in the interior of the biocatalyst that is substantially that which would exist at the steady-state level. At these densities of microorganisms in the biocatalysts, community communications are facilitated which are believed to commence during the formation of the biocatalysts, and phenotypic shifts occur to enable the metabolic retention and modulate the population of microorganisms.

The environment to achieve the metabolically-retained, stable population of microorganisms is characterized by a highly hydrated structure of hydrophilic polymer, which structure defines a plurality of interconnected cavities of between about 5 and 100 microns in the smallest dimension and has a Hydration Expansion Volume (HEV) of at least about 1000. The structure thus defines the microenvironments for the microorganisms. These microenvironments not only facilitate communication among the microorganisms but also in some instances modulate the environmental stresses on the microorganisms and modulate the supply of substrate and nutrients to the microorganisms. The highly hydrated and expanded structure of the porous matrices and its openness also can accommodate the metabolic retention of a large population of microorganisms and accommodate community behaviors associated with the metabolic retention.

Without wishing to be limited to theory, it is believed that the very high HEV of the matrices means that that water exists within the solid structure itself. The absorbed water is believed to act through van der Waals interactions or hydrogen bonding with the hydrophilic polymer to interconnect polymer chains and strengthen the polymeric structure in the expanded state. When water is removed by dehydration, the polymer strands can collapse in such a manner as to enable significant shrinkage of the structure. The hydrated polymeric structure is believed to have a low average surface energy while still being able to provide sites for attachment by the microorganisms. In some instances the highly hydrated polymeric surface which itself may be a source of water and nutrients due to the hydration.

The microorganisms that are retained in the matrices have the ability to form an exo-network. The quiescent nature of the cavities facilitate forming and then maintaining any formed exo-network. A discernable exo-network is not believed essential to achieving phenotypic alterations in the microorganism population such as population modulation and metabolic shift. Where an exo-network develops, often strands of EPS interconnect proximate microorganisms and connect microorganisms to the surface and form the exo-network. In some instances, the microorganisms form thin biofilms and these thin biofilms are encompassed in the exo-network. The biocatalysts of this invention have a substantial absence of biofilms in their interiors that are larger than thin biofilms. Hence, any biofilms that may ultimately form in the biocatalysts are relatively thin, e.g., up to about 10, and preferably up to about 2 or 5, microns in thickness, and stable in size. Thus, each thin biofilm is often only a few cells and is connected in an exo-network.

Figure 2:
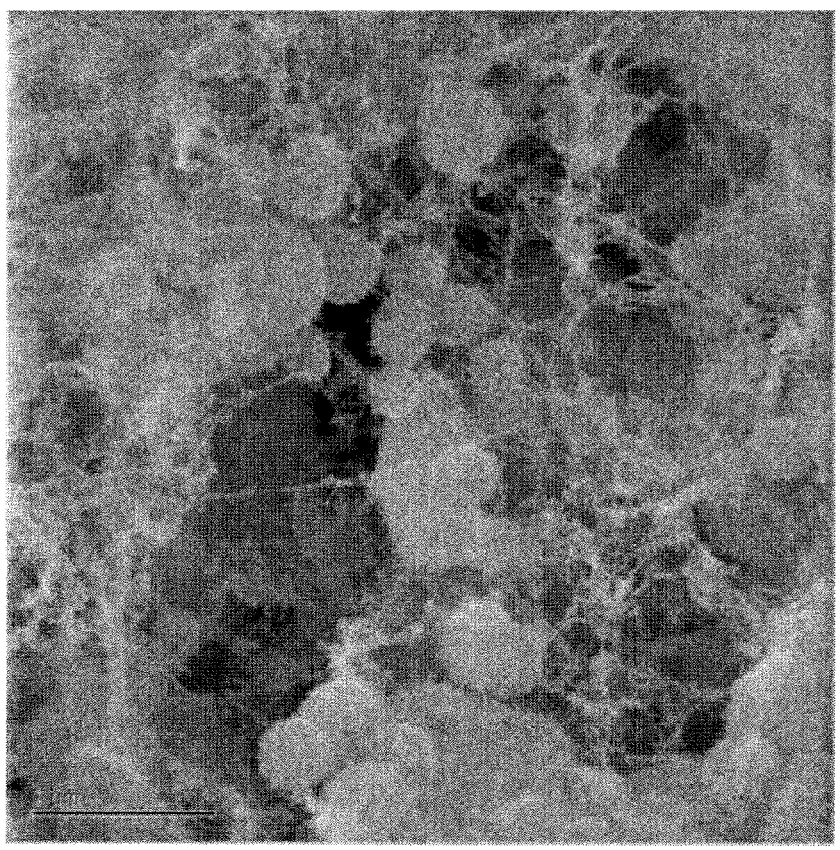
FIG. 2 is an SEM image of a portion of a cross-section of another biocatalyst in accordance with this invention.

FIGS. 1 and 2 are SEM images illustrating two potential configurations of microorganisms within major cavities in the interior of biocatalysts of this invention. These images are not in limitation of the broad aspects of the invention. Each biocatalyst is used in a bioconversion for extended periods of time prior to being prepared for SEM analysis. The bioconversion activity of each biocatalyst remains substantially constant over the duration of the bioconversion: The biocatalyst of FIG. 1 comprises *Saccharomyces cerevisiae* and had been used to make ethanol from sugar over about a 2 week period. The biocatalyst during its use evidenced that the microorganisms were irreversibly retained and a metabolic shift towards higher conversion efficiency to ethanol had occurred. The biocatalyst of FIG. 2 comprises *Achromobacter denitrificans* and was used for nitrate and perchlorate degradation for about 1 month of continuous flow operation. This biocatalyst also evidenced that the microorganisms were irreversibly retained in the biocatalyst and effectively degraded perchlorate and nitrate anions without the generation of solids. Each image depicts that the microorganisms are in a high population density but have a spatial configuration that does not evidence overgrowth or the formation of thick biofilms. The exo-network observable in FIG. 1 further evidences that an additional phenotypic has occurred in that the interconnection of the microorganisms is not characteristic of yeasts used in bioconversion processes. FIG. 2 illustrates the formation of an exo-network. In general, more extensive exo-networks, when the microorganism generates EPS, occur over the duration of use of the biocatalyst.

It is believed that in some instances the spatial configuration of the interior of the biocatalyst and any exo-network promotes communication among the microorganisms. The communications may be able to extend to spaced apart exo-networks and thin biofilm units. As a general rule, the strength, or concentration, of autoinducers is amplified by microorganisms in response to that autoinducer being emitted by another microorganism. This amplification is enhanced by the spatial configuration of the microenvironment in the interior of the biocatalyst and in some instances, the chemical composition of the polymer forming the biocatalyst. The import of the spacial configuration of the major cavities to the phenotypic alteration and population stability has been demonstrated by examination of biocatalysts containing large cavities, e.g., greater than about 1000 microns in the smallest dimension. Although the biocatalyst exhibits bioconversion activity, the surface of the large cavities appeared to be substantially devoid of any microorganisms in contrast to a large, stable population of microorganisms in smaller cavities.

The communications are believed to result in the community of microorganisms maintaining a relatively constant population in the interior of the biocatalyst. Another phenotypic alteration occurring in the biocatalysts of this invention, which is believed to be a result of this communication, is a metabolic shift, i.e., the metabolic functions of the community towards reproduction are diminished and the sought bioconversion continues. The population of microorganisms in the biocatalyst may tend to have an old average age due to this shift in the metabolic activity. Older microorganisms also tend to provide a more robust and sustainable performance as compared to younger cells as the older cells have adapted to the operating conditions.

Additional benefits of this communication can be an increase in community-level strength or fitness exhibited by the community in warding off adventitious microorganisms and maintaining strain-type uniformity. In some instances, the microorganisms during use of the biocatalyst may undergo natural selection to cause the strain-type in the community to become heartier or provide another benefit for the survival of the community of microorganisms. In some instances, the communication among the microorganisms may permit the population of microorganisms to exhibit multicellularity or multicellular-like behaviors. Thus the population of microorganisms in a biocatalyst of this invention may have microorganisms adapting to different circumstances but yet working in unison for the benefit of the community.

In some instances the porous matrix may provide modulation of the substrate and nutrients to the microorganisms to optimize metabolic pathways involving substrates that are available, and these pathways may or may not be the primarily used pathways where ample substrate and other nutrients are available. Accordingly, microorganisms in the biocatalysts may exhibit enhanced bioactivity for a primarily used pathway or metabolic activity that is normally repressed.

It is also believed that the microenvironments may promote genetic exchange or horizontal gene transfer. Conjugation or bacterial mating may also be facilitated, including the transfer of plasmids and chromosomal elements. Moreover, where microorganisms lyse, strands of DNA and RNA in the microenvironments are more readily accessible to be taken up by microorganisms in these microenvironments. These phenomena can enhance the functional abilities of the microorganisms.

The biocatalysts exhibit an increased tolerance to toxins. In some instances, communications among microorganisms and any exo-network may facilitate the population establishing defenses against toxins. The community response to the presence of toxins has been observed in the biocatalysts of this invention. For instance, the biocatalysts survive the addition of toxins such as ethanol and sodium hypochlorite and the original bioconversion activity is quickly recovered thus indicating the survival of essentially the entire community.

If desired, the biocatalysts may be treated to enhance the formation of the exo-network, and if desired, thin biofilms, prior to use in the metabolic process. However, performance of the biocatalyst is not generally dependent upon the extent of exo-network formation, and often bioconversion activities remain relatively unchanged between the time before the microorganisms have attached to the polymeric structure and the time when extensive exo-network structures have been generated.

B. Physical Description of the Porous Matrices

The biocatalysts of this invention comprise a matrix having open, porous interior structure with microorganisms irreversibly, metabolically retained in at least the major cavities of the matrix.

The matrices may be a self-supporting structure or may be placed on or in a preformed structure such as a film, fiber or hollow fiber, or shaped article. The preformed structure may be constructed of any suitable material including, but not limited to, metal, ceramic, polymer, glass, wood, composite material, natural fiber, stone, and carbon. Where self-supporting, the matrices are often in the form of sheets, cylinders, plural lobal structures such as trilobal extrudates, hollow fibers, or beads which may be spherical, oblong, or free-form. The matrices, whether self-supporting or placed on or in a preformed structure, preferably have a thickness or axial dimension of less than about 5, preferably less than about 2, say, between about 0.01 to 1, centimeters.

The porous matrices may have an isotropic or, preferably, an anisotropic structure with the exterior portion of the cross section having the densest structure. The major cavities, even if an anisotropic structure exists, may be relatively uniform in size throughout the interior of the matrix or the size of the major cavities, and their frequency, may vary over the cross-section of the biocatalyst.

The biocatalyst of this invention has major cavities, that is, open, interconnected regions of between about 5 or 10 to 70 or 100 microns in the smallest dimension (excluding any microorganisms contained therein). For the purposes of ascertaining dimensions, the dimensions of the microorganisms include any mass in the exo-network. In many instances, the major cavities have nominal major dimensions of less than about 300, preferably less than about 200, microns, and sometimes a smallest dimension of at least about 10 microns. Often the biocatalyst contains smaller channels and cavities which are in open communication with the major cavities. Frequently the smaller channels have a maximum cross-sectional diameter of between about 0.5 to 20, e.g., 1 to 5 or 10, microns. The cumulative volume of major cavities, excluding the volume occupied by microorganisms and mass associated with the microorganisms, to the volume of the biocatalyst is generally in the range of about 40 or 50 to 70 or 99, volume percent. In many instances, the major cavities constitute less than about 70 percent of the volume of the fully catalyst with the remainder constituting the smaller channels and pores. The volume fraction of the biocatalyst that constitutes the major cavities can be estimated from its cross-section. The cross section may be observed via any suitable microscopic technique, e.g., scanning electron microscopy and high powered optical microscopy. The total pore volume for the matrices can be estimated from the volumetric measurement of the matrices and the amount and density of polymer, and any other solids used to make the matrices.

The biocatalyst is characterized by having high internal surface areas, often in excess of at least about 1 and sometimes at least about 10, square meter per gram. In some instances, the volume of water that can be held by a fully hydrated biocatalyst (excluding the volume of the microorganisms) is in the range of 90 to 99 or more, percent. Preferably the biocatalyst exhibits a Hydration Expansion Volume (HEV) of at least about 1000, frequently at least about 5000, preferably at least about 20,000, and sometimes between 50,000 and 200,000, percent.

Usually the type of polymer selected and the void volume percent of the matrices are such that the matrices have adequate strength to enable handling, storage and use in a bioconversion process.

The porous matrices may or may not have an exterior skin. Preferably the matrices have an exterior skin to assist in modulating the influx and efflux of components to and from the interior channels of the porous matrix. Also, since the skin is highly hydrophilic, and additional benefit is obtained as contaminating or adventitious microorganisms have difficulties in establishing a strong biofilm on the exterior of the biocatalyst. These contaminating microorganisms are often subject to removal under even low physical forces such as by the flow of fluid around the biocatalysts. Thus, the fouling of the biocatalyst can be substantially eliminated or mitigated by washing or by fluid flows during use.

Where present, the skin typically has pores of an average diameter of between about 1 and 10, preferably 2 to 7, microns in average diameter. The pores may comprise about 1 to 30, say, 2 to 20, percent of the external surface area. The external skin, in addition to providing a barrier to entry of adventitious microorganisms into the interior of the biocatalyst, is preferably relatively smooth to reduce the adhesion of microorganisms to the external side of the skin through physical forces such as fluid flow and contact with other solid surfaces. Often, the skin is substantially devoid of anomalies, other than pores, greater than about 2 or 3 microns. Where a skin is present, its thickness is usually less than about 50, say, between about 1 and 25, microns. It should be understood that the thickness of the skin can be difficult to discern where the porous matrix has an anisotropic structure with the densest structure being at the exterior of the matrix.

The porous matrices provide a plurality of unique microenvironments and nano-environments within their interiors. These unique microenvironments and nano-environments result in enzymes or microorganisms located at different regions within the biocatalyst being subjected to different metabolic conditions. The metabolic conditions may differ in one or more of composition, oxidation or reduction potential and pH. For instance, the composition may vary based upon electron donor, other nutrients, contaminants, bioconversion products, and the like, and thus can affect the metabolic processes within the microorganism in such environment. Hence, it is possible to have within the same matrix, aerobic and anaerobic metabolism and to have enhanced bioconversion of a less preferred substrate as the more preferred substrate is metabolized. This ability to have plural, enhanced bioconversions can occur using a single strain of microorganism or using two or more different strains. In some instances, different phenotypic changes may occur depending upon the microenvironment in which the microorganisms are located.

A number of factors contribute to the existence of these unique microenvironments. For instance, concentration gradients are a major driving force for the ingress and egress of components in the aqueous phase in these channels. As the microorganisms in the biocatalyst bioconvert components, concentration gradients occur, especially along channels extending from the major cavities. The changes in concentration of components thus results in variations of component concentrations within the biocatalyst. In some situations, the microorganisms having a reduced supply of electron donor or nutrients at one or more regions within the biocatalyst may be at or near starvation which can result in phenotypic changes leading to resistance to stress. The bioconversion and consequent gradient changes also affects the rate of ingress from and egress to the exterior of the biocatalyst of components.

A high density of microorganisms can exist at steady-state operation within the biocatalysts. The combination of the flow channels and the high permeability of the polymeric structure defining the channels enable viable microorganism population throughout the matrix, albeit with a plurality of unique microenvironments and nano-environments. In some instances, the cell density based upon the volume of the biocatalyst is preferably at least about 100 grams per liter, preferably at least about 200, and often between about 250 and 750, grams per liter.

Polysaccharide-Containing Biocatalysts

In one preferred aspect of the biocatalyst of this invention, it has been found that through incorporating polysaccharide in the interior of the biocatalyst, the viability of the microorganism population can be maintained. Typically polysaccharides are not usable by most microorganisms. Often, the polysaccharide is provided in an amount of at least about 0.1, say, at least about 0.2 to 100, gram per gram of cells retained in the biocatalyst, and sometimes the biocatalyst contains between 25 and 500 grams of polysaccharide per liter of volume of fully hydrated biocatalyst. The polysaccharide particles used in preparing the biocatalysts preferably have a major dimension of less than about 50, preferably less than about 20, often between about 0.1 to 5, microns. The solid polysaccharide particles are preferably granular and often have an aspect ratio of minimum cross-sectional dimension to maximum cross sectional dimension of between about 1:10 to 1:1, say 1:2 to 1:1.

Due to the ability of the polysaccharide to maintain the viability of the microorganisms in the biocatalyst, the storage, handling and processes for use of the biocatalyst can be facilitated. For instance, the biocatalysts can be used in bioconversion processes which are operated in a carbon deficient manner. In metabolic processes where carbon source is added to maintain the microorganisms and not used in the sought bioconversion of substrate to bioproduct, such as in the catabolysis of nitrate, nitrite, and perchlorate anions and the metabolic reduction of metalates, the polysaccharide may serve as the sole source of carbon and thereby eliminate the necessity of adding carbon source, or it may reduce the amount of carbon source added, i.e., permit carbon deficient operation. An advantage is that the bioprocesses can be operated such that the effluent has essentially no COD. The biocatalysts also have enhanced abilities to tolerate disruptions in substrate presence and be able to quickly regain bioconversion activity. Also, the biocatalysts can be remotely manufactured and shipped to the location of use without undue deleterious effect on the bioconversion activity of the biocatalyst. The biocatalysts may be able enter a state of essential stasis for extended durations of time in the absence of supplying substrate and other nutrients to the microbial composites even where excursions in the desired storage conditions such as temperature occur. The bioactivity can be quickly regained in a bioreactor even after extended episodic occurrences of shutdown, feedstock disruption, or feedstock variability. The biocatalysts can be packaged and shipped in sealed barrels, tanks, and the like.

The polysaccharide may be from any suitable source including, but not limited to, cellulosic polysaccharides or starches. Polysaccharides are carbohydrates characterized by repeating units linked together by glycosidic bonds and are substantially insoluble in water. Polysaccharides may be homopolysaccharides or heteropolysaccharides and typically have a degree of polymerization of between about 200 and 15,000 or more, preferably between about 200 and 5000. The preferred polysaccharides are those in which about 10, more preferably, at least about 20, percent of the repeating units are amylose (D-glucose units). Most preferably the polysaccharide has at least about 20, more preferably, at least about 30, percent of the repeating units being amylose. The polysaccharides may or may not be functionalized, e.g., with acetate, sulfate, phosphate, pyruvyl cyclic acetal, and the like, but such functionalization should not render the polysaccharide water soluble at temperatures below about 50° C. A preferred class of polysaccharides is starches.

Sources of polysaccharides include naturally occurring and synthetic (e.g., polydextrose) polysaccharides. Various plant based materials providing polysaccharides include but are not limited to woody plant materials providing cellulose and hemicellulose, and wheat, barley, potato, sweet potato, tapioca, corn, maize, cassava, milo, rye and brans typically providing starches.

Solid Sorbent-Containing Biocatalysts

In another preferred aspect of the biocatalysts of this invention, the biocatalysts comprise a solid sorbent. The solid sorbent may be the hydrophilic polymer forming the structure or may be a particulate, i.e., a distinct solid structure regardless of shape) contained in the solid structure. The sorbent may be any suitable solid sorbent for the substrate or nutrients or other chemical influencing the sought metabolic activity such as, but not limited to, co-metabolites, inducers, and promoters or for components that may be adverse to the microorganisms such as, and not in limitation, toxins, phages, bioproducts and by-products. The solid sorbent is typically an adsorbent where the sorption occurs on the surface of the sorbent. The particulate solid sorbents are preferably nano materials having a major dimension less than about 5 microns, preferably, between about 5 nanometers to 3 microns. Where the solid sorbent is composed of polymer, the solid structure may be essentially entirely composed of the polymer or may be a block copolymer or polymeric mixture constituting between about 5 and 90 mass percent of the solid structure (excluding water). Where the solid sorbent is a separate particulate in the biocatalyst, the biocatalyst may comprise between about 5 to 90 mass percent of the mass of the biocatalyst (excluding water and microorganisms but including both the hydrophilic polymer and the particulates). More than one solid sorbent may be used in a biocatalyst. Preferably the solid sorbent is relatively uniformly dispersed throughout the interior of the biocatalyst although the solid sorbent may have a varying distribution within the biocatalyst. Where the distribution varies, the regions with the higher concentration of solid sorbent often are found toward the surface of the biocatalyst.

Where a particulate sorbent is used, the sorbent comprises an organic or inorganic material having the sought sorptive capacity. Examples of solid sorbents include, without limitation, polymeric materials, especially with polar moieties, carbon (including but not limited to activated carbon), silica (including but not limited to fumed silica), silicates, clays, molecular sieves, and the like. The molecular sieves include, but are not limited to zeolites and synthetic crystalline structures containing oxides and phosphates of one or more of silicon, aluminum, titanium, copper, cobalt, vanadium, titanium, chromium, iron, nickel, and the like. The sorptive properties may comprise one or more of physical or chemical or quasi-chemical sorption on the surface of the solid sorbent. Thus, surface area and structure may influence the sorptive properties of some solid sorbents. Frequently the solid sorbents are porous and thus provide high surface area and physical sorptive capabilities. Often the pores in the solid sorbents are in the range of about 0.3 to 2 nanometers in effective diameter.

The solid sorbent may be incorporated into the polymeric structure in any convenient manner, preferably during the preparation of the biocatalyst.

Phosphorescent Biocatalysts

Another preferred aspect of the invention pertains to biocatalysts containing phosphorescent material and photosynthetic microorganisms, i.e., microorganisms that uses light energy in a metabolic process. Preferably the microorganism is an algae, most preferably a microalgae, or cyanobacteria.

The bioactivity of photosynthetic microorganisms can be enhanced to produce expressed bioproduct using broad-based light source such as sunlight. In accordance with the invention, the photosynthetic microorganisms are irreversibly retained in biocatalysts in which the interior of the biocatalyst contains phosphorescent material capable of shifting UV light to light having a wavelength of between about 400 and 800, preferably between about 450 and 650, nm and is capable of exhibiting persistence, with the emission of the light often lasting for at least about 5 seconds. A phosphorescent material is a material that has the ability to be excited by electromagnetic radiation into an excited state, but the stored energy is released gradually. Emissions from phosphorescent materials have persistence, that is, emissions from such materials can last for seconds, minutes or even hours after the excitation source is removed. A luminescent material is a material capable of emitting electromagnetic radiation after being excited into an excited state. Persistence is the time it takes, after discontinuing irradiation, for photoluminescent emissions emanating from a photoluminescent object to decrease to the threshold detectability.

The persistence of the radiation enables the microorganisms to be cycled in and out of a region of the culture liquid exposed to the light source and still be productive. With longer persistence durations, the photosynthetic microorganisms can continue photo-bioconversion in the absence of or reduction in light intensity. The ability of the biocatalysts to maintain photosynthetic activity over extended periods of time, often at least about 30 days, and in some instances for at least one year, the cost of the phosphorescent materials is often offset by the increased production, reduced footprint of the bioreactor, and facilitated bioproduct recovery.

The biocatalyst, being highly hydrated is a significant distributor of light radiation to photosynthetic microorganisms retained in the interior of the biocatalyst and also serves to protect the microorganism from photorespiration. The solid debris in the culture liquid (an aqueous solution comprising nutrients for metabolic processes) can be materially reduced, if not essentially eliminated, due to the microorganisms being irreversibly retained in the biocatalyst. Thus the turbidity is reduced and a given light intensity can thus be found at a greater depth in the culture liquid. These advantages provided by the biocatalysts of this invention can be realized in any photosynthetic process regardless of whether or not a phosphorescent material is used.

Examples of phosphorescent materials include, but are not limited to, phosphorescent materials are metal sulfide phosphors such as ZnCdS:Cu:Al, ZnCdS:Ag:Al, ZnS:Ag:Al, ZnS:Cu:Al as described in U.S. Pat. No. 3,595,804 and metal sulfides that are co-activated with rare earth elements such as those describe in U.S. Pat. No. 3,957,678. Phosphors that are higher in luminous intensity and longer in luminous persistence than the metal sulfide pigments include compositions comprising a host material that is generally an alkaline earth aluminate, or an alkaline earth silicate. The host materials generally comprise Europium as an activator and often comprise one or more co-activators such as elements of the Lanthanide series (e.g. lanthanum, cerium, praseodymium, neodymium, samarium, gadolinium, terbium, dysprosium, holmium, erbium, thulium, ytterbium, and lutetium), tin, manganese, yttrium, or bismuth. Examples of such phosphors are described in U.S. Pat. No. 5,424,006.

High emission intensity and persistence phosphorescent materials can be alkaline earth aluminate oxides having the formula $MO_mAl_2O_3:Eu^{2+}$, $R^{3+}$ wherein m is a number ranging from 1.6 to about 2.2, M is an alkaline earth metal (strontium, calcium or barium), $Eu^{2+}$ is an activator, and R is one or more trivalent rare earth materials of the lanthanide series (e.g. lanthanum, cerium, praseodymium, neodymium, samarium, gadolinium, terbium, dysprosium, holmium, erbium, thulium, ytterbium, lutetium), yttrium or bismuth co-activators. Examples of such phosphors are described in U.S. Pat. No. 6,117,362. Phosphorescent materials also include alkaline earth aluminate oxides having the formula $M_kAl_2O_4:2xEu^{2+}, 2yR^{3+}$ wherein k=1−2x−2y, x is a number ranging from about 0.0001 to about 0.05, y is a number ranging from about x to 3x, M is an alkaline earth metal (strontium, calcium or barium), $Eu^{2+}$ is an activator, and R is one or more trivalent rare earth materials (e.g. lanthanum, cerium, praseodymium, neodymium, samarium, gadolinium, terbium, dysprosium, holmium, erbium, thulium, ytterbium, lutetium), yttrium or bismuth co-activators. See U.S. Pat. No. 6,267,911B1.

Phosphorescent materials also include those in which a portion of the $Al^{3+}$ in the host matrix is replaced with divalent ions such as $Mg^{2+}$ or $Zn^{2+}$ and those in which the alkaline earth metal ion ($M^{2+}$) is replaced with a monovalent alkali metal ion such as $Li^+$, $Na^+$, $K^+$, $Cs^+$ or $Rb^+$ such as described in U.S. Pat. Nos. 6,117,362 and 6,267,911B1.

High intensity and high persistence silicates have been disclosed in U.S. Pat. No. 5,839,718, such as Sr.BaO.Mg-.MO.SiGe:Eu:Ln wherein M is beryllium, zinc or cadmium and Ln is chosen from the group consisting of the rare earth materials, the group 3A elements, scandium, titanium, vanadium, chromium, manganese, yttrium, zirconium, niobium, molybdenum, hafnium, tantalum, tungsten, indium, thallium, phosphorous, arsenic, antimony, bismuth, tin, and lead. Particularly useful are dysprosium, neodymium, thulium, tin, indium, and bismuth. X in these compounds is at least one halide atom.

Other phosphorescent materials include alkaline earth aluminates of the formula $MO.Al_2O_3.B_2O_3:R$ wherein M is a combination of more than one alkaline earth metal (strontium, calcium or barium or combinations thereof) and R is a combination of $Eu^{2+}$ activator, and at least one trivalent rare earth material co-activator, (e.g. lanthanum, cerium, praseodymium, neodymium, samarium, gadolinium, terbium, dysprosium, holmium, erbium, thulium, ytterbium, lutetium), bismuth or manganese. Examples of such phosphors can be found in U.S. Pat. No. 5,885,483. Alkaline earth aluminates of the type $MAl_2O_4$, which are described in U.S. Pat. No. 5,424,006, may also find application as may phosphorescent materials comprising a donor system and an acceptor system such as described in U.S. Pat. No. 6,953,536 B2.

As can be appreciated, many other phosphors can find application. See, for instance, Yen and Weber, Inorganic Phosphors: Compositions, Preparation and Optical Properties, CRC Press, 2004.

The phosphorescent material may be a discrete particle or may be a particle having a coating to facilitate incorporation and retention in the polymer forming the matrix. The particles may be of any suitable shape. Generally the maximum dimension of the of the particles is less than about 1 millimeter, preferably less than about 0.1 millimeter. The particles may be nanoparticles.

The persistence time exhibited by the phosphorescent materials can range from a short duration, e.g., about 5 to 10 seconds, to as much as 10 or 20 hours or more and will be dependent upon the phosphorescent material used. Preferred phosphorescent materials exhibit a persistence of at least about one minute. The intensity of the emitted radiation will, in part, depend upon the concentration of the phosphorescent material in the biocatalyst and the nature of the phosphorescent material. Typically the phosphorescent material is provided in an amount of at least about 0.1, say, between 0.2 and 5 or 10, mass percent of the polymer (non-hydrated) in the biocatalyst. One or more phosphorescent materials may be used in the biocatalyst. Where more than one phosphorescent material are used, the combination may be selected to provide one or more of wave shifting from different light wavelengths contained in the band width of the radiation source and providing differing persistence times. In preferred embodiments the phosphorescent materials are in the form of nanoparticles, e.g., having a major dimension of between about 10 nm and 10 µm. In some instances, it may be desired to coat the phosphorescent materials with a compatibilizing agent to facilitate incorporation of the phosphorescent material within the polymer. Compatibilizing agents include, but are not limited to, molecules having one or more of hydroxyl, thiol, silyl, carboxyl, or phosphoryl groups.

Enzyme-Containing Biocatalysts

In another aspect, the biocatalysts can contain, in addition to the microorganisms, one or more isolated enzymes in the interior of the biocatalyst to cause a catalytic change to a component which may be substrate or other nutrients, or a bioproduct or by-product or co-product of the microorganisms, or may be a toxin, phage or the like. Typically extracellular enzymes bond or adhere to solid surfaces, such as the hydrophilic polymer, solid additives, cell walls and extracellular polymeric substance. It is understood that isolated enzymes may also be located within the cell of a microorganism. Hence, the enzymes can be substantially irreversibly retained in the interior of the biocatalyst. Due to the structure of the biocatalysts of this invention, the microorganisms and the enzymes can be in close proximity and thus effective, cooperative bioconversions can be obtained. The association of the enzymes with the interior surfaces of the biocatalyst typically increases the resistance of the enzyme or enzymes to denaturation due to changes in temperature, pH, or other factors related to thermal or operational stability of the enzymes. Also, by being retained in the biocatalyst, the use of the enzyme in a bioreactor is facilitated and undesirable post-reactions can be mitigated.

Examples of enzymes include, but are not limited to, one or more of oxidoreductases, transferases, hydrolases, lyases, isomerases, and ligases. The enzymes may cause one or more metabolic conversions. For instance, an enzyme may metabolize a component in the feed to provide an intermediate for use by the microorganisms in the biocatalyst. An enzyme may be used to metabolize a metabolite of the microorganism to provide a sought bioproduct. An enzyme may be used to metabolize a component in the feed or a co-metabolite from the microorganism that may be adverse to the microorganism into a metabolite that is less adverse to the microorganism. If desired, two or more different enzymes can be used to effect a series of metabolic conversions on a component in the feed or a metabolite from the microorganism.

Representative enzymes include, without limitation: cellulase, cellobiohydrolase (e.g., CBHI, CBHII), alcohol dehydrogenase (A, B, and C), acetaldehyde dehydrogenase, amylase, alpha amylase, glucoamylase, beta glucanase, beta glucosidase, invertase, endoglucanase (e.g., EGI, EGII, EGIII), lactase, hemicellulase, pectinase, hydrogenase, pullulanase, phytase, a hydrolase, a lipase, polysaccharase, ligninase, Accellerase® 1000, Accellerase® 1500, Accellerase® DUET, Accellerase® TRIO, or Cellic CTec2 enzymes, phosphoglucose isomerase, inositol-1-phosphate synthase, inositol monophosphatase, myo-inositol dehydrogenase, myo-inosose-2-dehydratase, inositol 2-dehydrogenase, deoxy-D-gluconate isomerase, kinase, 5-dehydro-2-deoxygluconokinase, deoxyphophogluconate aldolase, 3-hydroxy acid dehydrogenase, isomerase, topoisomerase, dehydratase, monosaccharide dehydrogenase, aldolase, phosphatase, a protease, DNase, alginate lyase, laminarinase, endoglucanase, L-butanediol dehydrogenase, acetoin reductase, 3-hydroxyacyl-CoA dehydrogenase, or cis-aconitate decarboxylase. The enzymes include those described by Heinzelman et al. (2009) $PNAS$ 106: 5610-5615, herein incorporated by reference in its entirety.

The enzymes may be bound to the precursor for the hydrophilic polymer of the biocatalyst prior to the formation of the biocatalyst or may be introduced during the preparation of the biocatalyst, e.g., by addition to the liquid medium for forming the biocatalyst. There are many methods that would be known to one of skill in the art for providing enzymes or fragments thereof, or nucleic acids, onto a solid support. Some examples of such methods include, e.g., electrostatic droplet generation, electrochemical means, via adsorption, via covalent binding, via cross-linking, via a chemical reaction or process. Various methods are described in Methods in Enzymology, Immobilized Enzymes and Cells, Part C. 1987. Academic Press. Edited by S. P. Colowick and N. O. Kaplan. Volume 136; Immobilization of Enzymes and Cells. 1997. Humana Press. Edited by G. F. Bickerstaff. Series: Methods in Biotechnology, Edited by J. M. Walker; DiCosimo, R., McAuliffe, J., Poulose, A. J. Bohlmann, G. 2012. Industrial use of immobilized enzymes. Chem. Soc. Rev.; and Immobilized Enzymes: Methods and Applications. Wilhelm Tischer and Frank Wedekind, Topics in Current Chemistry, Vol. 200. Page 95-126.

C. Methods for Making Biocatalysts

The components, including microorganisms, used to make the biocatalysts and the process conditions used for the preparation of the biocatalysts are not critical to the broad aspects of this invention and may vary widely as is well understood in the art once understanding the principles of metabolically retaining microorganisms described above. In any event, the components and process conditions for making the biocatalysts with the irreversibly, metabolically retained microorganisms should not unduly adversely affect the microorganisms.

The biocatalysts may be prepared from a liquid medium containing the microorganism and solubilized precursor for the hydrophilic polymer which may be one or more of a polymerizable or solidifiable component or a solid that is fusible or bondable to form the matrix. Aqueous media are most often used due to the compatibility of most microorganisms and enzymes with water. However, with microorganisms that tolerate other liquids, such liquids can be used to make all or a portion of the liquid medium. Examples of such other liquids include, but are not limited to liquid hydrocarbons, peroxygenated liquids, liquid carboxy-containing compounds, and the like. Mixed liquid media can also be used to prepare the biocatalyst. The mixed media may comprise miscible or immiscible liquid phases. For instance, the microorganism may be suspended in a dispersed, aqueous phase and the polymerizable or solidifiable component may be contained in a continuous solvent phase.

The liquid medium used to prepare the biocatalyst may contain more than one type of microorganism, especially where the microorganisms do not significantly compete for the same substrate, and may contain one or more isolated enzymes or functional additives such as polysaccharide, solid sorbent and phosphorescent materials, as described above. Preferably, the biocatalysts contain a single type of microorganism. The concentration of the microorganisms in the liquid medium used to make the biocatalysts should at least be about 60 grams per liter. As discussed above, the concentration of microorganisms should preferably approximate the sought density of microorganisms in the biocatalyst. The relative amounts of microorganism and polymeric material in forming the biocatalyst can vary widely. The growth of the population of microorganisms post formation of the biocatalyst is contemplated as well as the potential for damage to some of the population of microorganisms during the biocatalyst-forming process. Nevertheless, higher microorganism concentrations are generally preferred, e.g., at least about 100 grams per liter, preferably at least about 200, and often between about 250 and 750, grams per liter of the liquid medium used to make the biocatalysts.

Any suitable process may be used to solidify or polymerize the polymeric material or to adhere or fuse particles to form the open, porous polymeric matrix with microorganism irreversibly retained therein. The conditions of suitable processes should not unduly adversely affect the microorganisms. As microorganisms differ in tolerance to temperatures, pressures and the presence of other chemicals, some matrix-forming processes may be more advantageous for one type of microorganism than for another type of microorganism.

Preferably the polymeric matrix is formed from solidification of a high molecular weight material, by polymerization or by cross-linking of prepolymer in manner that a population of microorganisms is provided in the interior of the biocatalyst as it is being formed. Exemplary processes include solution polymerization, slurry polymerization (characterized by having two or more initial phases), and solidification by cooling or removal of solvent.

The biocatalysts may be formed in situ in the liquid medium by subjecting the medium to solidification conditions (such as cooling or evaporation) or adding a component to cause a polymerization or cross-linking or agglomeration of solids to occur to form a solid structure such as a catalyst, cross-linking agent or coagulating agent. Alternatively, the liquid medium may be extruded into a solution containing a solidification agent such as a catalyst, cross-linking or coagulating agent or coated onto a substrate and then the composite subjected to conditions to form the solid biocatalyst.

Polymeric materials used to make the biocatalysts may have an organic or inorganic backbone but have sufficient hydrophilic moieties to provide a highly hydrophilic polymer which when incorporated into the matrices exhibits sufficient water sorption properties to provide the sought Hydration Expansion Volume of the biocatalyst. Polymeric materials are also intended to include high molecular weight substances such as waxes (whether or not prepared by a polymerization process), oligomers and the like so long as they form biocatalysts that remain solid under the conditions of the bioconversion process intended for their use and have sufficient hydrophilic properties that the Hydration Expansion Volume can be achieved. As stated above, it is not essential that polymeric materials become cross-linked or further polymerized in forming the polymeric matrix.

Examples of polymeric materials include homopolymers and copolymers which may or may not be cross-linked and include condensation and addition polymers that provide high hydrophilicity and enable the Hydration Expansion Volumes to be obtained. The polymer may be a homopolymer or a copolymer, say, of a hydrophilic moiety and a more hydrophobic moiety. The molecular weight and molecular weight distribution are preferably selected to provide the combination of hydrophilicity and strength as is known in the art. The polymers may be functionalized with hydrophilic moieties to enhance hydrophilicity. Examples of hydrophilic moieties include, but are not limited to hydroxyl, alkoxyl, acyl, carboxyl, amido, and oxyanions of one or more of titanium, molybdenum, phosphorus, sulfur and nitrogen such as phosphates, phosphonates, sulfates, sulfonates, and nitrates, and the hydrophilic moieties may be further substituted with hydrophilic moieties such as hydroxyalkoxides, acetylacetonate, and the like. Typically the polymers contain carbonyl and hydroxyl groups, especially at some adjacent hydrophilic moieties such as glycol moieties. In some instances, the backbone of the polymer contains ether oxygens to enhance hydrophilicity. In some instances, the atomic ratio of oxygen to carbon in the polymer is between about 0.3:1 to 5:1.

Polymers which may find use in forming the matrices include functionalized or non-functionalized polyacrylamides, polyvinyl alcohols, polyetherketones, polyurethanes, polycarbonates, polysulfones, polysulfides, polysilicones, olefinic polymers such as polyethylene, polypropylene, polybutadiene, rubbers, and polystyrene, nylons, polythyloxazyoline, polyethylene glycol, polysaccharides such as sodium alginate, carageenan, agar, hyaluronic acid, chondroitin sulfate, dextran, dextran sulfate, heparin, heparin sulfate, heparan sulfate, chitosan, gellan gum, xanthan gum, guar gum, water soluble cellulose derivatives and carrageenan, and proteins such as gelatin, collagen and albumin, which may be polymers, prepolymers or oligomers, and polymers and copolymers from the following monomers, oligomers and prepolymers: monomethacrylates such as polyethylene glycol monomethacrylate, polypropylene glycol monomethacrylate, polypropylene glycol monomethacrylate, methoxydiethylene glycol methacrylate, methoxypolyethylene glycol methacrylate, methacryloyloxyethyl hydrogen phthalate, methacryloyloxyethyl hydrogen succinate, 3-chloro-2-hydroxypropyl methacrylate, stearyl methacrylate, 2-hydroxy methacrylate, and ethyl methacrylate; monoacrylates such as 2-hydroxyethyl acrylate, 2-hydroxypropyl acrylate, isobutyl acrylate, t-butyl acrylate, isooctyl acrylate, lauryl acrylate, stearyl acrylate, isobornyl acrylate, cyclohexyl acrylate, methoxytriethylene glycol acrylate, 2-ethoxyethyl acrylate, tetrahydrofurfuryl acrylate, phenoxyethyl acrylate, nonylphenoxypolyethylene glycol acrylate, nonylphenoxypolypropylene glycol acrylate, silicon-modified acrylate, polypropylene glycol monoacrylate, phenoxyethyl acrylate, phenoxydiethylene glycol acrylate, phenoxypolyethylene glycol acrylate, methoxypolyethylene glycol acrylate, acryloyloxyethyl hydrogen succinate, and lauryl acrylate; dimethacrylates such as 1,3-butylene glycol dimethacrylate, 1,4-butanediol dimethacrylate, ethylene glycol dimethacrylate, diethylene glycol dimethacrylate, triethylene glycol dimethacrylate, polyethylene glycol dimethacrylate, butylene glycol dimethacrylate, hexanediol dimethacrylate, neopentyl glycol dimethacrylate, polyprene glycol dimethacrylate, 2-hydroxy-1,3-dimethacryloxypropane, 2,2-bis-4-methacryloxyethoxyphenylpropane, 3,2-bis-4-methacryloxydiethoxyphenylpropane, and 2,2-bis-4-methacryloxypolyethoxyphenylpropane;

diacrylates such as ethoxylated neopentyl glycol diacrylate, polyethylene glycol diacrylate, 1,6-hexanediol diacrylate, neopentyl glycol diacrylate, tripropylene glycol diacrylate, polypropylene glycol diacrylate, 2,2-bis-4-acryloxyethoxyphenylpropane, 2-hydroxy-1-acryloxy-3-methacryloxypropane; trimethacrylates such as trimethylolpropane trimethacrylate; triacrylates such as trimethylolpropane triacrylate, pentaerythritol triacrylate, trimethylolpropane EO-added triacrylate, glycerol PO-added triacrylate, and ethoxylated trimethylolpropane triacrylate; tetraacrylates such as pentaerythritol tetraacrylate, ethoxylated pentaerythritol tetraacrylate, propoxylated pentaerythritol tetraacrylate, and ditrimethylolpropane tetraacrylate;

urethane acrylates such as urethane acrylate, urethane dimethyl acrylate, and urethane trimethyl acrylate;

amino-containing moieties such as 2-aminoethyl acrylate, 2-aminoethyl methacrylate, aminoethyl methacrylate, dimethyl aminoethyl methacrylate, monomethyl aminoethyl methacrylate, t-butylaminoethylmethacrylate, p-aminostyrene, o-aminostyrene, 2-amino-4-vinyltoluene, dimethylaminoethyl acrylate, diethylaminoethyl acrylate, piperidinoethyl ethyl acrylate, piperidinoethyl methacrylate, morpholinoethyl acrylate, morpholinoethyl methacrylate, 2-vinyl pyridine, 3-vinyl pyridine, 2-ethyl-5-vinyl pyridine, dimethylaminopropylethyl acrylate, dimethylaminopropylethyl methacrylate, 2-vinyl pyrrolidone, 3-vinyl pyrrolidone, dimethylaminoethyl vinyl ether, dimethylaminoethyl vinyl sulfide, diethylaminoethyl vinyl ether, 2-pyrrolidinoethyl acrylate, 2-pyrrolidinoethyl methacrylate, and other monomers such as acrylamide, acrylic acid, and dimethylacrylamide.

Not all the above listed polymers will be useful by themselves, but may be required to be functionalized or used to form a co-polymer with a highly hydrophilic polymer.

Cross linking agents, accelerators, polymerization catalysts, and other polymerization additives may be employed such as triethanolamine, triethylamine, ethanolamine, N-methyl diethanolamine, N,N-dimethyl benzylamine, dibenzyl amino, N-benzyl ethanolamine, N-isopropyl benzylamino, tetramethyl ethylenediamine, potassium persulfate, tetramethyl ethylenediamine, lysine, ornithine, histidine, arginine, N-vinyl pyrrolidinone, 2-vinyl pyridine, 1-vinyl imidazole, 9-vinyl carbazone, acrylic acid, and 2-allyl-2-methyl-1,3-cyclopentane dione. For polyvinyl alcohol polymers and copolymers, boric acid and phosphoric acid may be used in the preparation of polymeric matrices. As stated above, the amount of cross-linking agent may need to be limited to assure that the matrices retain high hydrophilicity and the ability to have a high Hydration Expansion Volume. The selection of the polymer and cross-linking agents and other additives to make porous matrices having the physical properties set forth above is within the level of the artisan in the art of water soluble and highly hydrophilic polymer synthesis.

The biocatalysts may be formed in the presence of other additives which may serve to enhance structural integrity or provide a beneficial activity for the microorganism such as attracting or sequestering components, providing nutrients, and the like. Additives can also be used to provide, for instance, a suitable density to be suspended in the aqueous medium rather than tending to float or sink in the broth. Typical additives include, but are not limited to, starch, glycogen, cellulose, lignin, chitin, collagen, keratin, clay, alumina, aluminosilicates, silica, aluminum phosphate, diatomaceous earth, carbon, polymer, polysaccharide and the like. These additives can be in the form of solids when the polymeric matrices are formed, and if so, are often in the range of about 0.01 to 100 microns in major dimension.

If desired, the microorganisms may be subjected to stress as is known in the art. Stress may be one or more of starvation, chemical or physical conditions. Chemical stresses include toxins, antimicrobial agents, and inhibitory concentrations of compounds. Physical stresses include light intensity, UV light, temperature, mechanical agitation, pressure or compression, and desiccation or osmotic pressure. The stress may produce regulated biological reactions that protect the microorganisms from shock and the stress may allow the hardier microorganisms to survive while the weaker cells die.

Microorganisms

The microorganisms may be unicellular or may be multicellular that behaves as a single cell microorganism such as filamentous growth microorganisms and budding growth microorganisms. Often the cells of multicellular microorganisms have the capability to exist singularly. The microorganisms can be of any type, including, but not limited to, those microorganisms that are aerobes, anaerobes, facultative anaerobes, heterotrophs, autotrophs, photoautotrophs, photoheterotrophs, chemoautotrophs, and/or chemoheterotrophs. The cellular activity, including cell growth can be aerobic, microaerophilic, or anaerobic. The cells can be in any phase of growth, including lag (or conduction), exponential, transition, stationary, death, dormant, vegetative, sporulating, etc. The one or more microorganisms be a psychrophile (optimal growth at −10° C. to 25° C.), a mesophile (optimal growth at 20-50° C.), a thermophile (optimal growth 45° C. to 80° C.), or a hyperthermophile (optimal growth at 80° C. to 100° C.). The one or more microorganisms can be a gram-negative or gram-positive bacterium. A bacterium can be a cocci (spherical), bacilli (rod-like), or spirilla (spiral-shaped; e.g., vibrios or comma bacteria). The microorganisms can be phenotypically and genotypically diverse.

The microorganisms can be a wild-type (naturally occurring) microorganism or a recombinant microorganism (including, but not limited to genetically engineered microorganisms). A recombinant microorganism can comprise one or more heterologous nucleic acid sequences (e.g., genes). One or more genes can be introduced into a microorganism used in the methods, compositions, or kits described herein, e.g., by homologous recombination. One or more genes can be introduction into a microorganism with, e.g., a vector. The one or more microorganisms can comprise one or more vectors. A vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain a means for self-replication. The vector can, when introduced into a host cell, integrate into the genome of the host cell and replicate together with the one or more chromosomes into which it has been integrated. Such a vector can comprise specific sequences that can allow recombination into a particular, desired site of the host chromosome. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. The vector can include a reporter gene, such as a green fluorescent protein (GFP), which can be either fused in frame to one or more of the encoded polypeptides, or expressed separately. The vector can also include a selection marker such as an antibiotic resistance gene that can be used for selection of suitable transformants. Means of genetically manipulating organisms are described, e.g., Current Protocols in Molecular Biology, last updated Jul. 25, 2011, Wiley, Print ISSN: 1934-3639. In some embodiments, one or more genes involved in byproduct formation are deleted in a microorganism. In some embodiments, one or more genes involved in byproduct formation are not deleted. Nucleic acid introduced into a microorganism can be codon-optimized for the microorganism. A gene can be modified (e.g., mutated) to increase the activity of the resulting gene product (e.g., enzyme). Sought properties in wild-type or genetically modified microorganisms can often be enhanced through a natural modification process, or self-engineering process, involving multigenerational selective harvesting to obtain strain improvements such as microorganisms that exhibit enhanced properties such as robustness in an environment or bioactivity. See, for instance, Ben-Jacob, et al., Self-engineering capabilities of bacteria, J. R. Soc. Interface 2006, 3, doi: 10.1098/rsif.2005.0089, 22 Feb. 2006.

The selected microorganism to be used in a biocatalyst can be targeted to the sought activity. The biocatalysts thus often contain substantially pure strain types of microorganisms and, because of the targeting, enable high bioactivity to be achieved and provide a stable population of the microorganism in the biocatalyst.

Representative microorganisms for making biocatalysts of this invention include, without limitation, those set forth in United States published patent application nos. 2011/0072714, especially paragraph 0122; 2010/0279354, especially paragraphs 0083 through 0089; 2011/0185017, especially paragraph 0046; 2009/0155873; especially paragraph 0093; and 20060063217, especially paragraphs 0030 and 0031, and those set forth in Appendix A hereto.

Photosynthetic microorganisms include bacteria, algae, and molds having biocatalytic activity activated by light radiation. Examples of photosynthetic microorganisms for higher oxygenated organic compound production include, but are not limited to alga such as Bacillariophyceae strains, *Chlorophyceae, Cyanophyceae, Xanthophyceaei, Chrysophyceae, Chlorella* (e.g., *Chlorella protothecoides*), *Crypthecodinium, Schizocytrium, Nannochloropsis, Ulkenia, Dunaliella, Cyclotella, Navicula, Nitzschia, Cyclotella, Phaeodactylum*, and *Thaustochytrids*; yeasts such as *Rhodotorula, Saccharomyces*, and *Apiotrichum* strains; and fungi species such as the *Mortierella* strain. Genetically enhanced photoautotrophic cyanobacteria, algae, and other photoautotrophic organisms have been adapted to bioconvert carbohydrates internal to the microorganism directly to ethanol, butanol, pentanol and other higher alcohols and other biofuels. For example, genetically modified cyanobacteria having constructs comprising DNA fragments encoding pyruvate decarboxylase (pdc) and alcohol dehydrogenase (adh) enzymes are described in U.S. Pat. No. 6,699, 696. Cyanobacteria are photosynthetic bacteria which use light, inorganic elements, water, and a carbon source, generally carbon dioxide, to metabolize and grow. The production of ethanol using genetically engineered cyanobacteria has also been described in PCT Published Patent Application WO 2007/084477.

The following examples are provided in illustration of the biocatalysts and processes for making the biocatalysts and are not in limitation. All parts and percentages of solids are by mass and of liquids and gases are by volume unless otherwise stated or is clear from the context.

In these examples, the following general procedure is used. The microorganisms for the biocatalyst are grown under suitable planktonic conditions in an aqueous medium for the microorganisms including the presence of nutrients and micronutrients. This medium is referred to herein as the "Culture Medium". The microorganisms used are as available and thus may be either substantially pure strains or mixed cultures. The cell density in the Culture Medium is determined by optical density. If the cell density of the Culture Medium is below that sought to make the biocatalyst, the Culture Medium is centrifuged or filtered to provide a denser, cell-containing fraction. A separately prepared aqueous solution of solubilized precursor is made (referred to herein as the "Polymer Solution"). Any solid additive for the biocatalysts is added to the Polymer Solution in amounts that will provide the sought amount in the biocatalyst. The Polymer Solution is mixed with a mechanical stirrer to assure uniform dispersion of the components in the aqueous medium. Where necessary to solubilize the precursor, the Polymer Solution can be heated as appropriate. In some instances, a micronutrient solution is also added to the Polymer Solution.

Aliquots of each of the Culture Medium (or dense phase from centrifugation) and Polymer Solution are admixed under mechanical stirring at about 30° C. to for a Precursor Solution. Where the microorganism is anaerobic, the Culture Medium and the mixing of the Culture Medium and Polymer Solution and all subsequent steps are maintained under anaerobic conditions by purging with nitrogen.

The Precursor Solution is then extruded through a perforated plate having orifices of about 0.75 millimeter in diameter to form droplets of about 3 millimeters in diameter. The droplets fall into a gently stirred coagulating bath of an aqueous boric acid solution having a pH of about 5. The biocatalyst is recovered from the coagulating bath and washed with distilled water. The biocatalyst, after washing, is placed in a liquid medium containing micronutrients and the substrate under suitable metabolic conditions for the microorganisms.

Table I summarizes the examples. Table II sets forth the microorganisms used in the examples. Table III sets forth the hydrophilic polymer(s) that is used in the examples. Table IV sets forth the solid additive packages used in the examples.

TABLE I

| Example | Polymer Solution | Volume parts Polymer Solution per 100 parts of Precursor Solution | Microorganism | Microorganism culture density wet weight g/L | Volume parts Microorganism culture per 100 parts of Precursor Solution | Solid Additive Package | Mass parts of Solid Additive package per liter of Precursor Solution |
|---|---|---|---|---|---|---|---|
| 1 | A | 80 | M-1 | 620 | 20 | S-1 | 1 |
| 2 | Y | 72 | M-13 | 375 | 28 | N/A | N/A |
| 3 | DD | 78 | M-52 | 280 | 22 | S-13 | 13 |
| 4 | U | 65 | M-15 | 300 | 35 | S-25 | 0.2 |
| 5 | BBB | 73 | M-27 | 440 | 27 | N/A | N/A |
| 6 | D | 75 | M-16 | 685 | 25 | S-14 | 2.2 |
| 7 | R | 69 | M-35 | 250 | 31 | S-1 | 0.9 |
| 8 | OOO | 90 | M-21 | 700 | 10 | S-23 | 5.5 |
| 9 | MM | 45 | M-1 | 80 | 55 | S-13 | 10 |
| 10 | KKK | 50 | M-36 | 95 | 50 | S-27 | 0.1 |
| 11 | V | 73 | M-52 | 185 | 27 | N/A | N/A |
| 12 | III | 66 | M-19 | 270 | 34 | S-20 | 0.1 |
| 13 | N | 40 | M-19 | 110 | 60 | N/A | N/A |
| 14 | A | 80 | M-38 | 400 | 20 | S-25 | 0.5 |
| 15 | SSS | 88 | M-2 | 650 | 12 | S-20 | 0.1 |
| 16 | C | 73 | M-6 | 310 | 27 | N/A | N/A |
| 17 | Z | 60 | M-40 | 250 | 40 | S-6 | 1.2 |
| 18 | XXX | 73 | M-35 | 400 | 27 | S-7 | 0.5 |
| 19 | CCC | 65 | M-38 | 265 | 35 | S-8 | 0.8 |
| 20 | VVV | 70 | M-53 | 355 | 30 | S-6 | 1.2 |
| 21 | MMM | 78 | M-2 | 675 | 22 | N/A | N/A |
| 22 | NNN | 74 | M-53 | 305 | 26 | S-6 | 0.5 |
| 23 | C | 75 | M-38 | 365 | 25 | S-8 | 0.8 |
| 24 | EE | 83 | M-19 | 650 | 17 | N/A | N/A |
| 25 | H | 70 | M-4 | 310 | 30 | N/A | N/A |
| 26 | YY | 84 | M-52 | 630 | 16 | S-13 | 9.0 |
| 27 | QQQ | 90 | M-20 | 715 | 10 | N/A | N/A |
| 28 | P | 65 | M-51 | 210 | 35 | N/A | N/A |
| 29 | JJJ | 58 | M-26 | 205 | 42 | S-13 | 3.5 |
| 30 | KKK | 48 | M-35 | 180 | 52 | S-24 | 0.3 |
| 31 | V | 70 | M-38 | 460 | 30 | S-13 | 0.5 |
| 32 | KK | 66 | M-18 | 380 | 34 | S-19 | 2.2 |
| 33 | Z | 62 | M-52 | 365 | 38 | S-13 | 2.5 |
| 34 | F | 62 | M-22 | 355 | 38 | S-3 | 0.4 |
| 35 | CCC | 66 | M-6 | 455 | 34 | S-6 | 0.55 |
| 36 | H | 68 | M-6 | 410 | 32 | S-25 | 2.5 |
| 37 | QQ | 50 | M-42 | 240 | 50 | S-25 | 2.5 |
| 38 | X | 71 | M-48 | 420 | 29 | S-11 | 0.01 |
| 39 | M | 72 | M-53 | 415 | 28 | S-21 | 1.0 |
| 40 | RRR | 85 | M-1 | 670 | 15 | S-23 | 1.0 |
| 41 | T | 76 | M-19 | 330 | 24 | S-22 | 0.5 |

TABLE I-continued

| Example | Polymer Solution | Volume parts Polymer Solution per 100 parts of Precursor Solution | Microorganism | Microorganism culture density wet weight g/L | Volume parts Microorganism culture per 100 parts of Precursor Solution | Solid Additive Package | Mass parts of Solid Additive package per liter of Precursor Solution |
|---|---|---|---|---|---|---|---|
| 42 | E | 72 | M-16 | 320 | 28 | N/A | N/A |
| 43 | KKK | 50 | M-48 | 100 | 50 | N/A | N/A |
| 44 | M | 74 | M-17 | 400 | 26 | S-23 | 1.0 |
| 45 | FF | 81 | M-26 | 565 | 19 | S-3 | 0.65 |
| 46 | RRR | 85 | M-47 | 595 | 15 | S-3 | 0.92 |
| 47 | YYY | 55 | M-13 | 115 | 45 | S-26 | 1.0 |
| 48 | QQ | 40 | M-41 | 65 | 60 | S-13 | 0.7 |
| 49 | SSS | 88 | M-35 | 660 | 12 | S-26 | 0.1 |
| 50 | C | 76 | M-36 | 540 | 24 | N/A | N/A |
| 51 | H | 68 | M-42 | 460 | 32 | S-20 | 0.1 |
| 52 | TT | 84 | M-37 | 610 | 16 | S-13 | 10.0 |
| 53 | AAA | 75 | M-38 | 565 | 25 | S-1 | 1.5 |
| 54 | W | 50 | M-20 | 260 | 50 | S-14 | 2.5 |
| 55 | TTT | 74 | M-18 | 440 | 26 | S-20 | 0.2 |
| 56 | NNN | 78 | M-13 | 645 | 22 | N/A | N/A |
| 57 | GG | 58 | M-19 | 200 | 42 | S-14 | 2.5 |
| 58 | J | 81 | M-47 | 740 | 19 | S-12 | 0.4 |
| 59 | RR | 72 | M-53 | 575 | 28 | S-25 | 1.7 |
| 60 | PPP | 72 | M-28 | 570 | 28 | S-14 | 1.0 |
| 61 | G | 66 | M-6 | 320 | 34 | N/A | N/A |
| 62 | YY | 83 | M-28 | 730 | 17 | S-14 | 1.0 |
| 63 | O | 68 | M-22 | 365 | 32 | S-8 | 0.2 |
| 64 | HHH | 71 | M-3 | 420 | 29 | S-25 | 1.0 |
| 65 | D | 71 | M-53 | 485 | 29 | N/A | N/A |
| 66 | FF | 76 | M-25 | 580 | 24 | N/A | N/A |
| 67 | NN | 58 | M-15 | 280 | 42 | S-9 | 1.0 |
| 68 | JJJ | 65 | M-8 | 420 | 35 | S-1 | 1.0 |
| 69 | Q | 77 | M-5 | 560 | 23 | S-3 | 0.1 |
| 70 | PP | 70 | M-12 | 425 | 30 | S-6 | 7.0 |
| 71 | DDD | 89 | M-43 | 845 | 11 | S-23 | 2.0 |
| 72 | JJ | 75 | M-41 | 520 | 25 | S-26 | 0.5 |
| 73 | MMM | 85 | M-25 | 730 | 15 | N/A | N/A |
| 74 | N | 42 | M-8 | 115 | 58 | N/A | N/A |
| 75 | XXX | 75 | M-26 | 500 | 25 | S-23 | 1.0 |
| 76 | A | 82 | M-2 | 625 | 18 | S-21 | 1.0 |
| 77 | SSS | 88 | M-3 | 750 | 12 | S-10 | 1.0 |
| 78 | A | 79 | M-1 | 555 | 21 | S-4 | 0.17 |
| 79 | M | 72 | M-38 | 510 | 28 | S-13 | 7.5 |
| 80 | RRR | 75 | M-43 | 560 | 25 | S-13 | 2.0 |
| 81 | UUU | 60 | M-26 | 405 | 40 | S-15 | 1.0 |
| 82 | SS | 85 | M-49 | 770 | 15 | S-13 | 0.2 |
| 83 | VVV | 66 | M-9 | 390 | 34 | S-17 | 1.4 |
| 84 | YY | 80 | M-47 | 620 | 20 | S-11 | 0.05 |
| 85 | A | 81 | M-55 | 600 | 19 | S-24 | 0.17 |
| 86 | NN | 58 | M-16 | 210 | 42 | S-15 | 12.5 |
| 87 | NN | 58 | M-46 | 200 | 42 | S-1 | 0.5 |
| 88 | O | 71 | M-11 | 440 | 29 | S-16 | 2.0 |
| 89 | LLL | 85 | M-18 | 630 | 15 | S-6 | 0.17 |
| 90 | C | 72 | M-2 | 595 | 28 | S-12 | 1.0 |
| 91 | B | 68 | M-5 | 480 | 32 | S-7 | 2.0 |
| 92 | RR | 69 | M-54 | 485 | 31 | N/A | N/A |
| 93 | H | 80 | M-5 | 600 | 20 | N/A | N/A |
| 94 | ZZ | 77 | M-12 | 530 | 23 | S-6 | 1.6 |
| 95 | HH | 63 | M-6 | 490 | 37 | N/A | N/A |
| 96 | TTT | 75 | M-19 | 570 | 25 | N/A | N/A |
| 97 | I | 76 | M-19 | 550 | 24 | S-25 | 0.1 |
| 98 | Q | 77 | M-12 | 650 | 23 | N/A | N/A |
| 99 | GG | 59 | M-5 | 95 | 41 | S-4 | 0.32 |
| 100 | EE | 80 | M-53 | 740 | 20 | S-2 | 0.15 |
| 101 | V | 65 | M-37 | 300 | 35 | N/A | N/A |
| 102 | LL | 61 | M-28 | 280 | 39 | S-23 | 2.5 |
| 103 | S | 40 | M-20 | 70 | 60 | S-19 | 0.1 |
| 104 | B | 69 | M-2 | 540 | 31 | S-2 | 1.1 |
| 105 | G | 65 | M-34 | 355 | 35 | N/A | N/A |
| 106 | X | 72 | M-38 | 520 | 28 | S-13 | 6.2 |
| 107 | M | 65 | M-15 | 445 | 35 | S-21 | 1.5 |
| 108 | DDD | 90 | M-50 | 940 | 10 | N/A | N/A |
| 109 | A | 81 | M-50 | 725 | 19 | N/A | N/A |
| 110 | Z | 65 | M-22 | 300 | 35 | S-7 | 1.0 |
| 111 | OOO | 87 | M-43 | 755 | 13 | S-1 | 0.5 |
| 112 | L | 73 | M-26 | 585 | 27 | S-14 | 1.5 |
| 113 | RR | 76 | M-54 | 635 | 24 | S-5 | 0.1 |
| 114 | UU | 79 | M-34 | 765 | 21 | N/A | N/A |
| 115 | E | 72 | M-5 | 360 | 28 | S-25 | 0.1 |

TABLE I-continued

| Example | Polymer Solution | Volume parts Polymer Solution per 100 parts of Precursor Solution | Microorganism | Microorganism culture density wet weight g/L | Volume parts Microorganism culture per 100 parts of Precursor Solution | Solid Additive Package | Mass parts of Solid Additive package per liter of Precursor Solution |
|---|---|---|---|---|---|---|---|
| 116 | TTT | 71 | M-19 | 355 | 29 | S-6 | 0.14 |
| 117 | B | 70 | M-1 | 320 | 30 | S-6 | 0.14 |
| 118 | T | 79 | M-35 | 650 | 21 | S-23 | 6.5 |
| 119 | DD | 76 | M-39 | 525 | 24 | S-4 | 0.25 |
| 120 | F | 66 | M-4 | 395 | 34 | S-14 | 3.2 |
| 121 | OO | 68 | M-24 | 445 | 32 | S-2 | 1.2 |
| 122 | W | 51 | M-54 | 175 | 49 | S-15 | 14.0 |
| 123 | LLL | 80 | M-5 | 745 | 20 | S-6 | 0.8 |
| 124 | AAA | 75 | M-36 | 490 | 25 | S-9 | 0.6 |
| 125 | Y | 73 | M-12 | 480 | 27 | S-13 | 5.0 |
| 126 | QQ | 44 | M-19 | 200 | 56 | N/A | N/A |
| 127 | C | 72 | M-11 | 410 | 28 | N/A | N/A |
| 128 | K | 79 | M-1 | 580 | 21 | S-26 | 0.5 |
| 129 | MMM | 75 | M-12 | 460 | 25 | N/A | N/A |
| 130 | BB | 44 | M-34 | 125 | 56 | S-6 | 1.1 |
| 131 | M | 69 | M-23 | 580 | 31 | S-7 | 0.05 |
| 132 | EEE | 77 | M-29 | 680 | 23 | S-22 | 0.5 |
| 133 | A | 80 | M-3 | 770 | 20 | S-2 | 0.14 |
| 134 | O | 70 | M-40 | 655 | 30 | S-4 | 0.51 |
| 135 | PPP | 77 | M-2 | 700 | 23 | S-21 | 1.0 |
| 136 | AA | 88 | M-50 | 770 | 12 | S-27 | 0.1 |
| 137 | E | 73 | M-17 | 540 | 27 | N/A | N/A |
| 138 | MMM | 72 | M-44 | 600 | 28 | S-16 | 2.4 |
| 139 | W | 53 | M-7 | 240 | 47 | S-26 | 0.5 |
| 140 | II | 87 | M-45 | 725 | 13 | S-2 | 1.2 |
| 141 | B | 67 | M-1 | 410 | 33 | S-24 | 0.1 |
| 142 | UUU | 57 | M-35 | 320 | 43 | S-11 | 0.012 |
| 143 | D | 72 | M-51 | 510 | 28 | S-10 | 3.0 |
| 144 | AAA | 75 | M-30 | 590 | 25 | N/A | N/A |
| 145 | WWW | 75 | M-51 | 655 | 25 | N/A | N/A |
| 146 | OO | 75 | M-15 | 635 | 25 | N/A | N/A |
| 147 | I | 80 | M-4 | 810 | 20 | N/A | N/A |
| 148 | FFF | 72 | M-40 | 470 | 28 | S-13 | 6.2 |
| 149 | AA | 90 | M-1 | 940 | 10 | S-5 | 0.95 |
| 150 | B | 69 | M-35 | 455 | 31 | N/A | N/A |
| 151 | F | 62 | M-37 | 380 | 38 | S-7 | 0.8 |
| 152 | AAA | 75 | M-20 | 510 | 25 | N/A | N/A |
| 153 | J | 78 | M-13 | 665 | 22 | S-23 | 1.2 |
| 154 | N | 43 | M-33 | 175 | 57 | S-14 | 8.5 |
| 155 | K | 78 | M-20 | 560 | 22 | S-23 | 5.5 |
| 156 | D | 77 | M-23 | 690 | 23 | S-7 | 0.2 |
| 157 | S | 46 | M-4 | 90 | 54 | N/A | N/A |
| 158 | OO | 72 | M-45 | 540 | 28 | S-23 | 1.0 |
| 159 | C | 74 | M-31 | 560 | 26 | N/A | N/A |
| 160 | A | 82 | M-1 | 705 | 18 | S-15 | 5 |
| 161 | XXX | 75 | M-38 | 615 | 25 | S-8 | 0.35 |
| 162 | FFF | 73 | M-38 | 590 | 27 | S-5 | 2.0 |
| 163 | HH | 65 | M-1 | 470 | 35 | S-7 | 0.1 |
| 164 | T | 77 | M-2 | 660 | 23 | N/A | N/A |
| 165 | G | 62 | M-55 | 495 | 38 | S-7 | 0.5 |
| 166 | UUU | 67 | M-5 | 580 | 33 | S-23 | 1.0 |
| 167 | F | 55 | M-38 | 150 | 45 | S-8 | 0.1 |
| 168 | GG | 57 | M-55 | 190 | 43 | S-13 | 0.9 |
| 169 | F | 76 | M-40 | 580 | 24 | N/A | N/A |
| 170 | Y | 70 | M-51 | 450 | 30 | S-9 | 0.1 |
| 171 | K | 77 | M-14 | 575 | 23 | S-27 | 1.0 |
| 172 | E | 72 | M-39 | 480 | 28 | S-2 | 0.25 |
| 173 | H | 69 | M-51 | 490 | 31 | S-4 | 1.11 |
| 174 | BB | 45 | M-37 | 120 | 55 | S-11 | 0.5 |
| 175 | R | 70 | M-24 | 430 | 30 | S-2 | 0.2 |
| 176 | O | 72 | M-35 | 450 | 28 | S-8 | 0.25 |
| 177 | I | 78 | M-31 | 535 | 22 | S-7 | 0.14 |
| 178 | S | 42 | M-44 | 270 | 58 | S-18 | 1.4 |
| 179 | K | 77 | M-53 | 640 | 23 | S-23 | 2.2 |
| 180 | FF | 80 | M-29 | 710 | 20 | N/A | N/A |
| 181 | PP | 65 | M-24 | 360 | 35 | N/A | N/A |
| 182 | WWW | 74 | M-45 | 420 | 26 | N/A | N/A |
| 183 | B | 68 | M-51 | 390 | 32 | N/A | N/A |
| 184 | GGG | 62 | M-41 | 330 | 38 | S-14 | 7.5 |
| 185 | S | 44 | M-6 | 250 | 56 | S-3 | 0.84 |
| 186 | CC | 75 | M-41 | 555 | 25 | S-2 | 0.74 |
| 187 | UUU | 71 | M-9 | 460 | 29 | N/A | N/A |
| 188 | P | 64 | M-33 | 310 | 36 | S-5 | 2.0 |
| 189 | BBB | 73 | M-14 | 435 | 27 | N/A | N/A |

TABLE I-continued

| Example | Polymer Solution | Volume parts Polymer Solution per 100 parts of Precursor Solution | Microorganism | Microorganism culture density wet weight g/L | Volume parts Microorganism culture per 100 parts of Precursor Solution | Solid Additive Package | Mass parts of Solid Additive package per liter of Precursor Solution |
|---|---|---|---|---|---|---|---|
| 190 | XX | 92 | M-53 | 945 | 8 | S-23 | 1.2 |
| 191 | Z | 60 | M-7 | 420 | 40 | N/A | N/A |
| 192 | AAA | 75 | M-12 | 510 | 25 | N/A | N/A |
| 193 | L | 69 | M-24 | 455 | 31 | S-15 | 10.0 |
| 194 | H | 68 | M-32 | 505 | 32 | S-24 | 1.11 |
| 195 | D | 77 | M-15 | 630 | 23 | N/A | N/A |
| 196 | J | 75 | M-45 | 595 | 25 | S-16 | 4.0 |
| 197 | BBB | 74 | M-55 | 550 | 26 | S-12 | 0.58 |
| 198 | WW | 71 | M-10 | 550 | 29 | S-16 | 4.5 |
| 199 | HHH | 70 | M-4 | 555 | 30 | S-5 | 0.29 |
| 200 | QQ | 52 | M-7 | 250 | 48 | N/A | N/A |
| 201 | VVV | 64 | M-12 | 425 | 36 | S-19 | 1.0 |
| 202 | L | 70 | M-24 | 530 | 30 | S-15 | 1.0 |
| 203 | SS | 84 | M-13 | 735 | 16 | S-2 | 0.1 |
| 204 | MMM | 71 | M-12 | 500 | 29 | N/A | N/A |

TABLE II

| Microorganism Identifier | Microorganism |
|---|---|
| M-1 | *Saccharomyces cerevisiae* Sigma® YSC2™ |
| M-2 | *Zymomonas mobilis* ZM4 ATCC® 31821™ |
| M-3 | *Saccharomyces cerevisiae*, Fermentis Ethanol Red® |
| M-4 | *Saccharomyces cerevisiae* ATCC® 9763™ |
| M-5 | *Clostridium acetobutylicum* ATCC® 824™ |
| M-6 | *Clostridium pasteurianum* ATCC® 6013™ |
| M-7 | *Clostridium beijerinckii* ATCC® 10132™ |
| M-8 | *Clostridium butyricum* ATCC® 19398™ |
| M-9 | *Botryococcus braunii* UTEX 572™ |
| M-10 | *Botryococcus braunii* UTEX 2441™ |
| M-11 | *Botryococcus braunii* var. Showa UC Herbarium UC147504 |
| M-12 | *Nitrobacter winogradskyi* ATCC® 25391™ |
| M-13 | *Nitrosomonas europaea* ATCC® 19718™ |
| M-14 | *Nitrosomonas oceani* ATCC® 19707™ |
| M-15 | *Lactobacillus delbrueckii* ATCC® 9649™ |
| M-16 | *Lactobacillus casei* ATCC® 393™ |
| M-17 | *Lactococcus lactis* ssp. *lactis* ATCC® 19435™ |
| M-18 | *Lactobacillus amylovorus* ATCC® 33620™ |
| M-19 | *Enterobacter aerogenes* ATCC® 13048™ |
| M-20 | *Enterobacter cloacae* ATCC® 13047™ |
| M-21 | *Rhodobacter sphaeroides* ATCC® 17029™ |
| M-22 | *Pseudonocardia dioxanivarans* ATCC® 55486™ |
| M-23 | *Mycobacterium vaccae* ATCC® 15483™ |
| M-24 | *Anaerobiospirillum succiniciproducens* ATCC® 29305™ |
| M-25 | *Actinobacillus succinogenes* ATCC® 55618™ |
| M-26 | *Corynebacterium glutamicum* ATCC® 13032™ |
| M-27 | *Mannheimia succiniproducens* ATCC® 29305™ |
| M-28 | *Methanosarcina acetivorans* ATCC® 35395™ |
| M-29 | *Methanobrevibacter smithii* ATCC® 35061™ |
| M-30 | *Methanothermobacter thermautotrophicus* ATCC® 29096™ |
| M-31 | *Methanospirillum hungatei* ATCC® 27890™ |
| M-32 | *Methylosinus trichosporium* ATCC® 35070™ |
| M-33 | *Methylococcus capsulatus* ATCC® 19069™ |
| M-34 | *Pseudomonas syringae* ATCC® 19310™ |
| M-35 | *Pseudomonas* sp. ATCC® 13867™ |
| M-36 | *Achromobacter denitrificans* ATCC® 15173™ |
| M-37 | *Paracoccus denitrificans* ATCC® 17741™ |
| M-38 | *Dechloromonas agitata* ATCC® 700666™ |
| M-39 | *Decholormonas aromatica* ATCC® BAA-1848™ |
| M-40 | *Rhodococcus* sp. ATCC® 55309™ |
| M-41 | *Rhodococcus* sp. ATCC® 21504™ |
| M-42 | *Desulfovibrio desulfuricans* ATCC® 27774™ |
| M-43 | *Cyanothece* sp ATCC® 51142™ |
| M-44 | *Synechocystis* sp. ATCC® 27184™ |
| M-45 | *Chlamydomonas reinhardtii* ATCC® 30483™ |
| M-46 | *Bacillus amyloliquefaciens* ATCC® 23350™ |
| M-47 | *Citrobacter Freundii* ATCC® 8090™ |
| M-48 | *Klebsiella pneumonia* ATCC® 25955™ |
| M-49 | *Bacillus selenitireducens* ATCC® 700615™ |
| M-50 | *Acidithiobacillus ferrooxidans* ATCC® 23270™ |
| M-51 | *Phanerochaete chrysosporium* ATCC® 24725 |
| M-52 | *Escherichia Coli* ATCC® 33456™ |
| M-53 | *Acinetobacter calcoaceticus* ATCC® 23055™ |
| M-54 | *Variovorax paradoxus* ATCC® 17713™ |
| M-55 | *Paracoccus denitrificans* ATCC® 19367™ |

TABLE III

| Polymer Solution Identifier | Composition |
|---|---|
| A | 8.0 wt. percent of polyvinyl alcohol available as Elvanol® 70-04 from Dupont, Inc. having a degree of hydrolysis of 98.0-98.8 mol percent; 2.0 wt. percent of sodium alginate available as Nalgin™ MV-120 from Ingredient Solutions, Inc.; 0.5 wt. percent of medium molecular weight Poly(D-glucosamine) available as Sigma-Aldrich® 448877 |
| B | 25 wt. percent of Poly(acrylamide-co-acrylic acid) potassium salt-cross-linked available as Sigma-Aldrich® 432776; 0.2 wt. percent of Poly(2-hydroxyethyl methacrylate) available as Sigma-Aldrich® P3932 |
| C | 14 wt. percent of poly(vinyl alcohol-co-ethylene) available as Sigma-Aldrich® 414093 having an ethylene composition of 32 mol percent; 2.0 wt. percent of polyethylene glycol with an average molecular weight of 200 available as Sigma-Aldrich® P3015 |
| D | 6.6 wt. percent of poly(N-isopropylacrylamide) available as Sigma-Aldrich® 535311 having a molecular weight of 19,000-30,000; 5.0 wt. percent of ethylene glycol dimethacrylate available as Sigma-Aldrich® 335681 |

TABLE III-continued

| Polymer Solution Identifier | Composition |
|---|---|
| E | 9.5 wt. percent of polyethylene oxide available as POLYOX™ WSR N-10 from Dow, Inc. having an approximate molecular weight of 100,000; 0.5 wt. percent of polyethylene glycol with an average molecular weight of 200 available as Sigma-Aldrich® P3015 |
| F | 23.0 wt. percent of polyvinyl alcohol available as Elvanol® 70-03 from Dupont™ having a degree of hydrolysis of 98-98.8 mol percent; 1.0% wt. percent of anhydrous calcium chloride available as Sigma-Aldrich® C1016; 0.9 wt. percent of sodium alginate available as Nalgin™ MV-120 from Ingredient Solutions, Inc. |
| G | 22.5 wt. percent of polyvinyl alcohol available as Elvanol® 70-20 from Dupont™ having a degree of hydrolysis of 98.5-99.2 mol percent; 2.0 wt. percent of xantham gum from *Xanthamonas campestris* available as Sigma-Aldrich® G1253 |
| H | 15.0 wt. percent of polyvinyl alcohol available as Mowial® 28-99 from Kuraray Co., Ltd.™ having a degree of hydrolysis of 99.0-99.8 mol percent and a molecular weight of 145,000; 3.5 wt. percent of sodium alginate available as Nalgin™ MV-120 from Ingredient Solutions, Inc. |
| I | 21.7 wt. percent of polyethylene oxide available as POLYOX™ WSR N-80 from Dow, Inc. having an approximate molecular weight of 200,000; 1.0 wt. percent of medium molecular weight Poly(D-glucosamine) available as Sigma-Aldrich® 448877; 0.5 wt. percent of sodium alginate available as Nalgin™ MV-120 from Ingredient Solutions, Inc. |
| J | 12.0 wt. percent of Poly(acrylamide-co-acrylic acid) potassium salt-cross-linked available as Sigma-Aldrich® 432776; 2.0 wt. percent of sodium alginate available as Nalgin™ MV-120 from Ingredient Solutions, Inc. |
| K | 12.0 wt. percent of Poly(acrylamide-co-acrylic acid) potassium salt-cross-linked available as Sigma-Aldrich® 432776; 0.2 wt. percent of ethylene glycol dimethacrylate available as Sigma-Aldrich® 335681 |
| L | 12.5 wt. percent of polyvinyl alcohol available as Poval® PVA-202E from Kuraray Co., Ltd.™ having a degree of hydrolysis of 87-89 mol percent; 1.0 wt. percent polyaniline available as Sigma-Aldrich® 577073 |
| M | 12.5 wt. percent of poly(acrylic acid) available as Sigma-Aldrich® 192023 having an average molecular weight of 2000; 1.0 wt. percent polyaniline available as Sigma-Aldrich® 577073 |
| N | 55.0 wt. percent of poly(vinyl alcohol-co-ethylene) available as Sigma-Aldrich® 414093 having an ethylene composition of 32 mol percent; 1.0 wt. percent of poly(2-hydroxyethyl methacrylate) available as Sigma-Aldrich® P3932; 0.1 wt. percent of sodium alginate available as Sigma-Aldrich® W201502 |
| O | 21.0 wt. percent of poly(acrylic acid) available as Sigma-Aldrich® 192023 having an average molecular weight of 2000; 0.5 wt. percent of polyvinyl alcohol available as Elvanol® 70-04 from Dupont, Inc. having a degree of hydrolysis of 98.0-98.8 mol percent |
| P | 12.7 wt. percent of polyethylene oxide available as POLYOX™ WSR N-80 from Dow, Inc. having an approximate molecular weight of 200,000; 12.0 wt. percent of polyvinyl alcohol available as Elvanol® 70-04 from Dupont, Inc. having a degree of hydrolysis of 98.0-98.8 mol percent |
| Q | 13.0 wt. percent of polyethylene oxide available as POLYOX™ WSR N-80 from Dow, Inc. having an approximate molecular weight of 200,000; 2.1 wt. percent of polyaniline available as Sigma-Aldrich® 577073 |
| R | 18.0 wt. percent of poly(N-isopropylacrylamide) available as Sigma-Aldrich® 535311 having a molecular weight of 19,000-30,000; 0.95 wt. percent of anhydrous calcium chloride available as Sigma-Aldrich® C1016 |
| S | 50.0 wt. percent of polyvinyl alcohol available as Elvanol® 70-03 from Dupont having a degree of hydrolysis of 98-98.8 mol percent; 0.2 wt. percent polyaniline available as Sigma-Aldrich® 577073 |
| T | 10.0 wt. percent of poly(acrylic acid) available as Sigma-Aldrich® 192023 having an average molecular weight of 2000; 1.0 wt. percent of polyethylene glycol with an average molecular weight of 200 available as Sigma-Aldrich® P3015 |
| U | 20.0 wt. percent of polyvinyl alcohol available as Elvanol® 70-06 from Dupont™ Inc. having a degree of hydrolysis of 98.5-99.2 mol percent; 1.0 wt. percent of Poly(2-hydroxyethyl methacrylate) available as Sigma-Aldrich® P3932 |
| V | 18.0 wt. percent of polyvinyl alcohol-co-ethylene) available as Sigma-Aldrich® 414093 having an ethylene composition of 32 mol percent; 1.8 wt. percent of sodium alginate available as Nalgin™ MV-120 from Ingredient Solutions, Inc. |
| W | 10.0 wt. percent of polyethylene oxide available as POLYOX™ WSR N-80 from Dow, Inc. having an approximate molecular weight of 200,000; 10.0 wt. percent of polyethylene glycol with an average molecular weight of 200 available as Sigma-Aldrich® P3015; 10.0 wt. percent κ-Carrageenan available as Sigma-Alrdich® 22048 |
| X | 11.5 wt. percent of polyvinyl alcohol available as Elvanol® 70-75 from Dupont™ Inc. having a degree of hydrolysis of 98.5-99.2 mol percent; 4.7 wt. percent of polyethylene glycol with an average molecular weight of 200 available as Sigma-Aldrich® P3015 |
| Y | 12.5 wt. percent of polyvinyl alcohol available as Elvanol® 50-04 from Dupont™ Inc. having a degree of hydrolysis of 87.0-89.0 mol percent; 3.0 wt. percent of ethylene glycol dimethacrylate available as Sigma-Aldrich® 335681; 1.0 wt. percent κ-Carrageenan available as Sigma-Alrdich® 22048 |
| Z | 20.0 wt. percent of Elvanol® 70-04 polyvinyl alcohol from Dupont, Inc. having a degree of hydrolysis of 98.0-98.8 mol percent; 1.90 wt. percent of sodium alginate available as Nalgin™ MV-120 from Ingredient Solutions, Inc.; 1.0 wt. percent κ-Carrageenan available as Sigma-Alrdich® 22048 |
| AA | 3.7 wt. percent of polyethylene oxide available as POLYOX™ WSR N-80 from Dow, Inc. having an approximate molecular weight of 200,000; 0.5 wt. percent of anhydrous calcium chloride available as Sigma-Aldrich® C1016; 0.2 wt. percent κ-Carrageenan available as Sigma-Aldrich® 22048 |
| BB | 35.0 wt. percent of polyvinyl alcohol available as Elvanol® 70-27 from Dupont™ Inc. having a degree of hydrolysis of 95.5-96.5 mol percent; 6.0 wt. percent of anhydrous calcium chloride available as Sigma-Aldrich® C1016; 3.3 wt. percent of GRINDSTED® Carrageenan CLFLX from Dupont, Inc. |
| CC | 25.0 wt. percent of polyethylene-alt-maleic anhydride available as Sigma-Aldrich® 188050 having an average molecular weight 100,000-500,000; 2.2 wt. percent of polyethylene glycol with an average molecular weight of 200 available as Sigma-Aldrich® P3015 |
| DD | 7.0 wt. percent of poly(vinyl alcohol-co-ethylene) available as Sigma-Aldrich® 414093 having an ethylene composition of 32 mol percent; 7.0 wt. percent of polyacrylic acid with an average molecular weight of 1800 available as Sigma-Aldrich® 323667 |
| EE | 8.0 wt. percent of polyvinyl alcohol available as Sigma-Aldrich® 363065 having a degree of hydrolysis of 99+ mol percent and a molecular weight of 146,000-186,000; 1.0 wt. percent κ-Carrageenan available as Sigma-Alrdich® 22048; 1.0 wt. percent of ethylene glycol dimethacrylate available as Sigma-Aldrich® 335681 |

TABLE III-continued

| Polymer Solution Identifier | Composition |
|---|---|
| FF | 8.0 wt. percent of polyethylene oxide available as POLYOX ™ WSR N-80 from Dow, Inc. having an approximate molecular weight of 200,000; 1.0 wt. percent of ethylene glycol dimethacrylate available as Sigma-Aldrich ® 335681 |
| GG | 14.4 wt. percent of polyvinyl alcohol available as Elvanol ® 70-14 from Dupont ™ Inc. having a degree of hydrolysis of 95.0-97.0 mol percent; 14.0 wt. percent of polyacrylic acid with an average molecular weight of 1800 available as Sigma-Aldrich ® 323667 |
| HH | 18.1 wt. percent of poly(vinyl alcohol-co-ethylene) available as Sigma-Aldrich ® 414093 having an ethylene composition of 32 mol percent; 5.5 wt. percent of Poly(2-hydroxyethyl methacrylate) available as Sigma-Aldrich ® P3932; 1.0 wt. percent of anhydrous calcium chloride available as Sigma-Aldrich ® C1016 |
| II | 4.0 wt. percent of polyethylene oxide available as POLYOX ™ WSR N-10 from Dow, Inc. having an approximate molecular weight of 100,000; 3.8 wt. percent of polyacrylic acid with an average molecular weight of 1800 available as Sigma-Aldrich ® 323667 |
| JJ | 7.7 wt. percent of polyvinyl alcohol available as Poval ® PVA-202E from Kuraray Co., Ltd. ™ having a degree of hydrolysis of 87-89 mol percent; 3.4 wt. percent of medium molecular weight Poly(D-glucosamine) available as Sigma-Aldrich ® 448877 |
| KK | 13.5 wt. percent of Poly(2-hydroxyethyl methacrylate) available as Sigma-Aldrich ® P3932; 4.0 wt. percent of polyethylene-alt-maleic anhydride available as Sigma-Aldrich ® 188050 having an average molecular weight 100,000-500,000 |
| LL | 19.0 wt. percent of polyvinyl alcohol available as Poval ® PVA-217E from Kuraray Co., Ltd. ™ having a degree of hydrolysis of 87-89 mol percent; 1.2 wt. percent of Poly(2-hydroxyethyl methacrylate) available as Sigma-Aldrich ® P3932 |
| MM | 33.0 wt. percent of polyethylene oxide available as POLYOX ™ WSR N-10 from Dow, Inc. having an approximate molecular weight of 100,000; 1.0 wt. percent of medium molecular weight Poly(D-glucosamine) available as Sigma-Aldrich ® 448877 |
| NN | 23.0 wt. percent of polyethylene oxide available as POLYOX ™ WSR N-10 from Dow, Inc. having an approximate molecular weight of 100,000; 2.0 wt. percent of anhydrous calcium chloride available as Sigma-Aldrich ® C1016 |
| OO | 16.0 wt. percent of poly(vinyl alcohol-co-ethylene) available as Sigma-Aldrich ® 414093 having an ethylene composition of 32 mol percent; 0.5 wt. percent of medium molecular weight Poly(D-glucosamine) available as Sigma-Aldrich ® 448877 |
| PP | 14.0 wt. percent of polyvinyl alcohol available as Elvanol ® 70-04 from Dupont, Inc. having a degree of hydrolysis of 98.0-98.8 mol percent; 0.55 wt. percent of sodium alginate available as Nalgin ™ MV-120 from Ingredient Solutions, Inc.; 0.27 wt. percent of polyethylene oxide available as POLYOX ™ WSR N-80 from Dow, Inc. having an approximate molecular weight of 200,000 |
| QQ | 40.0 wt. percent of polyvinyl alcohol available as Poval ® PVA-224E from Kuraray Co., Ltd. ™ having a degree of hydrolysis of 80-83 mol percent; 0.7 wt. percent of medium molecular weight Poly(D-glucosamine) available as Sigma-Aldrich ® 448877 |
| RR | 12.2 wt. percent of polyethylene oxide available as POLYOX ™ WSR N-80 from Dow, Inc. having an approximate molecular weight of 200,000; 2.2 wt. percent of sodium alginate available as Nalgin ™ MV-120 from Ingredient Solutions, Inc. |
| SS | 5.6 wt. percent of ethylene vinyl alcohol copolymer available as Exceval ™ HR-3010 from Kuraray Co., Ltd. ™ having a degree of hydrolysis of 99-99.4 mol percent; 0.1 wt. percent of sodium carboxymethyl cellulose with an average molecular weight of 250,000 available as Sigma-Aldrich ® 419311 |
| TT | 6.9 wt. percent of polyethylene oxide available as POLYOX ™ WSR N-80 from Dow, Inc. having an approximate molecular weight of 200,000; 6.0 wt. percent of Poly(2-hydroxyethyl methacrylate) available as Sigma-Aldrich ® P3932 |
| UU | 2.5 wt. percent of polyethylene-alt-maleic anhydride available as Sigma-Aldrich ® 188050 having an average molecular weight 100,000-500,000; 2.0 wt. percent of polyacrylic acid with an average molecular weight of 1800 available as Sigma-Aldrich ® 323667 |
| VV | 3.8 wt. percent of polyvinyl alcohol available as Poval ® PVA-224E from Kuraray Co., Ltd. ™ having a degree of hydrolysis of 80-83 mol percent; 3.0 wt. percent of polyacrylic acid with an average molecular weight of 1800 available as Sigma-Aldrich ® 323667 |
| WW | 14.0 wt. percent of ethylene vinyl alcohol copolymer available as Exceval ™ RS-1717 from Kuraray Co., Ltd. ™ having a degree of hydrolysis of 92-94 mol percent; 2.0 wt. percent of xantham gum from *Xanthamonas campestris* available as Sigma-Aldrich ® G1253 |
| XX | 1.0 wt. percent of polyvinyl alcohol available as Elvanol ® 70-03 from Dupont ™ having a degree of hydrolysis of 98-98.8 mol percent; 0.1 wt. percent of sodium carboxymethyl cellulose with an average molecular weight of 250,000 available as Sigma-Aldrich ® 419311 |
| YY | 4.0 wt. percent of polyvinyl alcohol available as Mowial ® 4-88 from Kuraray Co., Ltd. ™ having a degree of hydrolysis of 86.7-88.7 mol percent and a molecular weight of 31,000; 0.05 wt. percent of anhydrous calcium chloride available as Sigma-Aldrich ® C1016 |
| ZZ | 9.0 wt. percent of polyvinyl alcohol available as Mowial ® 10-98 from Kuraray Co., Ltd. ™ having a degree of hydrolysis of 98.0-98.8 mol percent and a molecular weight of 61,000; 0.3 wt. percent of Poly(2-hydroxyethyl methacrylate) available as Sigma-Aldrich ® P3932 |
| AAA | 5.0 wt. percent of polyvinyl alcohol available as Mowial ® 56-98 from Kuraray Co., Ltd. ™ having a degree of hydrolysis of 98.0-98.8 mol percent and a molecular weight of 195,000; 5.0 wt. percent of polyethylene glycol with an average molecular weight of 200 available as Sigma-Aldrich ® P3015 |
| BBB | 15.5 wt. percent of polyvinyl alcohol available as Mowial ® 28-99 from Kuraray Co., Ltd. ™ having a degree of hydrolysis of 99.0-99.8 mol percent and a molecular weight of 145,000; 1.5 wt. percent polyethylene glycol with an average molecular weight of 1450 available as Sigma-Aldrich ® P5402 |
| CCC | 17.0 wt. percent of polyvinyl alcohol available as Sigma-Aldrich ® 363138 having a degree of hydrolysis of 98-99 mol percent and a molecular weight of 31,000-50,000; 3.0 wt. percent of ethylene glycol dimethacrylate available as Sigma-Aldrich ® 335681 |
| DDD | 1.0 wt. percent of polyethylene oxide available as POLYOX ™ WSR N-10 from Dow, Inc. having an approximate molecular weight of 100,000; 1.0 wt. percent of medium molecular weight Poly(D-glucosamine) available as Sigma-Aldrich ® 448877 |

TABLE III-continued

| Polymer Solution Identifier | Composition |
|---|---|
| EEE | 8.0 wt. percent of polyethylene oxide available as POLYOX ™ WSR N-80 from Dow, Inc. having an approximate molecular weight of 200,000; 7.7 wt. percent polyethylene glycol with an average molecular weight of 1450 available as Sigma-Aldrich ® P5402 |
| FFF | 18.7 wt. percent of polyvinyl alcohol available as Sigma-Aldrich ® 363065 having a degree of hydrolysis of 99+ mol percent and a molecular weight of 146,000-186,000; 0.8 wt. percent of polyacrylic acid with an average molecular weight of 1800 available as Sigma-Aldrich ® 323667 |
| GGG | 25.9 wt. percent of polyvinyl alcohol available as Sigma-Aldrich ® 363065 having a degree of hydrolysis of 99+ mol percent and a molecular weight of 146,000-186,000; 2.9 wt. percent of sodium alginate available as Nalgin ™ MV-120 from Ingredient Solutions, Inc.; 2.7 wt. percent of polyacrylic acid with an average molecular weight of 1800 available as Sigma-Aldrich ® 323667 |
| HHH | 19.0 wt. percent of polyethylene-alt-maleic anhydride available as Sigma-Aldrich ® 188050 having an average molecular weight 100,000-500,000; 0.05 wt. percent of medium molecular weight Poly(D-glucosamine) available as Sigma-Aldrich ® 448877; 0.03 wt. percent of xantham gum from *Xanthamonas campestris* available as Sigma-Aldrich ® G1253 |
| III | 5.0 wt. percent of polyvidone available as Kollidon ® 25 Sigma-Aldrich ® 02286 having a degree of hydrolysis of 99+ mol percent and a molecular weight of 146,000-186,000; 4.0 wt. percent of polyacrylic acid with an average molecular weight of 1800 available as Sigma-Aldrich ® 323667 |
| JJJ | 4.5 wt. percent of polyethylene-alt-maleic anhydride available as Sigma-Aldrich ® 188050 having an average molecular weight 100,000-500,000; 4.5 wt. percent of polyvinyl alcohol available as Poval ® PVA-224E from Kuraray Co., Ltd. ™ having a degree of hydrolysis of 80-83 mol percent; |
| KKK | 20.0 wt. percent of poly(acrylic acid) available as Sigma-Aldrich ® 192023 having an average molecular weight of 2000; 8.0 wt. percent of Poly(2-hydroxyethyl methacrylate) available as Sigma-Aldrich ® P3932; 2.0 wt. percent of ethylene glycol dimethacrylate available as Sigma-Aldrich ® 335681 |
| LLL | 3.5 wt. percent of polyethylene-alt-maleic anhydride available as Sigma-Aldrich ® 188050 having an average molecular weight 100,000-500,000; 1.0 wt. percent of ethylene glycol dimethacrylate available as Sigma-Aldrich ® 335681; 0.05 wt. percent of anhydrous calcium chloride available as Sigma-Aldrich ® C1016 |
| MMM | 9.0 wt. percent of poly(N-isopropylacrylamide) available as Sigma-Aldrich ® 535311 having a molecular weight of 19,000-30,000; 2.0 wt. percent of sodium alginate available as Nalgin ™ MV-120 from Ingredient Solutions, Inc. |
| NNN | 8.8 wt. percent of polyethylene-alt-maleic anhydride available as Sigma-Aldrich ® 188050 having an average molecular weight 100,000-500,000; 1.0 wt. percent polyethylene glycol with an average molecular weight of 1450 available as Sigma-Aldrich ® P5402 |
| OOO | 2.1 wt. percent of polyvinyl alcohol-co-ethylene) available as Sigma-Aldrich ® 414093 having an ethylene composition of 32 mol percent; 0.1 wt. percent of medium molecular weight Poly(D-glucosamine) available as Sigma-Aldrich ® 448877 |
| PPP | 4.3 wt. percent of Poly(acrylamide-co-acrylic acid) potassium salt-cross-linked available as Sigma-Aldrich ® 432776; 2.0 wt. percent of xantham gum from *Xanthamonas campestris* available as Sigma-Aldrich ® G1253 |
| QQQ | 1.3 wt. percent of polyethylene-alt-maleic anhydride available as Sigma-Aldrich ® 188050 having an average molecular weight 100,000-500,000; 0.5 wt. percent of Poly(2-hydroxyethyl methacrylate) available as Sigma-Aldrich ® P3932 |
| RRR | 9.4 wt. percent of polyvidone available as Kollidon ® 25 Sigma-Aldrich ® 02286 having a degree of hydrolysis of 99+ mol percent and a molecular weight of 146,000-186,000; 2.0 wt. percent of xantham gum from *Xanthamonas campestris* available as Sigma-Aldrich ® G1253 |
| SSS | 5.4 wt. percent of polyethylene oxide available as POLYOX ™ WSR N-10 from Dow, Inc. having an approximate molecular weight of 100,000; 2.5 wt. percent polyethylene glycol with an average molecular weight of 1450 available as Sigma-Aldrich ® P5402 |
| TTT | 7.9 wt. percent of polyethylene oxide available as POLYOX ™ WSR N-10 from Dow, Inc. having an approximate molecular weight of 100,000; 1.1 wt. percent of medium molecular weight Poly(D-glucosamine) available as Sigma-Aldrich ® 448877 |
| UUU | 9.0 wt. percent of poly(N-isopropylacrylamide) available as Sigma-Aldrich ® 535311 having a molecular weight of 19,000-30,000; 1.1 wt. percent of sodium alginate available as Nalgin ™ MV-120 from Ingredient Solutions, Inc. |
| VVV | 10.5 wt. percent of ethylene vinyl alcohol copolymer available as Exceval ™ RS-1717 from Kuraray Co., Ltd. ™ having a degree of hydrolysis of 92-94 mol percent; 2.2 wt. percent of Poly(2-hydroxyethyl methacrylate) available as Sigma-Aldrich ® P3932 |
| WWW | 10.0 wt. percent of polyvinyl alcohol available as Mowial ® 28-99 from Kuraray Co., Ltd. ™ having a degree of hydrolysis of 99.0-99.8 mol percent and a molecular weight of 145,000; 4.5 wt. percent of medium molecular weight Poly(D-glucosamine) available as Sigma-Aldrich ® 448877 |
| XXX | 10.0 wt. percent of poly(vinyl alcohol-co-ethylene) available as Sigma-Aldrich ® 414093 having an ethylene composition of 32 mol percent; 2.0 wt. percent of xantham gum from *Xanthamonas campestris* available as Sigma-Aldrich ® G1253 |

TABLE IV

| Solid Additive Package Identifier | Composition |
|---|---|
| S-1 | Clay available as Nanomer ® I.28E from Sigma-Aldrich ® 682608 containing 25-30 wt % trimethyl stearyl ammonium on Montmorillonite clay base material matrix |
| S-2 | Clay available as Nanomer ® PGV hydrophilic bentonite from Sigma-Aldrich ® 682659 |
| S-3 | Clay available as Nanomer ® I.44P from Sigma-Aldrich ® 682624 containing 35-45% wt. % dimethyl dialkyl amine on Montmorillonite clay base material matrix |

TABLE IV-continued

| Solid Additive Package Identifier | Composition |
|---|---|
| S-4 | Clay available as Nanomer ® I.34MN from Sigma-Aldrich ® 682640 containing 25-30 wt. % methyl dihydroxyethyl hydrogenated tallow ammonium on Montmorillonite clay base material matrix |
| S-5 | Natural bentonite clay as Cloisite ® Ca++ from Southern Clay Products/Rockwood Additives |
| S-6 | Natural bentonite clay as Cloisite ® 116 from Southern Clay Products/Rockwood Additives |
| S-7 | Granular activated carbon having an effective size 0.7-0.9 mm available as HYDRODARCO ® 3000 from Norit Americas |
| S-8 | Granular activated carbon having an effective size of 1 mm available as NORIT ® GAC 300 from Norit Americas |
| S-9 | Fumed silica having an average particle size of 0.007 microns available as Sigma-Aldrich ® S 5130 |
| S-10 | Sodium metasilicate as granular powder available as Sigma-Aldrich ® 307815 |
| S-11 | Molecular sieves available as Sigma-Aldrich ® 283592 having an average particle size of 2 microns |
| S-12 | Sodium hydroxidecoated silica available as Ascarite ® II from Sigma-Aldrich 223913 |
| S-13 | Starch as available from Sigma-Aldrich ® S4251 |
| S-14 | Starch as available from Spectrum ® M1372 |
| S-15 | Starch as available as CHARGEMASTER ® L340 from Grain Processing Corporation |
| S-16 | Trichromatic phosphors, pre-mixed available as Sigma-Aldrich ® 755966 |
| S-17 | Yttrium oxide, europium doped phosphors with average particle size 4-8 microns as available as Sigma-Aldrich ® 756490 |
| S-18 | Phosphors as sodium yttrium fluoride, ytterbium and erbium doped with particle size 1-5 microns available as Sigma-Alrich ® 756555 |
| S-19 | *Sphagnum* Peat Moss Absorbent available as CEP-PEAT2-P from Complete Environmental Products, Inc. |
| S-20 | Aluminum oxide nanowires with diameter of 2-6 nanometers and length 200-400 nanometers as available as Sigma-Aldrich ® 551643 |
| S-21 | Mesostructured silica with cell window size ~15 nanometers as available as Sigma-Aldrich ® 560979 |
| S-22 | Hydroxyapatite nanopowder with particle size <200 nanometers as available as Sigma-Aldrich ® 677418 |
| S-23 | Chitin as available as Sigma-Aldrich ® C7170 |
| S-24 | Iron oxide as available as Sigma-Aldrich ® 310069 |
| S-25 | Fine ground silica available as MIN-U-SIL ® from U.S. Silica |
| S-26 | Polyethylene powder as MIPELON ™ from Mitsui Chemicals America, Inc. |
| S-27 | Untreated wheat germ as available as Sigma-Aldrich ® W0125 |

Each of the above biocatalysts exhibit phenotypic alterations and the biocatalysts have a stable population of microorganisms and do not generate any appreciable debris from metabolic activity.

Bioconversions

A. Overview

As described above, the biocatalysts of this invention can be used for a wide range of anabolic and catabolic bioconversion processes. Substrates may be one or more of normally a gas, liquid or solid. The substrates preferably are capable of being dissolved in the aqueous medium for contact with the biocatalyst although the biocatalysts of this invention can find advantageous application in processes where the substrate has little, if any, solubility in water, especially in gas-phase metabolic processes enabled by the biocatalysts of this invention. In the broad aspects the processes of this invention pertain to the bioconversion of substrate to bioproduct, which processes comprise (a) contacting the substrate with biocatalyst of this invention, and (b) maintaining the biocatalyst under metabolic conditions for a time sufficient to bioconvert at least a portion of the substrate to said bioproduct. Usually the bioproduct is recovered; however, in some aspects of this invention, the bioproduct may intentionally be a chemical that is capable of being sequestered in the biocatalyst, e.g., where removing soluble metal compounds from water.

Substrates can be natural or xenobiotic substances in an organism (plant or animal) or can be obtained from other sources. Hence, substrates include, but are not limited to, those that can be, or can be derived from, plant, animal or fossil fuel sources, or can be produced by a chemical or industrial process. The biocatalysts can also be applicable to water supply or waste water clean-up operations where the substrate is one or more contaminants. The biocatalysts generate metabolites as a result of anabolic or catabolic activity and the metabolites may be primary or secondary metabolites. The processes of this invention can be used to produce any type of anabolic metabolite.

Bioproducts may be degradation products especially where contaminants are being removed from a fluid such as for water supply or waste water treatment. Such degradation bioproducts include, but are not limited to, carbon dioxide, carbon monoxide, hydrogen, carbonyl sulfide, hydrogen sulfide, water, and salts such as carbonate, bicarbonate, sulfide, sulfite, sulfate, phosphate, phosphite, chloride, bromide, iodide, and borate salts of ammonium, or group 1 to 16 (IUPAC) metals such as sodium, potassium, manganese, magnesium, calcium, barium, iron, copper, cobalt, tin, selenium, radium, uranium, bismuth, cadmium, mercury, molybdenum and tungsten.

Bioproducts may be one or more of aliphatic compounds and aromatic compounds including but not limited to hydrocarbons of up to 44 or 50 carbons, and hydrocarbons substituted with one or more of hydroxyl, acyl, carboxyl, amine, amide, halo, nitro, sulfonyl, and phosphino moieties, and hydrocarbons containing one or more hetero atoms including but not limited to, nitrogen, sulfur, oxygen, and phosphorus atoms. Examples of organic products as end products from metabolic processes are those listed in United States published patent application no. 2010/0279354 A1, especially as set forth in paragraphs 0129 through 0149. See also, United States published patent application no. 2011/0165639 A1. Other bioproducts include p-toluate, terephthalate, terephthalic acid, aniline, putrescine, cyclohexanone, adipate, hexamethylenediamine (HMDA), 6-aminocaproic acid, malate, acrylate, apidipic acid, methacrylic acid, 3-hydroxypropionic acid (3HP), succinate, butadiene, propylene, caprolactam, fatty alcohols, fatty acids, glycerates, acrylic acid, acrylate esters, methacrylic acid, methacrylic acids, fucoidan, muconate, iodine, chlorophyll, carotenoid, calcium, magnesium, iron, sodium, potassium, and phosphate. The bioproduct may be a chemical that provides a biological activity with respect to a plant or animal or human. The biological activity can be one or more of a number of different activities such as antiviral, antibiotic, depressant, stimulant, growth promoters, hormone, insulin, reproductive, attractant, repellant, biocide, and the like. Examples of antibiotics include, but are not limited to, aminoglycosides (e.g., amikacin, gentamicin, kanamycin, neomycin, netilmicin, tobramycin, paromomycin); ansamycins (e.g., geldanamycin, herbimycin); carbacephem (loracarbef); carbapenems (e.g., ertapenem, doripenem, imipenem/cilastatin, meropenem); cephalosporins (first generation, e.g., cefadroxil, cefazolin, cefalotin, cefalexin); cephalosporins (second generation, e.g., cefaclor, cefamandole, cefoxitin, cefprozil, cefuroxime); cephalosporins (third generation, e.g., cefixime, cefdinir, cefditoren, cefoperazone, cefotaxime, cefpodoxime, ceftazidime, ceftibuten, ceftizoxime, ceftriaxone); cephalosporins (fourth generation, e.g., cefepime); cephalosporins (fifth generation, e.g., ceftobiprole); glycopeptides (e.g., teicoplanin, vancomycin, telavancin); lincosamides (e.g., clindamycin, lincomycin); macrolides (e.g., azithromycin, clarithromycin, dirithromycin, erythromycin, roxithromycin, troleandomycin, telithromycin spectinomycin); monobactams (e.g., aztreonam); nitrofurans (e.g., furazolidone, nitrofurantoin); penicillins (e.g., amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, ticarcillin); penicillin combinations (e.g., amoxicillin/clavulanate, ampicillin/sulbactam, piperacillin/tazobactam, ticarcillin/clavulanate); polypeptides (e.g., bacitracin, colistin, polymyxin B); quinolones (e.g., ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin); sulfonamides (e.g., mafenide; sulfonamidochrysoidine, sulfacetamide, sulfadiazine, silver sulfadiazine, sulfamethizole, sulfamethoxazole, sulfanilimide, sulfasalazine, sulfisoxazole, trimethoprim, trimethoprim-Sulfamethoxazole (Co-trimoxazole) (TMP-SMX); tetracyclines (e.g., demeclocycline, doxycycline, minocycline, oxytetracycline, tetracycline); drugs against *mycobacteria* (e.g., clofazimine, dapsone, capreomycin, cycloserine, ethambutol, ethionamide, isoniazid, pyrazinamide, rifampin, rifabutin, rifapentine, streptomycin) and others (e.g., arsphenamine, chloramphenicol, fosfomycin, fusidic acid, linezolid, metronidazole, mupirocin, platensimycin, luinupristin/dalfopristin, rifaximin, thiamphenicol, tinidazole).

Preferably an anabolic bioproduct is at least one of an oxygenated organic compound and hydrocarbon of up to about 100, often up to about 50, carbon atoms. Most preferred oxygenated organic product includes methanol, ethanol, acetic acid, n-propanol, propanol, propionic acid, n-butanol, i-butanol, butyric acid, acetone, and methyl ethyl ketone.

Examples of anabolic or catabolic processes suitable to be practiced by the processes of this invention include, but are not limited to:

Syngas, i.e., gas containing carbon monoxide and optionally hydrogen, for conversion to oxygenated organic product and hydrocarbons. In typical prior art processes for the conversion of syngas to oxygenated organic product, a limiting factor on productivity is the mass transfer of carbon monoxide and hydrogen from the gas phase into the liquid phase of the aqueous medium. By using the biocatalysts of this invention for syngas bioconversion, mass transfer can be enhanced.

Carbon dioxide-containing gases for conversion to oxygenated organic product and hydrocarbons. The anabolic conversion may be effected by algae, cyanobacteria, or other photo activated microorganisms, e.g., to produce alcohols, biodiesel, and like. Other bioconversion processes using carbon dioxide to produce bioproducts include those to make organic acids and esters and diacids and diesters such as succinic acid and lactic acid.

Combustion gases, e.g., from the disposal of solid wastes or generation of energy, where the substrate comprises contaminants sought to be removed from the gases such as oxygenated halides, sulfoxy moieties, nitrogen oxides, heavy metal compounds and the like.

Industrial process waste gases containing, for instance, volatile organic compounds; solvents such as chlorine containing solvents, ketones, aldehydes, peroxygenates, and the like; ammonia or volatile amines; mercaptans and other sulfur containing compounds; nitrogen oxides; and the like. The industrial process waste gases may be air-based, such as exhaust from painting operations, or maybe devoid of air such as purge or waste gases. The ability to subject these substrates to catabolic degradation can often eliminate the necessity for a thermal oxidation unit operation resulting in both capital and energy savings as often natural gas or other fuel is required to maintain temperature for the thermal oxidation unit.

Natural gas (including, but not limited to, gas recovered by underground fracturing processes, i.e., frac gas) wherein the substrate for catabolic processing may be one or more of oxygenates, such as nitrogen oxides, sulfur oxides; perchlorates; sulfides, ammonia; mercaptans; and the like.

Nitrates, perchlorates, taste and odor compounds, organics, chlorinated hydrocarbons, and the like removal from the water. The source of the water may be from a water treatment facility, ground sources, surface sources, municipal waste processing, and industrial waste water. The water stream may be derived from other bioconversion processes where substrate is not fully consumed, such as in corn ethanol processes.

Carbohydrate, including, but not limited to cellulose, hemicellulose, starches, and sugars for conversion to oxygenated organic product and hydrocarbons.

Oxyanions, hydroxyls or soluble salts of sulfur, phosphorus, selenium, tungsten, molybdenum, bismuth, strontium, cadmium, chromium, titanium, nickel, iron, zinc, copper, arsenic, vanadium, uranium, radium, manganese, germanium, indium, antimony mercury, and rare earth metals for removal from water by bioconversion and sequestration.

The metabolic processes using the biocatalysts may be conducted in any suitable manner employing metabolic conditions sufficient for the biocatalyst to convert the substrate to the sought bioproduct. Metabolic conditions include conditions of temperature, pressure, oxygenation, pH, and nutrients (including micronutrients) and additives required or desired for the microorganisms in the biocatalyst. Due to the microenvironments and phenotypic alterations associated with the biocatalysts of this invention, often a broader range of metabolic conditions can be effectively used than those suitable for planktonic microorganisms. Any suitable bioreactor system may be used including Typical Bioreactor Systems.

The metabolic processes using the biocatalysts of this invention provide sufficient water to the biocatalyst to maintain the biocatalyst hydrated. The bioconversion processes may involve direct contact with gas containing substrate or in contact with a liquid medium, often an aqueous medium. Water for this aqueous medium may be provided from any suitable source including, but not limited to, tap water, demineralized water, distilled water, and process or waste water streams. The aqueous medium can contain nutrients and additives such as co-metabolites, potentiators, enhancers, inducers growth promoters, buffers, antibiotics, vitamins, minerals, nitrogen sources, and sulfur sources as is known in the art. If desired, an antifoam agent may be used in the aqueous medium. In some instances, where additives are desired or required for the metabolic process, the biocatalysts of this invention exhibit at least equivalent bioconversion activity at a lesser concentration of such additives as compared to a planktonic, free-suspension system, all else being substantially the same.

The bioreactor may or may not be sterilized prior to introducing the aqueous medium. Due to the use of biocatalysts containing significant populations of microorganisms, bioreactors can have a rapid start-up time.

The processes may be conducted with all carbon requirements being provided in the aqueous medium or on a carbon source deficient basis. Where operating in a carbon source deficiency, the aqueous medium often provides at least about 50, frequently at least about 75, say, 80 to less than 100, mass percent on a carbon basis of the carbon nutrient. In some instances polysaccharide is included in the biocatalyst where carbon source deficiency operations are anticipated. The carbon source deficiency may occur intermittently or continuously during the metabolic process.

The bioconversion processes may be optimized to achieve one or more objectives. For instance, the processes may be designed to provide high conversions of substrate to bioproduct or may be designed to balance capital and energy costs against conversion to bioproduct. As the biocatalysts are highly hydrated, generally their density is close to that of water. Accordingly, with fluidized bed reactor designs using an aqueous feed stream, energy consumption is lower than that where higher density supports are used. In some instances where the metabolic processes generate a gas, e.g., in the conversion of sugars to alkanols or in the bioconversion of nitrate anion to nitrogen gas, gas can accumulate in the biocatalyst to increase buoyancy. This accumulated gas can reduce the energy consumption for a fluid bed operation and can facilitate the use of other bioreactor designs such as jet loop bioreactors.

The bioproduct may be recovered from the aqueous medium in any suitable manner including the Typical Separation Techniques.

B. Metabolic Shift

In a preferred embodiment of the invention, a phenotypic alteration occurs that results in a metabolic shift of the microorganisms in the biocatalysts. The metabolic shift can occur in each of anabolic and catabolic bioconversions. The metabolic shift results in less energy being consumed by the microorganisms for growth. Accordingly, where a substrate is used for both bioconversion to the bioproduct and for energy by the microorganisms, the metabolic shift enhances the bioconversion efficiency to the bioproduct. An additional type of metabolic shift is termed a carbon flow shift. A carbon flow shift occurs when a microorganism can produce more than one bioproduct from a substrate and the relative amounts of the bioproducts are altered. For instance, the fermentation of sugars by yeasts produce both ethanol and acetate anion. A carbon fow shift occurs when, e.g., the ratio of ethanol to acetate anion is increased. Similarly, in the production of butanol from sugars using *Clostridia acetobutyricum*, ethanol and acetone are co-produced and a carbon flow shift increases the ratio of butanol produced. A metabolic shift can be of significant economic benefit, especially in large bioconversion facilities and where the cost of the substrate is material such as where syngas or carbohydrate is the substrate. In metabolic systems where a carbon source needs to be provided to maintain the microorganisms, the metabolic shift beneficially reduces the amount of the carbon source provided to maintain a given rate of bioproduct production.

In more preferred embodiments pertaining to anabolic bioconversions of a carbon-containing substrate to bioproduct, at least about 95, preferably at least about 98, percent of the theoretical maximum bioconversion of the substrate to the sought bioproduct is achieved. For example, in the bioconversion of glucose to ethanol, carbon dioxide and ethanol are produced. The amount of ethanol produced as compared with the theoretical amount that would be produced if all the sugar were bioconverted to ethanol and carbon dioxide produced in the ethanol production pathway. Similarly, in the bioconversion of carbon monoxide, the theoretical maximum conversion to ethanol is that 6 moles of carbon monoxide produce 1 mole of ethanol and 4 moles of carbon dioxide (carbon dioxide, of course, can be bioconverted to ethanol in the presence of hydrogen).

In addition to a metabolic shift, the biocatalysts of this invention undertake a cryptic growth which is believed to be enabled by phenotypic alterations and communication among the microorganisms. The cryptic growth aids in providing a biocatalyst that does not generate solid debris. Nevertheless, the ability of the biocatalysts of this invention to maintain a stable population of microorganisms over extended periods of time evidences that a phenotypic metabolic shift occurs in the population of microorganisms.

C. Enhanced Bioconversion

In another preferred aspect of the invention, the biocatalysts exhibit an enhanced rate of bioconversion as compared to that of planktonic microorganisms having the same cell density per unit volume of bioreactor, all else being substantially the same. This aspect of the invention provides for improved anabolic and catabolic bioconversion processes due to the greater bioactivity. In some instances, the microorganisms may undergo a phenotypic alteration such that a bioconversion is observed that does not occur in planktonic growth.

Moreover, since often higher cell densities can be provided by the biocatalysts of this invention than with planktonic growth in free suspension or supported biocatalysts, even greater increases in bioconversion activity can be obtained per unit volume of bioreactor or per given unit of hydraulic retention time. Hence, reduced residence times for either batch or continuous processing can be achieved per unit of bioconversion.

The use of the biocatalysts of this invention also enables substrate in feed streams to be reduced to very low concentrations and also enables very low concentrations of substrate to be metabolically bioconverted. In some applications it is desired for a bioconversion process to reduce a substrate to very low concentrations, e.g., for efficient use of the substrate or such that the bioconversion effluent need not be further treated to remove the substrate. Examples of the latter are municipal wastewater where the effluent should contain little, if any, biodegradable carbon compounds, and reducing toxic materials such as 1,4-dioxane, N-nitrosodimethylamine (NDMA) and perchlorate anion and endocrine disrupters contained in water to concentrations of parts per billion or less. Other examples are components that affect taste and odor in drinking water affected by algal blooms such as methylisoboreal (MIB) and geosmin that may only be present in micro-concentrations. Thus, one embodiment of processes of this invention pertains to reducing the concentration of ultra-low contaminants (contaminants in a concentration less than about 50 micrograms per liter) in a water stream comprising:

a. continuously passing, said water stream to a bioreactor, said bioreactor being maintained at metabolic conditions including the presence of biocatalyst of this invention containing microorganisms capable of bioconversion of said ultra-low contaminants irreversibly retaining therein;
b. contacting said water stream with said biocatalyst for a time sufficient to reduce the concentration of said ultra-low contaminants; and
c. withdrawing from said bioreactor a treated water stream having a reduced concentration of said ultra-low contaminants.

Preferably, each of the ultra-low contaminants is present in a concentration in the water stream the passed to the bioreactor in an amount of at least about 10, say at least about 50, nanograms per liter (ng/L) and less than about 50, often less than about 20, micrograms per liter (mcg/L). Preferably at least about 50, and sometimes at least about 80 or 90, percent of the contaminant in the water stream is bioconverted.

The interior microenvironments and phenotypic changes in the biocatalysts of this invention, in another preferred aspect of this invention, also provide for enhanced, simultaneous bioconversion of two or more substrates by a single microorganism species. Usually microorganisms prefer or metabolize one substrate over another in a phenomenon known as diauxie. In accordance with this aspect of the invention, the bioconversion rate of the less preferred substrate is less depressed at the same mole ratio of more preferred to less preferred substrate than that in a planktonic process using the same microorganism and cell density and substantially the same process conditions. One example of diauxie is the treatment of water containing nitrate and perchlorate anions where the nitrate anions are the preferred substrate.

The biocatalysts of this invention contain microenvironments that can possess different conditions than those external to the biocatalyst. Thus, microenvironments in the interior of the biocatalysts enable both aerobic and anaerobic bioconversion processes to occur, even using the same microorganism. Thus, for instance, ammonium cation can be oxidized and the resulting nitrate anion reduces to nitrogen in an aerobic aqueous medium. The metabolic conditions in a given microenvironment may be affected by other metabolic activity within the biocatalysts. For instance, metabolizing an electron donor such as a carbon source, may consume oxygen and thus provide a reducing environment.

The biocatalysts can serve to provide a self-modulation and enable metabolic activity that would not be possible in a planktonic growth in a free suspension. This phenomenon is readily appreciated for redox type bioconversions. Consequently, metabolic processes that are reductions of substrates may proceed in the presence of oxygen or oxidizing components in an aqueous medium surrounding the biocatalyst. By way of example, and not in limitation, the biocatalysts can be used for catabolysis of hydrocarbons, such as aliphatic and aromatic hydrocarbons of 1 to 50 or more carbons, including alkanes, alkenes, and alkynes, and aromatics such as benzene, toluene and xylene; ethers, ketones, aldehydes, alcohols, carboxylic acids and esters of 1 to 50 or more carbons; halogenated hydrocarbons such as brominated and chlorinated hydrocarbons including perchloroethylene, dichloroethylene, vinyl chloride, trichloroethane, trichloroethylene, methylene chloride, chloroform, carbon tetrachloride and polychlorinated biphenyls (PCB's), and soluble metal and semi-metal compounds including nitrates, nitrites, sulfates, sulfites, phosphates, phosphites, and other metalates.

D. Enhanced Toxin Tolerance

Surprisingly, the biocatalysts of this invention exhibit an increased tolerance to toxins. While not wishing to be limited to theory, it is believed that some potential reasons for this increased tolerance, in addition to providing an environment where the microorganisms are metabolically retained and physically protected, could reside in the fact that the biocatalyst provides an environment where the microorganisms have time to react to the presence of the toxins to develop an internal resistance; the ability of the microorganisms to have increased cell wall stability and cell geometric stability; and the communication among the population of microorganisms to enhance the ability of the community to react and develop resistance mechanisms to the toxins. The exhibited tolerance is greater than that exhibited by planktonic microorganisms and sometimes is greater than that exhibited by conventional immobilized biofilms. Hence, a phenotypic shift by the microorganisms and their community may also contribute to the enhanced tolerance to toxins.

In some processes, especially anabolic processes, the bioconversion product (bioproduct) itself is toxic to the microorganisms or a co-product or by-product is produced that is toxic to the microorganisms. For example, the bioconversion of sugars to ethanol with yeast in a free cell, batch fermentation bioreactor is typically limited to a concentration of ethanol of about 15 percent. With the bioproduction of isobutanol or n-butanol from sugars, the maximum fermentation broth concentration is generally about 2.5 percent. Thus, the titer of bioproduct in the fermentation broth has to be limited to avoid deleterious concentrations of bioproduct, and the energy required for separation of the bioproduct increases. Moreover, with batch processes, the limitation on titer results in shorter cycle times. Hence, increased costs per unit volume of bioproduct are incurred including those associated with downtime of the bioreactor, cleaning of the bioreactor and replacement of the population of microorganisms. The increased resistance of the microorganisms to toxicity in accordance with the processes of this invention enables higher concentrations of bioproduct to be produced and, for batch fermentation processes, reduces the frequency of shutdowns.

In other processes, toxins may be included as contaminants in the feedstocks providing the substrate to the microorganisms. Although pretreating feedstocks to reduce the concentration of these toxins to tolerable levels can be done, such pretreatment results in added capital and operating costs. One particularly attractive application for the biocatalysts of this invention is in treating brackish or saline water or brine to metabolize other components in the water. The water may be from surface, ground or industrial sources. Examples of components that may require degradation in such waters include, but are not limited to nitrates, nitrites, chlorates, perchlorates, halogenated organics including but not limited to chlorinated solvents and PCB's, hydrocarbons including but not limited to aliphatic and aromatic hydrocarbons and oxygenated hydrocarbons such as 1,4-dioxane, carboxylic acids, ethers, ketones and aldehydes.

In some instances, the substrate itself may have an adverse effect on the microorganisms when present in too high of a concentration. Reducing the concentration of the substrate, e.g., by dilution, adds to the capital and operating costs of the metabolic process. Examples of substrates that can be toxic include carbon monoxide, hydrogen cyanide, hydrogen sulfide, permanganate, and oxygenated organic compounds where used to make other bioproducts.

Another toxin affecting microorganisms includes viruses, or phage. Treatment of aqueous media suffering from phage is problematic. The bioreactor can be emptied, sterilized, and then repopulated which incurs significant downtime as well as operating expense. In some instances, additives can be provided to the aqueous media as antiviral agents. This again increases the costs of the metabolic process.

In the broad aspects, the processes for bioconverting a substrate contained in an aqueous medium to bioproduct under bioconversion conditions including the presence of microorganisms for said bioconversion, wherein the aqueous medium contains at least one toxin in an amount sufficient to have a deleterious effect if said microorganisms were freely suspended in said aqueous medium under said bioconversion conditions, comprise attenuating the effect of the toxin by using a biocatalyst of this invention in the bioconversion process.

In some instances, the rate of bioconversion of the substrate to bioproduct is not significantly reduced, all other parameters remaining the same, when the concentration of bioproduct in the fermentation broth is about 20, frequently about 30, say about 50, or more percent greater than that achievable using a free cell suspension of the microorganism. Where used to bioconvert sugar to ethanol, ethanol concentrations in the fermentation broth of 20 mass percent or more can often be achieved. For the bioconversion of sugar to isobutanol or n-butanol, bioproduct concentration in the fermentation broth of at least about 3, and sometimes between about 3.5 and 5 or more mass percent, can be achieved.

In many instances, the microorganisms are able to withstand concentrations of the toxins at least about 20, and preferably at least about 30, percent greater than said microorganisms in free suspension in said aqueous medium. In many instances, the increased tolerance of the processes to the presence of toxins can be observed using a Batch Toxin Tolerance Test (BTT Test) defined above. The processes of this this invention exhibit in a BTT Test a bioconversion of at least about 20 percent, preferably at least about 30 or 50 percent, greater than that using the free suspension. In some instances the microorganisms are able to withstand concentrations of the toxins at least about 10, and preferably at least about 20, percent greater than said microorganisms in the form of a biofilm on a bone char support, all other conditions being the same.

In many instances, even when the concentrations of the chemicals reaches levels where the bioconversion rate exhibited by the biocatalyst is materially affected, the processes of this invention tend to provide protection to at least a portion of the microorganisms metabolically retained in the biocatalyst. Thus, upon the termination of the excursion into regimes where the microorganisms are adversely affected, bioconversion activity recommences evidencing survival of at least a portion of the population of the microorganisms providing the sought metabolism. Where a portion of the population is adversely affected during the excursion, the population of the microorganisms in the biocatalyst can increase after the termination of the excursion to a steady-state level.

In examples 205 to 207 a continuous stirred tank bioreactor having a working volume of 7 liters is used for batch experiments. The bioreactor is provided with controls to maintain temperature. The pH of the fermentation broth is controlled, typically to a pH of about 5. The fermentations are conducted in a batch mode. A 1000 milliliter solution of 223 grams of sugar in the form of honey per liter is charged to the batch bioreactor. The honey has a composition of about 38 mass percent fructose, 31 mass percent glucose, 7.31 mass percent maltose, 1.3 mass percent sucrose, 1.5 mass percent higher sugars and about 17 percent water with the balance being non-sugar components. The fermentations are conducted at about 30° to 35° C. In all examples, the same strain of *Saccharomyces cerevisiae* is used. The biocatalyst used is substantially that prepared in accordance with Example 25 has a Hydration Expansion Volume of about 70,000. The biocatalyst is contacted with dilute aqueous ethanol (varying between about 5 and 10 mass percent) for about two days prior to use.

Example 205

In this example, the batch bioreactor is used, and industrial grade ethanol is added to the fermentation broth to provide a 20 mass percent concentration of ethanol. A run uses a free suspension of *S. cerevisiae* to provide about 150 grams of yeast per liter, and another run uses sufficient biocatalyst to provide about 150 grams of yeast per liter. After 72 hours under fermentation conditions, the fermentation broth containing the free suspension yields no ethanol whereas the biocatalyst produces about 75 percent of the amount of ethanol theoretically possible. In the absence of the added ethanol, the free suspension provides after 72 hours a production of ethanol that is about 78 percent of the amount of ethanol theoretically possible. The biocatalyst produces an amount of ethanol between about 96 and 98 percent of that theoretically possible. The high conversion evidences that a metabolic shift occurs.

Example 206

In this example, for a period of about 24 hours, the biocatalyst is exposed to a 20 percent by mass aqueous ethanol solution. The biocatalyst is then washed and then used in the batch bioreactor to provide a theoretical yeast content of about 150 grams per liter. After 72 hours, the free cell batch reaction does not generate any ethanol. The batch reaction using the biocatalyst yields about 98 percent of the ethanol theoretically possible.

Example 207

In this example the amount of honey added to the fermentation broth is increased to provide about 288 grams per liter of sugar. Several batch reactions are conducted using about 150 grams per liter of *S. cerevisiae* contained in biocatalyst. After 72 hours, the batch reactions using the biocatalyst yields between about 96 and 99 percent of the ethanol theoretically possible.

Example 208

This example demonstrates the resistance of *Rhodococcus* to various concentrations of ethanol where the microorganism is in a biocatalyst of this invention. Approximately 20 grams of biocatalyst substantially as prepared in example 169 are placed in a serum bottle for each batch test. A total of 7 serum bottles are prepared. About 80 milliliters of solution containing ethanol are placed in each serum bottle. The solution for each bottle is at a different ethanol concentration. Each solution is prepared using absolute ethanol and the various solutions contain 0, 10, 20, 35, 50, 80 and 100 volume percent ethanol. The contact between the solution and the biocatalyst is at room temperature (about 22° C.) for 24 hours. After which time, the biocatalyst in each serum bottle is washed. The biocatalyst from each serum bottle is evaluated for oxygen up-take, thereby indicating the viability of the microorganisms. This evaluation is conducted by placing the biocatalyst in a 100 milliliter flask and pouring about 80 milliliters of distilled water that has been aerated to saturation into the flask. Oxygen probe measurements are taken each 15 minutes. All biocatalysts survived the immersion in ethanol and in comparison to the control with no ethanol, all substantially recovered their bioactivities as evidenced by oxygen up-take. In a control experiment, no microorganisms survive the addition of 5 volume percent ethanol to a free suspension containing the microorganisms.

E. In-Situ Sterilization

It may be desired to add toxins to the medium containing the microorganisms to control the population of undesired microorganisms that may compete for nutrients or may provide undesired metabolites. In some processes, such as the conversion of corn sugar to ethanol, the presence of adventitious or undesirable microorganisms is addressed by sterilization of batch reactors at the conclusion of each run. Continuous bioconversion processes, however, are not so amenable to frequent sterilization. Hence, continuous processes are typically monitored for undesired metabolites, or are monitored for the productivity of the sought bioproduct, and shut down for sterilization when required.

Removal of the adventitious microorganisms from water or other feedstock for catabolic or anabolic processes can be done, however, with increased capital and operating costs. The alternative is to periodically replace and replenish the sought microorganisms in the bioreactor used for the continuous processes. Another alternative is disclosed by Sumner, et al., in United States Published Patent Application 20090087897, where a stabilized chlorine dioxide is added preventatively in an amount effective to prevent growth of bacteria to a fermentation processes for making ethanol.

The biocatalysts of this invention enable controlling the presence of contaminating microorganisms due to the enhanced toxin resistance exhibited by the biocatalysts. These processes pertain to bioconverting a substrate contained in an aqueous medium to bioproduct under metabolic conditions including the presence of microorganisms for said bioconversion, wherein a toxin is provided to the aqueous medium in an amount sufficient to control contaminating microorganisms, wherein the microorganisms are retained in a biocatalyst of this invention.

The toxin used to control the contaminating microorganisms may be a bacteriostatic agent, a bactericidal agent or a bacteriolytic agent. Preferably the toxin is a disinfecting agent, and most preferably is an oxidizing agent. These preferred disinfecting agents are relatively inexpensive and include hydrogen peroxide, peracetic acid, aldehydes (especially glutaraldehyde and o-phthalaldehyde), ozone, and hypochlorite. The introduction of the toxin into the aqueous medium may occur in response to an undesired buildup of the population of contaminating microorganisms, or may be on a periodic schedule or continuously to control the build-up of contaminating microorganisms. The concentration of disinfecting agent added to the aqueous medium should be sufficient to either reduce or maintain the population of the contaminating microorganisms at a desired level.

Where hydrogen peroxide is the sterilizing agent, is usually introduced such that it is present in the aqueous medium in a concentration of between about 0.1 to about 5, preferably 0.5 to 3, mass percent. Where peracetic acid is used is the sterilizing agent, the amount introduced into the aqueous medium is generally sufficient to provide a concentration between about 0.1 to about 3, preferably 0.2 to 2, mass percent. Glutaraldehyde and o-phthalaldehyde are often used to provide a concentration in the aqueous medium of between about 0.01 to about 0.5 mass percent. Ozone can be bubbled through the aqueous medium in order to effect the reduction in the population of contaminating microorganisms. Hypochlorite anion is typically available as an aqueous solution of sodium hypochlorite. Typically the concentration of hypochlorite anion in the aqueous medium is between about 0.1 to 3, say, between about 0.2 to 2, mass percent.

The duration of the presence of the sterilizing agent in the aqueous medium should be sufficient in order to effect the desired reduction of the population of the contaminating microorganisms. In one embodiment a concentration of the sterilizing agent may be maintained by continuous basis in the aqueous medium and thus act as a preventative to the build-up of a population of contaminating microorganisms. In other preferred embodiments, the sterilizing agent is added intermittently when needed to control the population of the contaminating microorganisms. In the latter case, the duration of the maintenance of microorganism-killing concentrations of the sterilizing agent is typically less than about 20, and is often in the range of, 0.1 to 10, hours.

The control of the population of the contaminating microorganisms is most advantageously conducted under the same conditions that the metabolic process would be conducted. If desired, it is possible to use conditions different than those that would normally be used for the metabolic process provided that the conditions are not unduly deleterious to the microorganisms contained in the biocatalyst. Conditions typically include temperatures in the range of between about 5° to 60° C., and a pH the range of between about 5.0 and 8.5, say, 6 to 8. Preferably, the presence of nutrients and other adjuvants remain a concentration in the aqueous medium that substantially same as used for the bioconversion process.

Example 209

In this example water containing about 50 parts per million mass of nitrate anion per liter is continuously passed to a bioreactor containing biocatalyst having *Paracoccus denitrificans* ATCC® 17741 retained in the interior. The biocatalyst is prepared substantially as set forth in Example 101 and has a Hydration Expansion Volume of about 70,000. The biocatalyst provides about 150 grams of microorganism per liter in the bioreactor. The hydraulic residence time is about 600 minutes and the reactor is operated at about 25° C. The effluent water contains less than about 1 part per million mass of nitrate anion per liter. Sodium hypochlorite is added to the water to provide a concentration of 0.5 gram per liter, and sodium acetate is added at an amount approximately equivalent to 1.1 times the theoretical demand. The bioreactor is operated for 2 hours with this composition. The effluent water continues to contain less than about 5 parts per million mass of nitrate anion per liter. In additional runs, the biocatalyst is immersed for 24 hours at about 25° C. in an aqueous solution containing sodium hypochlorite at concentrations of 1.0 and 2.0 grams per liter before being used in the apparatus. These concentrations of sodium hypochlorite are considered lethal to planktonic microorganisms in free suspension as shown by a control experiment.

After immersion in the 1.0% concentration solution, the performance of the microorganisms is not affected and the water effluent continues to contain less than about 1 parts per million mass of nitrate anion per liter. Biocatalyst is removed and again immersed in the 1.0% solution for 24 hours. After the second immersion in the 1.0% concentration solution, the performance of the microorganisms is not affected and the water effluent continues to contain less than about 1 parts per million mass of nitrate anion per liter.

After immersion in the 2.0% concentration solution, the performance of the microorganisms is reduced to about 62 percent and the water effluent contains less than about 20 parts per million mass of nitrate anion per liter. Biocatalyst is removed and again immersed in the 2.0% solution for 24 hours. After the second immersion in the 2.0% concentration solution, the performance of the microorganisms is improved, and the water effluent contains less than about 4 parts per million mass of nitrate anion per liter.

F. Strain Stability

In preferred embodiments, the biocatalysts of this invention essentially contain in their interiors a single strain of microorganisms, i.e., are axenic. This provides for consistency in bioconversion performance, including bioconversion rate and selectivity, and thereby enhances the viability of commercial-scale processes. In addition, having a single strain of microorganism frequently enhances sociobiological behavior such as horizontal gene transfer, production of public goods, altruistic behaviors, taking up DNA of lysed same-strain cells, and the like, all of which can be beneficial to the biocatalyst and its performance.

Whether a metabolic process uses a wild state or modified wild state or genetically modified microorganism, several concerns exist including that automutation of the strain of microorganisms could lead to an adverse change in the population of microorganisms. Although automutation may occur inherently, the sociobiological behavior of the microorganisms, which behavior is enhanced in the biocatalysts of this invention, can mitigate or prevent untoward genotypic changes to the population. Additionally, in that the phenotypic changes of the microorganisms in the biocatalysts of this invention usually result in a metabolic shift, the rate of reproduction is reduced. Hence adverse automutation is more readily modulated by the population of microorganisms. Further, the biocatalysts tend to mitigate external inputs that may induce undesired automutations.

The biocatalysts of this invention are made with a high concentration of microorganisms, often substantially at the steady-state density of the microorganisms in the biocatalyst. Numerous advantages follow from this method. First, the essentially fully active biocatalysts can be made under conditions that assure strain purity. Second, scale-up is simplified as a plurality of batches can be made and then accumulated in a volume required for a commercial-scale bioreactor. Quality checks can be made with each batch. Third, the population of microorganisms in the biocatalyst can be sufficiently concentrated that sociobiological behaviors that prevent untoward automutation exist. Fourth, as the microorganisms are substantially irreversibly retained in the interior of the biocatalyst, any contaminating microorganisms would be constrained to a biocatalyst and not adversely affect the microorganisms in the other biocatalysts. Fifth, within a single biocatalyst structure, any contaminating microorganism will tend to be metabolically retained in a region with a constrained population, and the community of the intended strain of microorganisms is believed to communicate or interact to enhance competitive strength against invading microorganisms (territorial competitiveness) and to maintain strain uniformity. Sixth, the exo-network of the microorganisms in the biocatalysts facilitates horizontal gene transfer. And seventh, the biocatalysts provide a microenvironment that tends to assure stable microbial constituency.

In some embodiments the sought microorganism is less robust, and indeed, some, such as syntrophic microorganisms, may only be able to thrive in relationship with another microorganism and are typically difficult to obtain and maintain a pure culture even though the syntrophic microorganism may have the ability to effect the sought bioconversion to bioproduct. In some instances, the microorganisms in the biocatalyst may undergo adaptation and potential genetic alteration during use in a metabolic process. The communication and potential horizontal gene transfer provided by the biocatalysts of this invention and the exo-network facilitates uniformity of the microorganism strain within the biocatalysts.

G. Stasis Capability

The biocatalysts of this invention provide an internal environment that permits the microorganisms metabolically retained therein to effectively communicate. The communication also serves to assure that the community of microorganisms survives during periods where little or no nutrients are supplied to the biocatalysts, that is, the biocatalyst can enter into an essential state of stasis. The essential state of stasis as described in this section is with respect to the biocatalyst itself. It should be understood that with the high populations of microorganisms in a biocatalyst, microenvironments can exist where the microorganisms from time-to-time do not obtain nutrients. Hence, even while the biocatalyst is exhibit bioconversion activity, zones within the biocatalyst can be in essential stasis and regain bioactivity upon an increase in the supply of nutrients and substrates to the biocatalyst.

Heretofore, stasis of microorganisms has been obtained by storage at cool temperatures with reduced supply of nutrients or freezing. Maintaining such cool or freezing conditions can be expensive, especially for large volumes of microorganisms, and is subject to loss of power or mechanical breakdown, and can be deleterious to the population of the microorganisms.

The biocatalysts of this aspect of the invention can pass into a state of stasis not requiring the supply of nutrients and without costly storage conditions yet still with the microorganisms having an ability to rapidly achieve the desired biological activity upon start-up in a bioreactor. By maintaining the microorganisms in an essential state of stasis for extended periods of time, not only can the time interval between manufacture and start-up be tolerated, but also the microbial composites can be placed in simple containers for shipping such as sealed barrels, tanks, and the like without the addition of nutrients during the period of storage. Planned and unplanned shutdowns of a bioconversion process using the biocatalysts of this invention can be accommodated without loss of bioactivity. Because the microorganisms themselves modulate the stasis, no equipment or control system is required to protect the population of microorganisms or restart metabolic activity. In yet a further preferred aspect of the invention, the biocatalyst contains solid polysaccharide in its interior to even further enhance the ability of the biocatalyst to remain in a state of stasis for longer durations.

The conditions required for entry into stasis fall within a broad range. The temperature may be substantially that used for the metabolic process. The biocatalyst should have some degree of hydration during storage although it is not essential that the biocatalyst be immersed in an aqueous medium. Often the temperature ranges between about −10° C. to 50° C. or more, and most preferably between about 5° C. or 10° C. to 30° C. for purposes of energy savings and convenience. Although lower temperatures are generally preferred, higher temperatures still provide significant durations of stasis of the microorganisms in the biocatalysts of this invention. Where the microorganism is sensitive to oxygen, it is preferred, but sometimes not essential, that oxygen be excluded during storage.

Typically the biocatalyst can remain in a state of stasis for extended periods of time, e.g., at least about 1, often at least about 20, and sometimes greater than about 50 or 100, weeks. The bioactivity of the biocatalysts is regained upon subjecting the biocatalysts to metabolic conditions. Often essentially complete bioactivity is regained in less than 5, and sometimes less than 3, days.

Examples 210 to 215

In the following examples, various biocatalysts according to the invention are subjected to storage for the periods set forth in the below table and are then used for the intended metabolic process. Prior to being stored, the biocatalysts are used for the metabolic reaction for at least 2 days. The results are summarized in Table V.

TABLE V

| Example | Biocatalyst of Example | Metabolic Process | Duration of Storage, days | Days to recover bioactivity |
|---|---|---|---|---|
| 210 | 9 | Glucose to ethanol | 30 | 1 |
| 211 | 52 | Nitrate to nitrogen | 350 | 3 |
| 212 | 110 | 1,4-Dioxane degradation | 365 | 7 |
| 213 | 116 | Perchlorate to chloride | 700 | 3 |
| 214 | 92 | Municipal wastewater treatment | 90 | 1 |
| 215 | 146 | Glucose to Lactic Acid | 300 | 5 |

H. Photosynthetic Processes

The biocatalysts of this invention can be used in photosynthetic processes. The biocatalyst contains one or more suitable photosynthetic microorganisms including bacteria, algae, yeasts and molds having biocatalytic activity activated by light radiation. Preferably the microorganism is an algae, most preferably a microalgae, or cyanobacteria. In some instances *Botryococcus* is desired due to organic compound productivity. The biocatalyst may contain luminescent components as described above, but such components are not critical to the use of a biocatalyst in a photosynthetic process.

Photo-bioconversion conditions are maintained for conversion of at least one substrate to the sought bioproduct including conditions of temperature, pressure, oxygenation, pH, and nutrients and additives. The bioconversion may be on a continuous, semi-continuous or batch mode of operation. Reactor designs include, but are not limited to, Typical Bioreactor Systems provided that access is provided to provide light energy to the biocatalyst. The biocatalyst is freely mobile in the in the culture liquid. More than one reactor vessel may be used. For instance, reactor vessels may be in parallel or in sequential flow series. The processes and apparatus of this invention may use land-based reactors, or the reactors may be adapted to float on a body of water such as a reservoir, river, lake, or ocean. The floating reactors can be adapted to take advantage of the natural temperature moderation of the body of water, and, in some instances, natural movements of the body of water may assist in the agitation.

The bioreactor may be open, e.g., as a pond or raceway, or closed. The light source may be any suitable light source but preferably sunlight provides at least a major portion of the light radiation of step (c), often at least about 75, say, at least about 90, percent, and sometimes essentially all, of the light radiation is from sunlight. Since the biocatalysts provide at least some UV protection to the microorganisms, lenses, mirrors, moving arrays that follow the sun and the like may be used to enhance the intensity of the light ° radiation contacting the culture liquid. Moreover, the biocatalyst may provide protection to microorganisms that are susceptible to bleaching or death in the presence of high intensity light.

The photo-bioconversion conditions, rate of substrate supply and the density of the microorganisms in the culture liquid can influence bioconversion. Accordingly, for a given system of biocatalysts, substrates and bioproducts, productivities can vary widely. In some instances, the biocatalysts used in the processes of this invention can facilitate maintaining desired microorganism densities in the culture liquid and thus facilitate high productivities per surface area exposed to light radiation. In some instances, it may be desired to provide periods of darkness to the photosynthetic microorganisms where such periods enhance the productivity of the microorganisms.

The culture liquid in the bioreactor may be substantially stagnant, but preferably is subjected to forces to provide movement to the culture liquid. Most preferably the movement of the culture liquid is sufficient to cause movement of the biocatalyst to and from the region receiving the light radiation ("direct contact area") of the culture liquid.

Examples of substrates include, but are not limited to, carbon dioxide, carbon monoxide, hydrogen, methane, ethane, propane, hydrogen sulfide, carbonyl sulfide, mercaptans, ammonia, lower alkylamines, phosphines, and mixtures thereof. Syngas (synthesis gas) is an often proposed gaseous substrate for anaerobic bioconversions. Carbohydrates, including sugars and polysaccharides, may find application as substrates. Lipids may also find utility as substrates. Other substrates include, but are not limited to, aliphatic and aromatic molecules. Aliphatic (including cycloaliphatic) and aromatic substrates include, but are not limited to hydrocarbons of from, e.g., about 1 to about 44 or 50 carbon atoms which may contain hetero atoms, e.g., oxygen, sulfur, phosphorus, and nitrogen, and which may be substituted, e.g., with acyl, halogen, hydroxyl, amine, amide, thiol, nitro, or phosphine groups.

The photo-bioconversion conditions, rate of substrate supply and the density of the biocatalysts in the fermentation broth can influence the productivity of the culture liquid to produce bioproducts. Accordingly, for a given system of biocatalysts, substrates and bioproducts, productivities can vary widely. In some instances, the irreversibly retained biocatalysts used in the processes of this invention can facilitate maintaining desired biocatalyst densities in the culture liquid and thus facilitate high productivities per surface area exposed to light radiation. In some instances, it may be desired to provide periods of darkness to the photosynthetic microorganisms where such periods enhance the productivity of the microorganisms.

The recovery of the bioproduct from the culture liquid may be effected by any suitable unit operation or unit operations including Typical Separation Techniques. The culture liquid may be removed from the reactor for bioproduct recovery or the bioproduct recovery may be effected in the reactor. In the latter case, separation may be by evaporation, e.g., with lower vapor pressure organic compounds such as ethanol, or phase separation as with, e.g., higher molecular weight organic compounds such as aromatic or aliphatic hydrocarbons, alcohols, ethers, and esters (for instance, glycerides) of 6 or more carbons. Where the culture liquid is removed from the reactor for bioproduct recovery or purge, any suitable unit operation may be used to retain the biocatalyst in the reactor such as, but not limited to, decanting (where the density of the biocatalyst is greater or less than that of the culture liquid), filtration, centrifugation, and the like. If desired, especially where the biocatalytic activity of the biocatalyst is observed to be decreasing, a portion of the biocatalyst may be removed and replaced to provide for a continuously operating facility.

Figure 3:
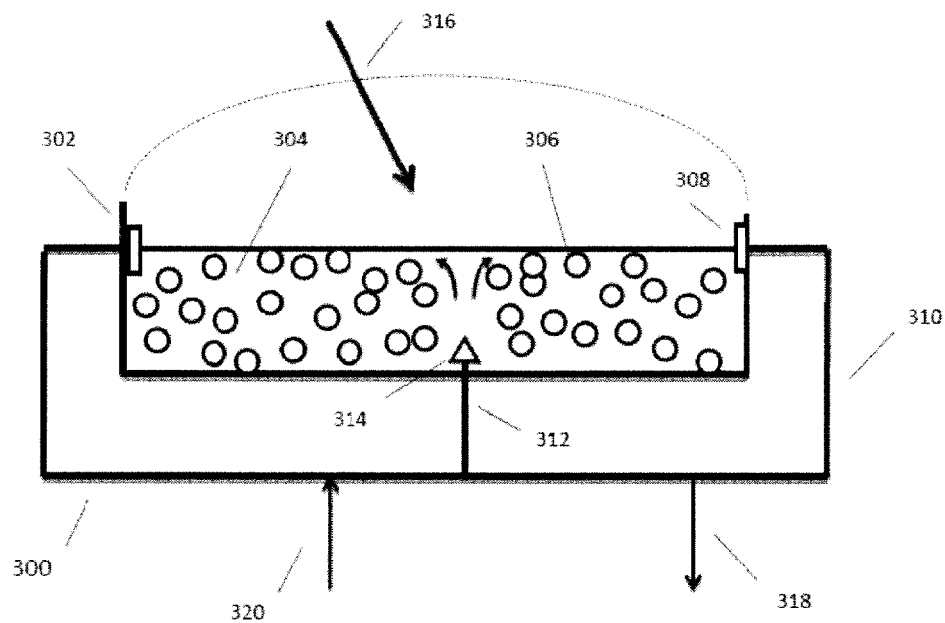
FIG. 3 is a schematic depiction of a photo-bioreactor using biocatalysts in accordance with this invention.

For purposes of facilitating the understanding of the processes and apparatus of this invention and not in limitation thereof, reference is made to FIG. 3 which depicts a cross section of a portion of a reactor 300. Reactor 300 comprises reactor vessel 302 has a clear polymeric cover at its top represented by the dotted line and contains culture liquid 304. A plurality of biocatalyst particles 306 containing cyanobacteria and phosphorescent material are dispersed within culture liquid 304. Carbon dioxide is used as the substrate to make ethanol in reactor 300.

As depicted, culture liquid and off gas are recycled. Screen filter 308 is provided to prevent removal of biocatalyst and permit off-gas and culture liquid to be drawn from reactor vessel 302. The fluid passes through line 310 for recycle via line 312 and distributor 314 for return to reactor vessel 304. Distributor 314 is adapted to provide for movement of biocatalyst 306 to the surface of culture liquid 304 to receive radiation 316 from a radiation source. While an external radiation source is depicted, alternatively or in addition, internal radiation sources could be used. A draw stream of recycling culture liquid is taken via line 318 for product recovery. Make up culture liquid is provided via line 320. The make-up culture liquid contains dissolved carbon dioxide. If desired, ammonium carbonate may be used to supply both carbon and nitrogen to the microorganisms.

I. Representative Metabolic Process Discussions

The biocatalysts due to the microenvironments in the biocatalyst, communication among the microorganisms and the phenotypic alterations undergone by the microorganisms provide a number of process-related advantages including, but not limited to, no solid debris being generated,
the potential for high densities of microorganisms in a bioreactor,
stable population of microorganisms and bioactivity over extended periods of time,
metabolic shift towards production rather than growth and carbon flow shift,
ability to undergo essential stasis for extended durations,
ability to quickly respond to changes in substrate rate of supply and concentration,
attenuation of diauxie,
enhanced control and modulation of pH and redox balances in the microenvironment of the biocatalyst,
greater tolerance to substrate, bioproduct and contaminants,
ability to bioconvert substrate at ultralow concentrations,
ability to use slower growing and less robust microorganisms and increased resistance to competitiveness,
enhanced strain purity capabilities,
ability to be subjected to in situ antimicrobial treatment,
ability to quickly start a bioreactor since the population of microorganisms required at full operation is contained in the biocatalyst,
ability to contact biocatalyst with gas phase substrate, and
ease of separation of bioproduct from biocatalyst thereby facilitating continuous operations.

In the following discussions pertaining to certain of the many uses of the biocatalysts of this invention, some or all these process-related advantages provide significant improvements over existing processes. A recitation of these process-related advantages as they pertain to each of the below described processes is not repeated for each and is to be imputed for each of the processes.

Additionally, it is to be understood that biocatalyst options such as the incorporation of sorbents, polysaccharide, and phosphorescent materials (for photosynthetic processes) can be used with any of the below described processes. Further, process steps such as in situ sterilization, gas phase bioconversion and photosynthetic reactor configuration (for photosynthetic processes) can be used with any of the below described processes. It is to be understood for the below discussions that the cell concentrations in a bioreactor will depend upon the concentration of the biocatalyst in the bioreactor as well as the concentration of cells within the biocatalyst.

The unique properties of the biocatalysts of this invention enable many metabolic processes. Below are described some of the processes providing advantageous bioconversions. Figures used to describe the processes are not in limitation and omit minor equipment such as pumps, compressors, valves, instruments and other devices the placement of which and operation thereof are well known to those practiced in chemical engineering and omit ancillary unit operations.

i. Municipal Wastewater

Municipal wastewater typically contains dissolved organics (BOD and (COD), solids (Total Suspended Solids, TSS), and various ions including ammonium cation and phosphorus-containing anions. Release of municipal wastewater into the environment results in numerous adverse effects. Nitrogen and phosphorus are the predominant contributors to eutrophication of surface waters. These nutrients can also lead to algal blooms. The algal blooms can cause taste and odor problems when the water is to be used for drinking purposes. Other biochemical activities that may be stimulated by overenrichment of surface waters include the stimulation of microbes that can pose risks to human health.

Municipal wastewater treatment systems generally have a plurality of operations including three treatment stages of processing. The primary treatment separates solids from liquids. Where the wastewater contains immiscible, low density liquids such as fats and oils, these liquids are skimmed off, and the remaining liquid is passed to a secondary treatment which usually uses microorganisms to substantially degrade under aerobic conditions biodegradable soluble organic contaminants. At the completion of the secondary treatment, solids from these microorganisms are separated by settling, and the liquid is passed to the tertiary treatment prior to discharge. Not all municipal wastewater treatment facilities employ tertiary treatment. Accordingly, the effluent can contain significant amounts of nitrogen compounds.

Tertiary treatment can include the removal of nitrogen. Ammonium cation may be first subjected to a nitrification to produce nitrite and then nitrate, e.g., in the presence of *Nitrosomonas* spp. and then *Nitrobacter* spp. Denitrification requires anoxic conditions and electron donor. Hence, some facilities add a donor such as methanol or even raw sewage. Often over 4 kilograms of oxygen are consumed per kilogram of ammonium nitrogen removed, and the nitrification and denitrification processes and increase power consumption for a typical facility by 30 percent or more. Solids are generated by the microorganisms and are removed at the completion of the tertiary treatment before discharge of the treated water.

Typical municipal wastewater treatment facilities must treat 4 or 5 million liters of raw sewerage per day, and some facilities treat upwards of 1 billion liters of municipal waste water per day. Due to these large volumes and the time required to effect the sought biodegradation, a plurality of parallel treatment units are required to handle these substantial flow of municipal wastewater. The secondary and tertiary treatments require an aerobic environment. Efforts to reduce the residence time for treatment for these aerobic include bubbling air through the wastewater. The use of oxygen-enriched air or oxygen provide further reductions in the cycle time, i.e., the duration required to achieve the sought reduction in organic carbon and ammonium cation. Even so, the hydraulic retention time of the water being treated in a secondary or tertiary treatment operation is often in excess of at least 16 hours, say, between about 18 and 30, hours with a sludge retention time that can be from 10 to 30 days. This significant hydraulic retention time necessitates the use of large reactors. Generally, the reactors are operated in a batch mode. Accordingly, multiple reactors are required in order to sequence patches such that the municipal wastewater treatment facility can handle a continuous incoming stream of wastewater. A plurality of settling ponds is required to effect separation of the solids (sludge) from secondary and tertiary treatments. And the sludge must be disposed in an environmentally appropriate manner.

An additional challenge facing tertiary treatments is that the microorganisms are sometimes not stable, whether due to the presence of adventitious competitive microorganisms or changes in conditions or the composition of the wastewater.

Hiatt in U.S. Pat. No. 6,025,152 discloses a mixture of bacteria that are reported to be able to oxidize ammonia and nitrites, organic amines and organonitriles and aerobically reduce nitrates to molecular nitrogen. The anammox process has been proposed for removal of ammonia under anaerobic conditions. In this process anammox bacteria oxidize ammonium under anoxic conditions with nitrite as the electron acceptor. Typically the anammox process is conducted with a low ratio of carbon source to nitrogen so as to retard the population growth of heterotrophic denitrifying bacteria. The anammox bacteria are very sensitive to the presence of oxygen, thus posing another challenge for use in municipal wastewater treatment.

Processes are provided in this aspect of the invention for the treatment of municipal wastewater wherein the water from the primary treatment is continuously passed to a bioreactor that effectively catabolizes organic carbon to carbon dioxide and ammonium cation to nitrate anion. The bioreactor generates essentially no solids that pass to the treated water, thus eliminating the need for any additional sludge separation operations and sludge disposal from such operations. Moreover, the sought bioconversion of organic carbon and ammonium cation can often be completed with a relatively short hydraulic retention time, often, less than about 12, and in preferred aspects, less than about 6, hours. The short hydraulic retention times enable a small footprint bioreactor to be used, and since the processes continuous, a plurality of large bioreactors otherwise required to operate in a batch mode is not required. These relatively short hydraulic residence times can be obtained without the need to use oxygen-enriched air or oxygen. Preferably the dissolved oxygen concentration in the wastewater stream during contact with the biocatalyst is at least about 1 milligram per liter and preferably between about 2 to 3, milligrams per liter to save on aeration costs. Further, the concentration of oxygen in the wastewater need not be high to achieve the short hydraulic retention times, and the short hydraulic retention times reduce the amount of energy required to aerate the wastewater for a given reduction in ammonia and organic carbon.

In the broad aspects of this aspect of the invention, processes for catabolizing dissolved organic carbon and ammonium cation in a wastewater stream comprise:

a. continuously passing said wastewater stream to a bioreactor containing biocatalyst of this invention having substantially irreversibly retained therein microorganisms capable of catabolizing dissolved organic carbon to carbon dioxide and ammonium cation to nitrate anion, preferably an ammonia-oxidizing microorganism;

b. contacting in said bioreactor said wastewater stream with said biocatalyst in the presence of oxygen for a time sufficient to provide an oxidized effluent containing less than about 5, preferably less than about 1 ppm, by mass of ammonium cation and having a reduced biochemical oxygen demand (BOD), preferably less than about 10, preferably less than about 4, milligrams per liter, wherein substantially no solids pass from the biocatalyst to the oxidized effluent.

If desired, the oxidized effluent is subjected to subsequent unit operations, e.g., for the bioconversion of nitrate to nitrogen and for the removal of phosphorus. Preferably the denitrification is conducted using biocatalyst of this invention having substantially irreversibly retained therein microorganisms capable of denitrifying nitrate anion, preferably a heterotrophic denitrifying microorganism. By substantially irreversibly retaining denitrifying microorganisms in the biocatalyst of this invention, the wastewater being treated need not be deaerated to obtain high denitrifying bioactivity.

One advantage of a sequential nitrifying and denitrifying unit operations in accordance with this aspect of the invention is that carbon source for the denitrification can be controlled to meet the stoichiometric requirement for the denitrification without resulting in an increase of COD in the effluent. The organic carbon from the nitrification operation may vary depending upon the composition and rate of introduction of the wastewater to the nitrification operation and the operation of the nitrification operation to achieve the sought reduction in ammonium cation concentration. Consequently, the COD in the water from the nitrification operation may be over about 5, preferably less than about 20, milligrams per liter. This organic carbon thus offsets any required carbon source for the denitrification.

In another preferred embodiment of this aspect of the invention at least a portion of the solids contained in the waste water being processed, e.g., debris from indigenous microorganisms, is hydrolyzed and degraded to further reduce BOD and TSS in the effluent. Typically these solids tend not to adhere to the biocatalyst, especially biocatalysts having a skin, due to the currents of water passing through the bed of biocatalyst. By reducing the velocity of the water being treated, e.g., as would happen as the water emerges from the biocatalyst bed or by providing an expanded section, at least some of the solids are disentrained from the water an can be subjected to hydrolysis for extended periods of time. The carbon values from the hydrolysis of the debris become dissolved in the treated water and are passed to a subsequent bioreactor for degradation of carbon values. The retention of solids may occur at numerous points in the processes of this invention. For instance, the nitrification operation may contain two or more bioreactors in series and the hydrolysis occurs between the beds of biocatalyst in these bioreactors. Similarly, the retention of solids for hydrolysis may occur between nitrification and denitrification operations.

Since the processes of this invention use biocatalyst in which the microorganisms are retained and have an ability to retard or exclude the entry of indigenous microorganisms, the selected microorganism can be targeted to the sought activity, and the biocatalyst often contains a substantially pure strain of the microorganisms, thereby enabling higher bioactivity to be achieved than that which can be obtained using indigenous microorganisms or activated sludge.

The raw wastewater may be from any source although the processes of this invention are particularly useful for treating municipal wastewater. The raw wastewater typically has a BOD of between about 50 or 100 and 600 or more milligrams of oxygen per liter. The COD of the wastewater is greater than the BOD and is often substantially greater, e.g., even up to 5000 or more milligrams per liter. The ammonium cation content of the raw wastewater can also vary over a wide range and is often between about 10 and 700, more frequently between about 25 and 200, milligrams per liter. The raw wastewater may contain other components including, but not limited to, sulfur compounds, phosphorus compounds, inorganic salts and solubilized metals.

Preferably, the wastewater to be treated contains less than about 200, and often less than about 100, grams per liter of solids having a major dimension greater than about 10 microns. If desired, the wastewater can be subjected to ultrafiltration to remove substantially all competitive microorganisms prior to being passed to the aerobic bioreactor.

Wastewater is passed to at least one aerobic bioreactor containing biocatalyst for the bioconversion of organic carbon to carbon dioxide and ammonium cation to nitrate anion. The water in the aerobic bioreactor contains dissolved oxygen. Preferably the dissolved oxygen concentration in the wastewater stream during contact with the biocatalyst is at least about 2, say, at least about 3 or more, milligrams per liter. Conveniently, the oxygen is supplied by air or oxygen-enriched air. The oxygen may be supplied by any convenient means including by bubbling or sparging oxygen containing gas through the water or agitating or otherwise mechanically treating the water such as by spraying to facilitate water-gas contact. Oxidizing components include, but are not limited to, peroxide and percarbonate. The environment provided by the biocatalyst can serve to protect the microorganisms retained therein from the effects of peroxide, percarbonate, and other oxidizing components. Where such oxidizing components are used, the concentration of active oxygen is preferably in the range of between about 1 and 10, more preferably, between about 1 and 5, milligrams per liter. In general, Typical Mesophilic Conditions are used. For most municipal wastewater facilities, the other conditions of the aerobic treatment are typically those defined by ambient conditions.

The aerobic bioreactor may be in any suitable configuration including Typical Bioreactor Systems, preferably suitable for continuous operation. Often the cell density is at least about 100, preferably at least about 200, and sometimes between about 400 and 800, grams per liter.

The duration of the contact between the wastewater and the biocatalyst during the aerobic treatment in the bioreactor is sufficient to provide the desired reduction of metabolizable organic carbon and ammonium cation. The duration will thus depend upon the concentration of the organic carbon and ammonium cation in the wastewater, the desired reduction, and the density of microorganisms in the bioreactor as well as the conditions employed. Relatively low average hydraulic retention times can be realized. The average hydraulic retention time in some instances is less than about 6, and most preferably less than about 4, hours. Thus the bioreactor can be relatively compact, i.e., provide low footprint, yet handle high volumes of wastewater to be treated.

If desired, the oxidized effluent may be filtered. The oxidized effluent may be discharged from the wastewater treatment system, but since it contains nitrate anion, it is usually subjected to a process to reduce nitrate anion to nitrogen. Any suitable denitrification unit operation may be used. A particularly advantageous denitrification unit operation uses biocatalyst of this invention having substantially irreversibly retained therein denitrifying microorganisms such that no sludge is generated that needs to be removed from the process.

As stated above, the denitrification may be conducted in the same bioreactor in which nitrification is occurring or in a separate bioreactor. The denitrification unit operation may be incorporated into the aerobic treatment to catabolize organic carbon and ammonium cation. One such process uses biocatalyst of this invention containing microorganism capable of both nitrification and denitrification discussed elsewhere herein. Alternatively, biocatalyst of this invention containing denitrification microorganisms can be intermixed with the biocatalyst for the oxidation. It is believed that the microenvironments provided by the biocatalyst generate anaerobic conditions then enable the denitrification to occur. Most often, the removal of nitrate anion is conducted in a separate unit operation. Where the concentration of nitrate anion is low, the use of ion exchange resins may be feasible. Chemical reduction processes have also been proposed, e.g., using sulfur dioxide or other reducing agent. However, most municipal wastewater facilities that remove nitrate anion use metabolic processes under anoxic or anaerobic conditions and activated sludge. The denitrified effluent typically contains less than about 1, preferably less than about 0.01, milligrams of nitrate anion per liter.

Typical denitrifying microorganisms include species of *Pseudomonas, Achromobacter, Bacillus* and *Micrococcus* such as *Paracoccus denitrificans, Thiobacillus denitrificans*, and *Micrococcus denitrificans*. Denitrifying microorganisms require the presence of metabolizable organic carbon as well as anoxic conditions. Typically denitrifying microorganisms are less sensitive to toxic chemicals than are nitrifying microorganisms, and recover from toxic shock more rapidly than nitrifying microorganisms, especially autotrophic microorganisms. Typical bioreactors include those having a free suspension of microorganisms and those having supported microorganisms which may be in a fixed or trickle bed or fluidized bed.

In these processes, Typical Mesophilic Conditions can be used. The pH of the water to be treated will depend upon its source. In general, the pH is maintained between about 4 and 8.5, for instance, between 6.0 and 8.0. Buffers, if desired, may be used to maintain the water at a given pH value during the process. In some instances, it may be possible to use metabolizable organic carbon remaining from the aerobic treatment. Generally the metabolizable organic carbon is separately added in a controlled manner in order to assure that the denitrified effluent has a low BOD. Any suitable metabolizable organic carbon can be used such as methanol, acetate anion, and the like.

Figure 4:
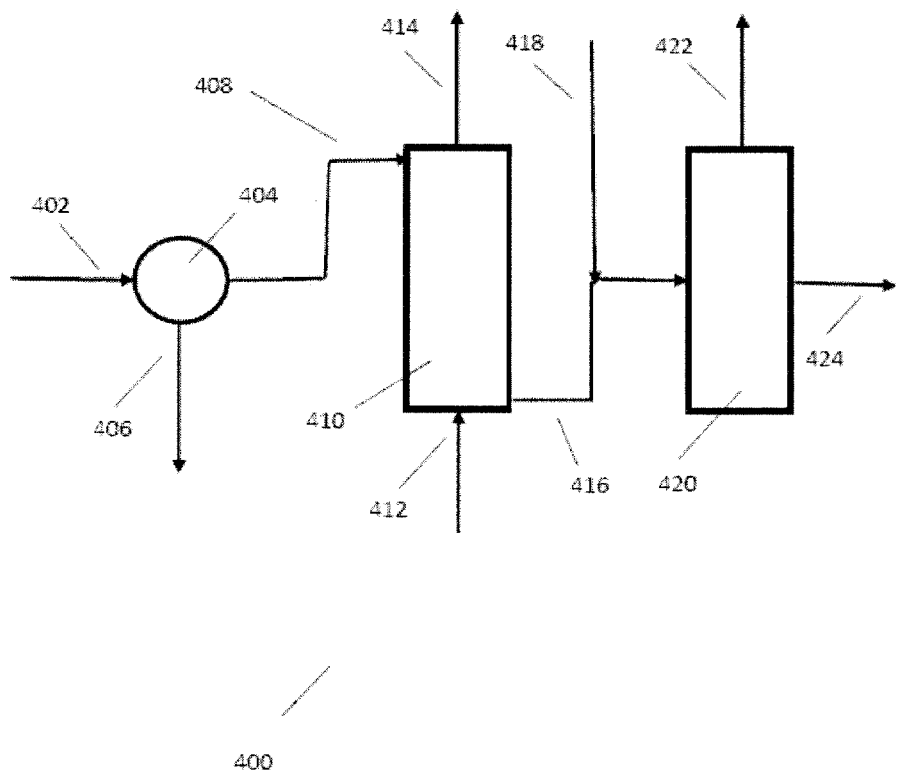
FIG. 4 is a schematic depiction of an apparatus suitable for treating municipal wastewater using the biocatalysts of this invention.
Figure 5:
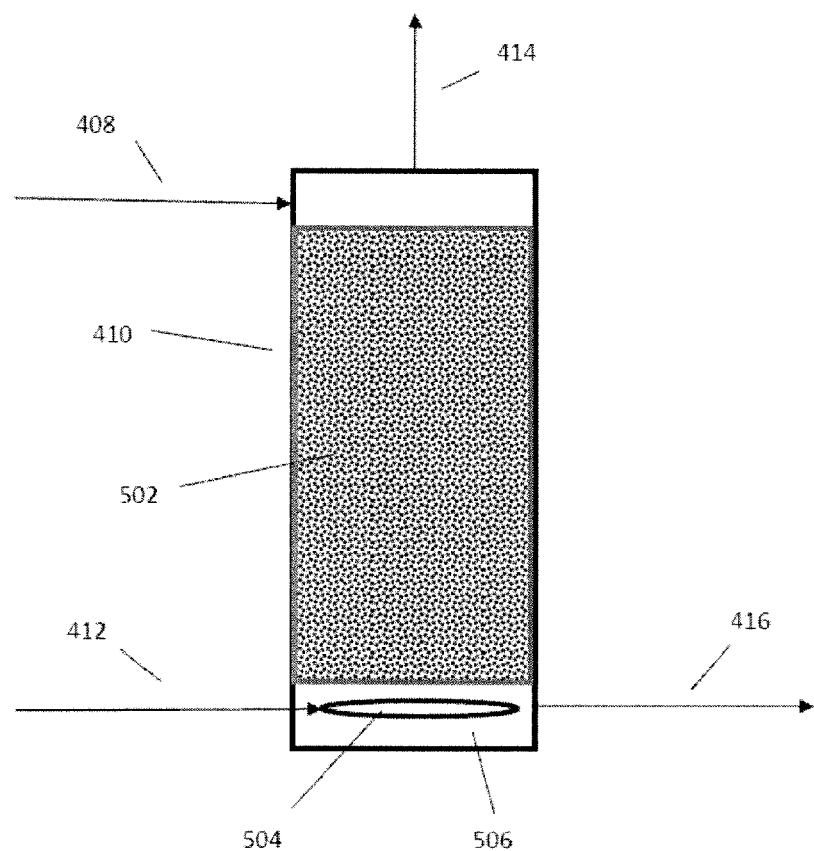
FIG. 5 is a schematic depiction of a bioreactor used for the nitrification of wastewater which also contains a zone for collecting solid debris for hydrolysis in the treatment of wastewater.

A general understanding of this process may be facilitated by reference to FIGS. 4 and 5.

Apparatus 400 is a schematic depiction of a municipal wastewater treatment facility using the processes of this invention. Municipal wastewater enters apparatus 400 via line 402. For purposes of ease of understanding, and not in limitation of the invention, the wastewater contains about 50 parts per million by mass of ammonium cation and has a BOD of about 150 milligrams per liter. The wastewater is passed to centrifuge 404 for separation of solids. It is to be understood that instead of centrifuge 404, a filter or settling ponds may be used. A thick slurry containing solids is withdrawn from centrifuge 404 via line 406. A supernatant liquid is passed from centrifuge 404 via line 408 to bioreactor 410.

Bioreactor 410 contains biocatalyst of this invention suitable for the catabolic conversion of organic carbon to carbon dioxide and ammonium cation to nitrate anion. For the purposes of this discussion, the biocatalyst is substantially that of Example 148 containing *Rhodococcus* sp. Air enters bioreactor 410 via line 412, and gaseous effluent is withdrawn via line 414. The average hydraulic residence time in bioreactor 410 is sufficient to provide an oxidized effluent having an ammonium cation concentration of less than 5 parts per million by mass and a BOD of less than 20 milligrams per liter. Bioreactor 410 is a downflow bed reactor for purposes of this illustration. Because substantially no solids are generated, no solids separation unit operation is required. However, if desired, the oxidized effluent may be passed through a filter to remove at least a portion of any solids present.

A preferred bioreactor is illustrated in FIG. 5 in which like components bear the same identification numeral as those in FIG. 4. The supernatant liquor is passed via line 408 to bioreactor 410 at the top of a bed of biocatalyst 502. Air is introduced into bioreactor 410 via line 412 and distributor 504 at a bottom portion of reactor 410. The air flows upwardly through the bed of biocatalyst. Gaseous effluent is withdrawn via line 414 at the top of bioreactor 410, and oxidized effluent is withdrawn via line 416 from the bottom of bioreactor 410 via line 416. Bioreactor 410 is depicted as having retention zone 506 below the bed of biocatalyst. This retention zone serves to retain at least a portion of the solids, at least some of which are hydrolyzed to organics that can be further oxidized to carbon dioxide during subsequent processing of the effluent. The metabolic oxidation of the organics can be effected by the microorganisms used in the biocatalyst, e.g., for the nitrification, denitrification or phosphate removal. Sometimes the indigenous microorganisms in the nitrification bioreactor and any subsequent reactor using the biocatalyst of this invention, contribute less than about 5, often between about 1 and 3 or 4, percent of the observed bioactivity.

The oxidized effluent is passed from bioreactor 410 via line 416 to anaerobic bioreactor 420. Anaerobic bioreactor 420 serves to reduce the nitrate anion to nitrogen and operates under anaerobic conditions. Advantageously, anaerobic bioreactor 420 contains biocatalyst substantially as set forth in Example 168 which contains *Paracoccus denitrificans* microorganisms. The presence of some oxygen, e.g., up to about 2 or 4 parts per million by mass, can be tolerated in the oxidized effluent being treated in anaerobic bioreactor 420. Since the organic carbon is substantially reduced in bioreactor 410, additional organic carbon such as acetate anion is added via line 418 to either the oxidized effluent in line 416 or anaerobic bioreactor 420. Anaerobic bioreactor 420 may be any suitable type of reactor. For purposes of discussion, it is a downflow, fixed bed bioreactor. The average hydraulic residence time is often less than about 1 hour.

Nitrogen and other gases exit anaerobic bioreactor 420 via line 422. A further advantage of using the biocatalyst is that relatively little of the sulfur compounds contained in the oxidized effluent are reduced to hydrogen sulfide or other sulfhydryl compounds. Anaerobic bioreactor 420 provides a denitrified effluent withdrawn via line 424. The effluent usually containing less than about 1 part per million by mass of nitrate anion.

Example 216

An apparatus containing a nitrifying bioreactor and a denitrifying bioreactor similar to that described in connection with FIG. 4 is used for this example. The example is conducted with wastewater temperatures within the range of about 20° C. to 25° C.

The effluent from a primary treatment at the municipal wastewater plant at Union City, Calif., is used as the feed to the apparatus. Fresh samples of effluent are obtained usually on a daily basis both to assure that fresh raw wastewater is being used and to observe the effect, if any, of variations in the composition of raw water being fed to a municipal wastewater facility. Changes in usage, rain runoff, and operation of the primary treatment can all have an effect. The primary effluent is maintained in a holding tank that is aerated to control odor. The COD of the primary treatment effluent varies from about 80 to 440 milligrams per liter and the BOD varies from about 50 to over 160 milligrams per liter. The ammonium cation concentration varies between about 25 and 55 milligrams per liter.

The primary effluent is fed to the aerobic nitrification bioreactor containing biocatalyst substantially as set forth in Example 148. During the first 17 days of operation, the primary effluent is fed to the bioreactor without filtration. Thereafter the effluent is filtered. The aerobic nitrification reactor is a downflow bioreactor with air being fed at the bottom which causes a suspension of the biocatalyst. A perforated plate is used to retain the bed of biocatalyst and distribute the air in the bioreactor. The bioreactor influent has a dissolved oxygen concentration of about 5 to 8 milligrams per liter. Several hydraulic retention times are used varying from about 3 hours to about 5 hours. The aerobic nitrification bioreactor has a volume at the bottom where solids are observed to settle. The effluent is then passed to a fluidized bed anoxic bioreactor containing biocatalyst substantially as set forth in Example 101. No unit operation is used to remove oxygen from the effluent from the nitrification reactor prior to its introduction into the denitrification bioreactor. The effluent from the denitrification bioreactor contains about 2 to 5 milligrams of oxygen per liter. The hydraulic residence time in the denitrification bioreactor is about 20 minutes.

After 3 days of operation, the analysis of effluent from the denitrification bioreactor commences and is continued for about 8 weeks. After 3 days, the BOD is less than 20 milligrams per liter and the ammonia is about 1 milligram per liter at a hydraulic retention time in the nitrification bioreactor of about 5 hours. After about 14 days, the BOD remained under about 10 milligrams per liter regardless of whether the hydraulic retention time in the nitrification bioreactor is 3, 4 or 5 hours. The ammonium cation concentration of the effluent also remained relatively constant at 1 or below milligram per liter except for a few days, but always below about 10 milligrams per liter. The total nitrate and nitrite in the effluent from the denitrifying bioreactor is typically below 10, and most days below about 5, milligrams per liter although occasional excursion up to about 15 milligrams per liter are observed.

Example 217

Substantially the same apparatus described in Example 216 is used for this example. The wastewater is obtained from the municipal wastewater plant at Union City, Calif., and has a COD of about 350 to 400 milligrams per liter and BOD of about 130 to over 160 milligrams per liter. The ammonium cation concentration varies between about 40 to 55 milligrams per liter.

The aerobic bioreactor contains biocatalyst substantially as described in example 134 and is operated substantially as set forth in the previous example. The average hydraulic residence time is about 3 hours in the aerobic bioreactor. The effluent from the aerobic bioreactor contains both nitrate and nitrite anion. The effluent is then passes to the anaerobic bioreactor containing biocatalyst substantially as described in example 52. The dissolved oxygen concentration in the effluent from the aerobic bioreactor is about 4 milligrams per liter. The average hydraulic residence time in the second bioreactor is about 24 minutes, and the effluent contains a total nitrogen below about 10 milligrams per liter.

ii. Phosphate Removal

As stated above, phosphorus can lead to eutrophication. Thus, in some instances, governmental regulations have required phosphate removal from wastewater streams, often to below about 1 part per million by mass (ppm-m). Despite the presence of phosphorus in surface waters, ironically phosphorus is a limited resource. Many of the commercial fertilizers that contain phosphorus derive that phosphorus from the mining of phosphorus rock, and the reserves of phosphorus rock are becoming depleted.

Numerous processes for the treatment of water to reduce phosphate concentration have been proposed such as chemical precipitation and biological treatment. One process disclosed for both removing phosphate from water and providing a phosphorus-containing fertilizer is disclosed by Britton in United States Patent Application Publication 2012/0031849. In the disclosed process struvite is produced by the addition of magnesium to phosphate containing water. The struvite is precipitated as pellets which can be used as fertilizer or for other applications. In 2007, the United States Environmental Protection Agency issued a report "Biological Nutrient Removal Processes and Costs" (EPA Report). This study considered both the chemical precipitation and biological treatment routes to remove soluble phosphates including the cost for installation and operation of selected commercial units.

By this invention biological processes are provided for the removal of soluble phosphate from water using biocatalysts of this invention. These processes for the biological reduction of soluble phosphate in water comprise:

a. contacting said water in a bioreactor with biocatalyst of this invention having substantially irreversibly retained therein phosphate accumulating microorganisms (PAOs) under phosphate accumulating conditions for a time sufficient to reduce the concentration of phosphate in said water and provide a biocatalyst containing phosphate laden microorganism wherein said phosphate accumulating conditions comprise the presence of polyhydroxyalkanoate (PHAs), especially poly-β-hydroxybutyrate, within said microorganisms and the presence of aerobic or anoxic conditions in the water:

b. subjecting said biocatalyst containing phosphate laden microorganism to anaerobic conditions in an aqueous medium sufficient to release phosphate from said microorganisms into said aqueous medium to provide a phosphate-rich aqueous medium; and c. separating said biocatalyst from the phosphate-rich aqueous medium for use and step (a).

Examples of phosphate accumulating microorganisms include, but are not limited to, Acintobacter spp., Actinobacteria, Candiidatus Accumulibacter phosphatates, α-Proteobacteria, β-Proteobacteria, and γ-Proteobacteria.

The processes of this invention treat water to remove soluble phosphate (soluble phosphate as used herein is intended to include monobasic phosphate, dibasic phosphate, tribasic phosphate, and pyrophosphate anions). The water to be treated (herein referred to as "raw water stream") may be derived from any suitable source including, but not limited to, surface and groundwater, municipal wastewater, industrial wastewater, and water generated by mining operations. Due to the robustness provided by the biocatalyst, the water to be treated may contain a number of components, including the presence of components that would, if the microorganisms were in a free suspension, adversely affect phosphate removal. The raw water feed may be subject to unit operations to remove one or more components prior to being subjected to phosphate removal or may be directly fed to the phosphate removal process.

The raw water feed often contains at least about 2, say at least about 4, milligrams of phosphate (calculated as $PO_4^{+3}$) per liter. Municipal wastewater frequently contains between about 4 and 20 milligrams of phosphate per liter; however, the processes of this invention can be used to treat raw water streams containing high concentrations of phosphate, e.g., 500 or more milligrams per liter.

The processes of this invention serve to reduce the soluble phosphate concentration in the raw water feed to provide treated water. The reduction in the concentration of soluble phosphates is often at least about 50, preferably at least about 70, percent. In the preferred aspects of this invention, the treated water contains less than about 1, and often less than about 0.1, milligram of phosphate per liter. Advantageously, the low concentrations of phosphate in the treated water can be obtained without the necessity of using a chemical precipitant. The treated water may be suitable for discharge, recycling, or further processing. Since essentially no sludge from microbial debris is generated, the treated water need not be subjected to post treatment operations such as settling ponds.

The phosphate removal is effected under oxidizing conditions. Oxidizing conditions can be provided by supplying oxygen or oxidizing component. Conveniently, the oxygen is supplied by air or enriched air. Generally, the dissolved oxygen content of the raw water feed during phosphate removal is at least about 1, preferably at least about 2, say, between about 2 and 20, milligrams per liter the oxygen may be supplied by any convenient means including by bubbling or sparging oxygen containing gas through the water or agitating or otherwise mechanically treating the water to facilitate water-gas contact. Oxidizing components include, but are not limited to, nitrate, peroxide, and percarbonate. Where such oxidizing components are used, the concentration of active oxygen is preferably in the range of between about 1 and 10, more preferably, between about 1 and 5, milligrams per liter.

As most phosphate accumulating microorganisms are mesophiles, Typical Mesophile Conditions can be used. The pH of the raw water stream being treated is preferably more basic than about 6, and is often in the range of between about 6 or 6.5 and 9.

The duration of the contact between the raw water stream and the biocatalyst during the phosphate removal step is sufficient to provide the desired reduction of soluble phosphate in the water. The duration will thus depend upon the concentration of the soluble phosphate in the raw water stream, the desired reduction of phosphate concentration, and the density of phosphate accumulating microorganisms in the bioreactor as well as the conditions employed for the phosphate removal. Due to the high concentration of phosphate accumulate microorganisms that can be provided by using the biocatalyst, relatively low batch cycle or hydraulic retention times can be realized.

The phosphate accumulating microorganisms retain the phosphorus in excess of the amount required for biological processes in the form of polyphosphate within the cell. In some embodiments, the concentrated, phosphate-containing water has a phosphate concentration at least 10 times greater than that of the raw water feed. In some instances, this concentrated water will have at least about 100, preferably at least about, 500, milligrams of phosphate per liter. Usually higher concentrations of phosphate in concentrated water result in less energy being required to obtain a solid phosphate-containing product.

A transition between the aerobic and anaerobic stages is required and can be effected in any suitable manner. For instance, the supply of oxygen or other oxidizing compound to the raw water being processed in the bioreactor may be terminated. The residual oxygen may be consumed in the accumulation of additional amounts of phosphate, and then the water being treated can be displaced with the separate aqueous medium intended to accumulate the released phosphate.

In the processes of this invention, the release of the phosphate is into a separate aqueous medium than the treated water. In preferred operations, the release of the phosphate enables a concentrated, phosphate-containing water to be obtained that is relatively free from the presence of other contaminants that may be contained in the raw water stream. Thus, the concentrated water has enhanced utility in providing phosphate suitable for industrial or agricultural use. If desired, phosphate can be recovered from the concentrated, phosphate-containing water. Any suitable process may find application to effect such recovery. Unit operations for providing even further concentrated water include chemical precipitation, evaporation, and reverse osmosis.

The phosphorus can be released by maintaining the microorganisms under anaerobic conditions. Often, the dissolved oxygen concentration in the water (or oxidizing value of an oxidizing compound is used instead of oxygen) is less than about 0.5, preferably less than about 0.2, milligrams per liter. It is to be understood that some microenvironments within the biocatalyst may have higher or lower concentrations of oxygen. Indeed, in a continuous operation is possible to sequence between the aerobic phosphate removal stage and the anaerobic phosphate release stage such that only a portion of the microorganisms retained in the biocatalyst are being used to remove and release phosphorus. The remaining of microorganisms are believed not only to be available for accommodating changes in the volume flow rate of the raw water stream and its phosphate concentration but also serve to shuttle oxygen and phosphate within the biocatalyst.

As the conditions of temperature, pressure and pH for the release of phosphate can be the same as those for the recovery of phosphate from the raw water, often there is no need to purposely induce a change. Typically it is not necessary to add nutrients, including micronutrients, to the separate aqueous medium.

For some microorganisms, the kinetic rate of release of phosphate from the microorganisms is faster than that for the accumulation of phosphate. Preferably the phosphate release stage is operated to provide a high concentration of phosphorus in the concentrated phosphate-containing product. If desired, the phosphate release stage can be operated in two or more steps, the first being to provide the maximum concentration of phosphate in the aqueous medium, and the latter steps to provide for the reduction of the phosphate contained in the microorganisms, albeit providing a concentrated phosphate-containing product that has a lower concentration of phosphate than that of the phosphate removal stage.

During accumulation of the phosphate, it is believed that the PHA and oxygen or oxidizing compounds are bioconverted to carbon dioxide and water. In general, between about 2 and 20, preferably between about 4 and 10, carbon atoms of PHA are bioconverted per phosphorus atom of soluble phosphate accumulated in the microorganism. PHA is formed by the phosphate accumulating microorganisms under anaerobic conditions in the presence of carbon-containing substrate. Volatile fatty acids of 2 to 5 carbon atoms have generally been preferred as the carbon-containing substrate. However, with the use of biocatalysts of this invention more complex carbon sources such as sugars and acetic acid can be used to generate the PHA.

The processes of this aspect of the invention, by retaining the phosphate accumulating microorganisms in the biocatalyst, provide significant flexibility as to when the PHA production occurs. For instance, the carbon-containing substrate may be provided during at least a portion of the duration of the release of phosphate, or a separate, anaerobic stage may be employed specifically for the production of PHA. In the latter case, the microenvironments within the biocatalyst and the metabolic state of the microorganisms permit the microorganisms to remain viable during the duration of the release of the phosphate stage. This latter case is beneficial where the concentrated phosphate-containing product is desired to have an essential absence of added organic compounds.

The kinetic rate for the formation of PHA depends, in part, upon the carbon-containing substrate used and the concentration of the substrate. In most instances, the biological reaction rate to PHA is more rapid than that for the accumulation of phosphate. Further, the biocatalyst can enable the retention of carbon-containing substrate beyond the duration of the PHA-generating stage, and the more occluded microorganisms in the biocatalyst may have a sufficient absence of oxygen and a sufficient presence of carbon-containing substrate to generate additional PHA.

The processes may be conducted on a batch, semi-continuous and continuous basis, and are preferably conducted on a continuous basis. The bioreactor may be in any suitable configuration including Typical Bioreactor Systems. One bioreactor can be employed and batch cycled through the phosphate removal and release stages. For most commercial operations, operation on a continuous basis is preferred. The biocatalyst may be moved from one bioreactor to another, with each of the bioreactors the adapted to perform a different function, e.g., a bioreactor for phosphate removal from the raw water; a bioreactor for phosphate release; and, optionally, a separate bioreactor for PHA generation. In this manner, countercurrent flows of biocatalyst and water can occur in each bioreactor to facilitate removal of soluble phosphate from the raw water stream and maximize the phosphate concentration in the phosphate-containing product. Another approach is to cycle each bioreactor containing biocatalyst from, e.g., a phosphate removal stage to a phosphate release stage to a PHA generation stage. Combinations of these two approaches can be used. For instance, a bioreactor may be used to remove phosphate from the raw water stream, and the phosphate removing stage is then stopped with the biocatalyst then being provided to a countercurrent flow bioreactor operating under anaerobic conditions to provide a highly concentrated phosphate-containing product. The biocatalyst is then provided to another bioreactor which first operates under PHA forming conditions and then is transitioned to conditions for phosphate removal.

Figure 6:
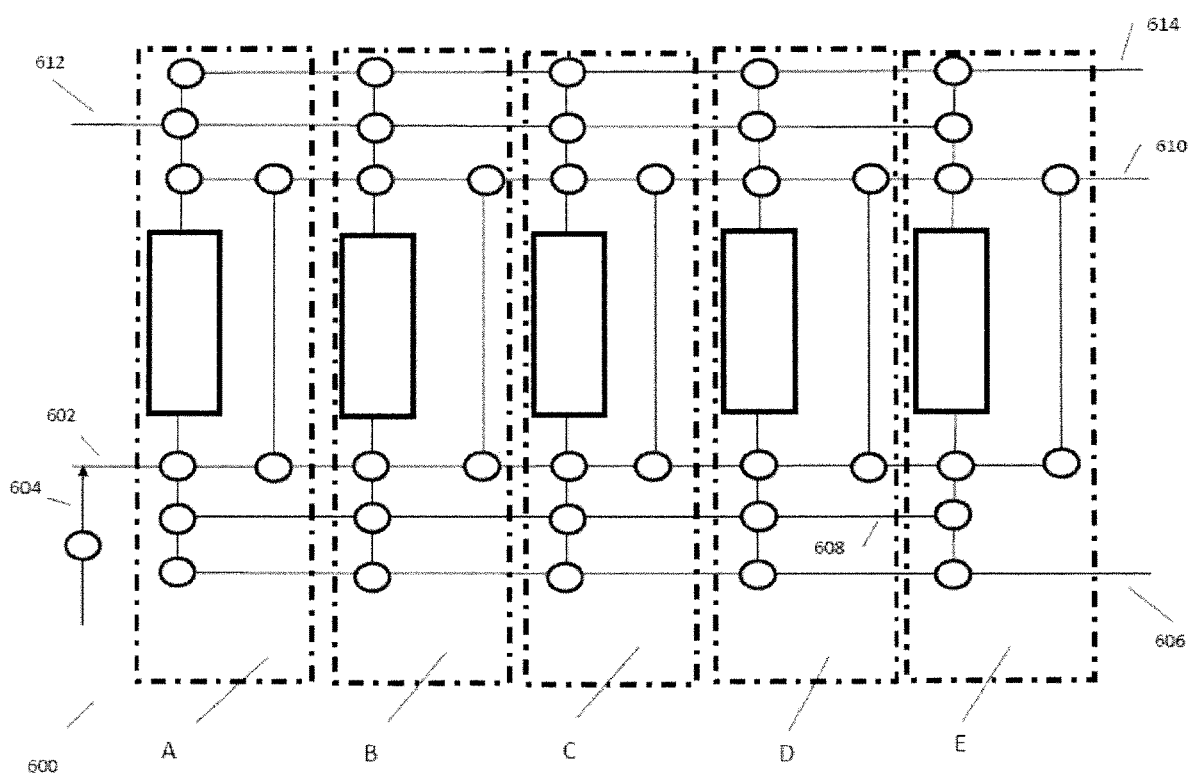
FIG. 6 is a schematic depiction of an apparatus using five fluidized bioreactor assemblies containing biocatalysts of this invention suitable for removing phosphate anion from water.
Figure 7:
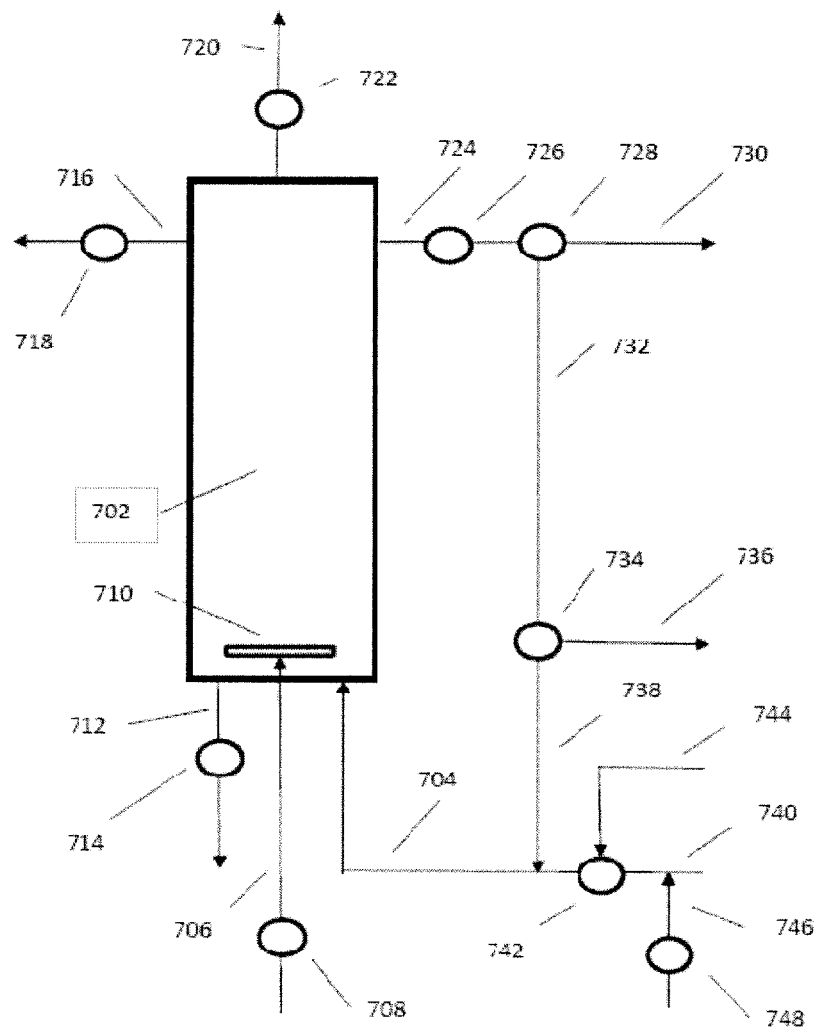
FIG. 7 is a schematic depiction of a bioreactor assembly contained in the apparatus illustrated in FIG. 6.

A general understanding of the invention and its application may be facilitated by reference to FIGS. 6, 7 and 8.

FIG. 6 is a schematic depiction of one type of apparatus generally designated as 600 suitable for practicing the processes of this invention. As depicted, the apparatus comprises 5 bioreactor assemblies A, B, C, D, and E. Each of the assemblies will be described in further detail with respect to FIG. 7.

For purposes of discussion, the bioreactors are fluidized bed reactors, although it can be readily appreciated that other types of bioreactors, such as packed bed and trickle bed, can be used. As shown, the apparatus is a number of fluid transport headers which can comprise one or more fluid conduit lines. Water flow header assembly is indicated by element 602 and provides for the transport of raw water to the bioreactor assemblies as well as water between the bioreactor assemblies and water being recycled within a bioreactor assembly. Line 604 is adapted to provide carbon source, if necessary, to header assembly 602. Air header 606 is adapted to supply air, or other oxygen containing gas, to each of the bioreactor assemblies. Drain header 608 is adapted to transport train water from one bioreactor assembly to another. Header assembly 610 is adapted to provide for fluid communication within a bioreactor assembly, from one bioreactor assembly to another bioreactor assembly, and for the removal of a concentrated phosphate-containing stream. Header assembly 612 is adapted to withdraw treated water from the apparatus. Header assembly 614 is adapted to exhaust gases from the apparatus. In FIG. 6, the circular elements generally indicate valving assemblies. The valving assemblies and operation will be discussed further in connection with FIG. 7.

FIG. 7 is a more detailed depiction of the bioreactor assemblies of FIG. 6. As shown, the bioreactor assemblies comprise bioreactor 702. Bioreactor 702 contains biocatalyst comprising *Candidatus Accumulibacter phosphatis*. Line 704 is adapted to direct aqueous streams to bioreactor 702. As will be discussed later, the aqueous stream may be a raw water stream, a stream from another bioreactor, or a recycle stream. Line 706 provides oxygen-containing gas, usually air, to the bioreactor. Valve 708 controls the flow there, and distributor 710 serves to distribute the oxygen-containing gas into bioreactor 702. Line 712 is provided at the bottom of bioreactor 702 for purposes of purging or draining bioreactor 702. Valve 714 controls the flow of water through line 712.

At the top of bioreactor 702 is provided line 720 for purposes of withdrawing gases such as the residual from the oxygen-containing gas supplied via line 706 and carbon dioxide resulting from the metabolic activity. Valve 722 is provided online 720 and is adapted to control the flow of gases through line 720. These withdrawing gases are typically discharged to the atmosphere; however, they may be subjected to treatment to insert or remove components such as methane. As shown, at an upper portion of bioreactor 702 line 716 is provided to withdraw treated water from the bioreactor. As will be discussed later, this treated water line is used to remove water from a bioreactor operating in the polishing mode, or if no bioreactor is operating in the polishing mode, then from a bioreactor operating in the primary phosphate removal mode. Valve 718 controls the flow of water through line 716. Also, line 724 is provided at an upper portion of bioreactor 702 for the removal of water for recycle or transport to another bioreactor. Both lines 716 and 724 are provided with screens, or other devices, to prevent biocatalyst contained in bioreactor 702 from passing into these lines. Line 724 is provided with valve 726 which is adapted to control the flow of water from bioreactor 702 into line 724. Line 724 is also provided with directing valve 728 which is adapted to direct the water into line 730 which carries a concentrated phosphate-containing aqueous stream for removal and/or to line 732. Line 732 contains valve 734 which is adapted to recycle water via line 738 and line 704 to bioreactor 702 or pass water into line 736 for passage to another bioreactor.

As shown, line 704 can also receive other aqueous streams. These streams can include raw water provided via line 740 and water from another bioreactor via line 744. Valve 742 is provided to control the relative volumes an amount of these streams as will be discussed later. Line 746 is adapted to provide carbon source, if necessary, to bioreactor 702. Valve 748 controls the flow of the carbon source to bioreactor 702.

For purposes of illustration only, and not in limitation of the invention, the 5 bioreactor assemblies depicted in FIG. 6 are adapted to be sequenced through various modes of operation. One skilled in the art can readily appreciate that fewer or a greater number of bioreactor assemblies can be used and the sequencing altered.

The following summarizes the five modes of operation used for purposes of this illustration:

Anaerobic PHA Generation Mode—in this mode, the bioreactor is operated under anaerobic conditions including the presence of carbon source, which may be added carbon source or that contained in the raw water to be treated;

Primary Aerobic $PO_4$ Removal Mode—in this mode, oxygen containing gas is passed through the bioreactor to effect removal of phosphate from the water;

Polishing Aerobic PO$_4$ Removal Mode—in this mode, water treated by another bioreactor that is operating in the Primary Aerobic PO$_4$ Removal Mode is further subject to contact with biocatalyst in the bioreactor for removal of additional phosphate from the water;

Purge Mode—in this mode, the bioreactor transitions from an aerobic or and anoxic environment to an anaerobic environment for release of phosphate from the biocatalyst; and Anaerobic PO$_4$ Release Mode—in this mode, the bioreactor is operated under an anaerobic environment for release of phosphate from the biocatalyst to provide a phosphate-rich effluent stream.

The following discussion describes the operation of the apparatus of FIGS. 6 and 7 using the sequencing outlined in FIG. 8. As can be seen in FIG. 8, each of the bioreactor assemblies, A, B, C, D, and E sequence through the same modes. This discussion will therefore reference the operation of a single bioreactor assembly with the understanding that the discussion will be equally applicable to each of the other bioreactor assemblies. Each of the modes of operation is of the same duration of time for purposes of this illustration.

The discussion commences with the operation of a bioreactor in the Anaerobic PHA Generation Mode, which is a reactor that has in the immediately preceding period of time been used in the Anaerobic PO$_4$ Release Mode. Thus, at the start of the cycle, the bioreactor contains an aqueous medium that, although anaerobic, is rich in phosphate. At the initiation of this cycle, valve 742 and valve 714 are closed. First, valve 714 is opened to prevent the aqueous medium in bioreactor 702 to pass through line 712 and then be directed to phosphate recovery. During draining, raw water feed to the apparatus may be terminated, or the raw water feed may be directed to a bioreactor operating in the Primary Aerobic PO$_4$ Removal Mode. Alternatively, the apparatus may be provided with surge tanks. Any suitable fluid may be used to replace the volume of bioreactor 702 that occurs from the draining. Often, air is suitable even though it is desired that the bioreactor be operated and aerobically in this mode. Alternatively, the displacement of the phosphate-rich medium in bioreactor 702 at start of this mode can be effected by passing raw water via line 704 into bioreactor 702 while withdrawing the phosphate-rich aqueous medium from the top of the bioreactor via line 724.

Once bioreactor 702 is drained, valve 714 is closed and valve 742 is positioned to permit a raw water feed stream that contains a soluble phosphate to be passed from line 740 into line 704 for introduction into bioreactor 702. The raw water feed stream refluidizes the biocatalyst. Valve 722 and valve 718 remain closed. Bioreactor 702 is operated under metabolic conditions, including anaerobic or anoxic, conditions such that the biocatalyst bioconverts the carbon source in the raw water feed to PHA. The carbon source may be contained in the raw water feed stream. If necessary, carbon source can be provided during this mode via line 746 to the desired concentration by regulation of valve 748. The raw water feed stream, after passing through the fluidized bed of biocatalyst in bioreactor 702 exits via line 724 and is passed via valve 728 to line 732. Valve 734 directs the water via line 736 to a bioreactor operating in the Primary Aerobic PO$_4$ Removal Mode. If necessary, a portion of this water may be directed by valve 734 via line 738 back to bioreactor 702 in order to maintain a desired degree of fluidization of the biocatalyst.

Near the completion of the Anaerobic PHA Generation Mode, bioreactor 702 the transition to the Polishing Aerobic PO$_4$ Removal Mode is commenced. This transition comprises initiating the flow of oxygen-containing gas into bioreactor 702 via line 706 by opening valve 708. At this time, valve 722 is opened to permit gases to exit bioreactor 702 via line 720. The flow of the water from bioreactor 702 remains unchanged during this transition and is passed to a bioreactor operating in the Primary Aerobic PO$_4$ Removal Mode. This transitioning allows the bioreactor to serve as the bioreactor operating in the Polishing Aerobic PO$_4$ Removal Mode during the next period.

At the conclusion of Period 1 valve 742 terminates the flow of raw feed water and commences flow of effluent from the bioreactor operating in the Primary Aerobic PO$_4$ Removal Mode from line 744. Also, valve 726 is closed and valve 718 is open to permit phosphate-reduced water to pass from the apparatus via line 716. However, if a recycle stream is desired to provide sufficient flow to fluidize the biocatalyst in bioreactor 702, valve 726, valve 728 and valve 734 can be set to provide the sought flow rate of water back to bioreactor 702. Since the prior transitioning placed bioreactor 702 in an aerobic environment, the microorganisms have an enhanced PHA content and reduced phosphorus content and thus can effectively remove soluble phosphate in the water being treated to desirably low concentrations. In addition, the use of a bioreactor in the Polishing Aerobic PO$_4$ Removal Mode enables fluctuations in the soluble phosphate concentration in, as well as fluctuations in the flow rate of, the raw water feed to be accommodated while still providing the sought flow phosphate concentration in the treated water.

In general, no transitioning is required to cycle a bioreactor from operation in the Polishing Aerobic PO$_4$ Removal Mode to the Primary Aerobic PO$_4$ Removal Mode. Bioreactor 702, at the conclusion of Period 2, begins operation in the Primary Aerobic PO$_4$ Removal Mode by switching the source of the water and line 744 from another bioreactor operating in the Primary Aerobic PO$_4$ Removal Mode to the effluent from a bioreactor operating in the Anaerobic PHA Generation Mode. Valve 718 is closed and valve 726 is opened permitting the aqueous medium to the directed via line 724 to valve 728 and to line 732. Valve 734 directs the effluent via line 736 to a bioreactor operating in the Polishing Aerobic PO$_4$ Removal Mode. A portion of the effluent may be directed by valve 734 to line 738 for recycle to bioreactor 702 in order to provide the desired fluidization of the biocatalyst.

Either before the end of Period 3 in which bioreactor 702 is operating in the Primary Aerobic PO$_4$ Removal Mode or at the beginning of Period 4 in which bioreactor 702 will be operating in the Purge Mode, valve 708 is closed to cease the flow of oxygen-containing gas into bioreactor 702. Sufficient residual oxygen remains in the aqueous medium in bioreactor 702 and in the biocatalyst to permit additional dissolved phosphate uptake. The effluent from bioreactor 702 can continue to be directed to a bioreactor operating in the Polishing Aerobic PO$_4$ Removal Mode or a bioreactor operating in the Primary Aerobic PO$_4$ Removal Mode (line 736 would thus be in fluid communication with line 744 of another bioreactor which is operating in the Primary Aerobic PO$_4$ Removal Mode). Usually in the Purge Mode, the aqueous medium in bioreactor 702 is continually recycled through positioning of valves 726, 728, and 734. If desired, all or a portion of the aqueous medium contained in bioreactor 702, which medium contains dissolved oxygen, can be drained via line 712. The drained aqueous medium can be passed to another bioreactor operating in either the Primary Aerobic PO$_4$ Removal Mode or the Polishing Aerobic PO$_4$ Removal Mode. In the Purge Mode the process to release phosphorus retained by the microorganisms begins. The Purge Mode also facilitates dissipating oxygen concentration gradients within the biocatalyst.

In Period 5, bioreactor 702 is operated in the Anaerobic $PO_4$ Release Mode. In this mode, the phosphate-laden water in bioreactor 702 is recycled by means of lines 724, 732, 738, and 704, with a portion of the water being directed by valve 728 to line 730. The combination of the use of a Purge Mode with the Anaerobic $PO_4$ Release Mode tends to provide the highest feasible concentration of phosphate in the water stream withdrawn via line 730. In an alternative embodiment, the phosphate-laden water in bioreactor 702 may be drained through line 712. The phosphate-laden water may be disposed or subjected to further chemical or processed treatment to recover phosphate. For instance, struvite may be formed and phase separated with return of the water to the apparatus. Alternatively, the phosphate-laden water may be subject to evaporation, distillation, or reverse osmosis to provide a more concentrated phosphate-containing stream which may find industrial or agricultural use.

Although the illustration has depicted the Purge Mode and Anaerobic $PO_4$ Release Mode to occur in separate periods, the modes may be combined in a single period.

iii. Mitigation of Biofouling from Aquatic Microorganisms

Water obtained from sources containing aquatic organisms, especially macroorganisms such as barnacles (such as acorn barnacles and goose barnacles); marine mussels; freshwater mussels; zebra mussels; bryozoans; tube worms; polychaetes, seasquirts, sponges; and sea anemones, is used for a number of purposes. For example, the water may be sought to be used as potable water, a source of water for desalination, cooling water such as for power plants and manufacturing facilities, for sanitary facilities, and ballast for ships. Water sources contain the macroorganisms can cause biofouling of surfaces such as pipes, tanks and process equipment such as pumps, valves, heat exchangers, filtration devices, reactors and the like. Periodic maintenance is required to remove the deposits or replace fouled equipment. Removing the deposits from these macroorganisms can be problematic due to the strength of adherence of these organisms to the surface and the hardness of the shell bodies.

In accordance with this aspect of the invention, the water that contains or may contact aquatic macroorganisms is first contacted with biocatalysts of this invention containing microorganisms that are capable of catabolic conversion of dissolved, metabolizable organic carbon (organocarbon) in the water. The microorganism selected should be tolerant of the other components of the raw water including, but not limited to, salinity, other anions and cations, any organics or pollutants present, and pH. Examples of microorganisms capable of converting organocarbon to carbon dioxide include, but are not limited to, *Acinetobacter Johnsonii, Alcanivorax dieselolie, Azoarcus* sp, *Bacillus globiformis, Bacillus mojavensis, Bacillus subtilis, Escherichia coli, Eubacterium biforme, Lactosphaera pasteurii. Microthirx parvicella, Moraxella cuniculi, Nocardia asteroids, Pseudomonas pseudoalcaligenes, Rhococccus rhodnii, Rhodcoccus coprophilus, Rhodoferax fermentans, Rhodococcus jostii, Saccharophagus degradans, Skermania piniformis, Sphingomonas capsulate, Variovorax paradoxus,* and *Zoogloea* sp The contact is for a time sufficient to reduce the concentration of metabolizable organocarbon to a level where survival of macroorganisms is inhibited. A water feed may be continuously contacted with biocatalyst; however, intermittent or periodic treatment of the water may be sufficient to disrupt macroorganism growth downstream of the biocatalyst.

Accordingly, biofouling by aquatic macroorganisms can be accomplished without the addition of chemicals. Moreover, the biocatalysts do not themselves generate food sources for the macroorganisms, do not increase the mass of solids to be removed by any downstream filtration. In preferred aspects of the invention, the concentration of organocarbon downstream from the contact with the biocatalyst is insufficient to maintain the viability of suspended microorganisms.

The water is often, but not necessarily always, obtained from surface sources and maybe salt, brackish or fresh water. The water contains food and nutrients for supporting the aquatic macroorganisms, and usually contains microorganisms.

The conditions for the contacting of the water and biocatalyst may vary over a wide range and is usually under Typical Mesophile Conditions. Usually, the temperature of the contacting is substantially the ambient temperature of the water. In some instances, the dissolved oxygen in the water is sufficient for the metabolic bioconversion of the organocarbon to carbon dioxide; however, aeration of the water may be desired in some instances. Generally, the dissolved oxygen content in the water to be contacted with the biocatalysts is in the range of about 1 to 50 or more, say, 1 to 10, parts per million by mass. Typically no nutrients need be added to the water.

The bioreactor may be in any suitable configuration including Typical Bioreactor Systems. With the high cell densities and bioactivities achievable using with the biocatalysts of this invention, the average hydraulic residence time of the water in the bioreactors is typically less than about 24, more frequently less than about 6 or 10, hours, and in some instances may be in the range of about 0.5 to 4, hours.

Since the biocatalyst provides environments in which the microorganisms can survive for extended periods of time without the addition of additional food sources, the biocatalyst can be cycled between environments containing organocarbon ("metabolizing cycle") and environments containing essentially no organocarbon ("cleaning cycle"). This cycling often retards any growth of organisms on the surface of the biocatalyst. In general, the duration of the cleaning cycle, if used, is at least about 2, say, between about 6 and 48, hours.

Figure 9:
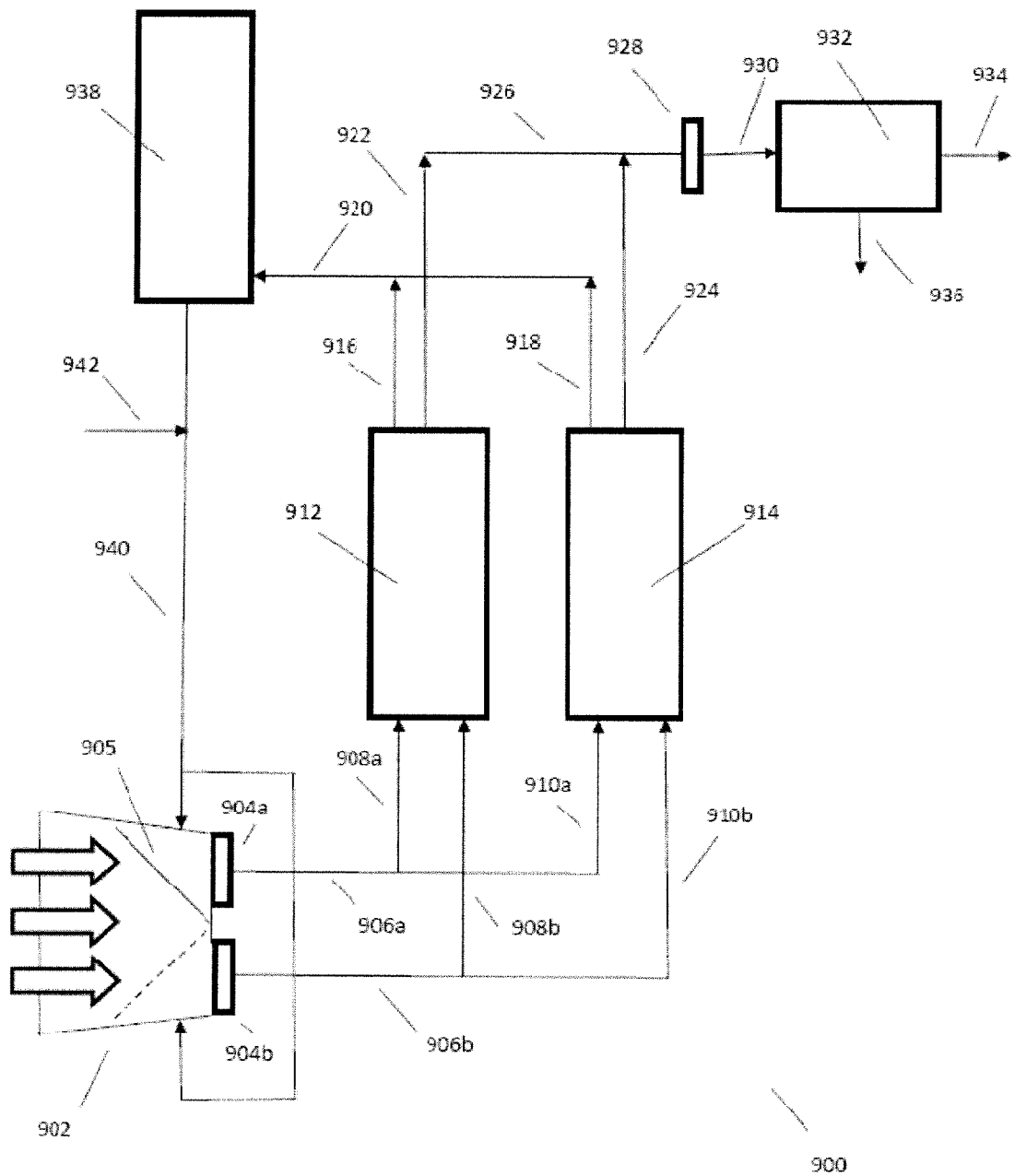
FIG. 9 is a schematic depiction of an apparatus containing biocatalysts of this invention which is suitable for treating water to minimize macroorganism growth and which contains an optional, self-cleaning water supply system.

With reference to FIG. 9, apparatus 900 is an assembly for the desalination of seawater using reverse osmosis membranes. Seawater is passed to plenum 902. The arrows indicate the flow of the seawater into plenum 902. Plenum 902 as a plurality of screens, two of which are illustrated, screen 904a and screen 904b. Movable flap 905 is provided in plenum 902 and is adapted to stop flow of water to screen 904a and then move as indicated by the dotted line to stop flow of water to screen 904b. It is to be understood that movable flap 905 may be positioned such that water can flow to both screens 904a and 906b.

Each screen has a dedicated header which for screen 904a is header 906a, and for screen 904b is header 906b. Each header has lines going to each bioreactor. For purposes of this illustration, two bioreactors are shown, bioreactor 912 and bioreactor 914. Line 908a provides fluid communication between header 906a and bioreactor 912, and line 908b provides fluid communication between header 906b and bioreactor 912. Line 910a provides fluid communication between header 906*a* and bioreactor 914, and line 910*b* provides fluid communication between header 906*b* and bioreactor 914.

Each bioreactor 912 and 914 are depicted as fluid bed bioreactors containing biocatalyst, which for purposes of discussion is the biocatalyst of example 113. Bioreactor 912 is shown as having effluent lines 916 and 912, and bioreactor 914 is shown as having effluent lines 918 and 924. Effluent lines 916 and 918 are in fluid communication with recycle header 920. Effluent lines 922 and 924 are in fluid communication with treated water header 926. Treated water header 926 directs treated water to ultrafiltration membrane unit 928. The filtrate from ultrafiltration membrane unit 928 is passed via line 930 to reverse osmosis unit 932. Desalinated water exits via line 934, and a rejected stream exits via line 936 from reverse osmosis unit 932.

Returning to recycle header 920, water is passed to surge tank 938. Water from surge tank 938 can be directed via line 942 plenum 902. The water from line 942 enters plenum 902 in the region occluded by movable flap 905 and upstream of the occluded screen.

There are several modes of operation of the apparatus, all within the broad aspects of this invention. In one mode, bioreactors 912 and 914 operate independently, and in another mode, bioreactors 912 and 914 operate in water flow sequence.

By way of example, in a first mode of operation raw water enters plenum 902 and is directed through screen 904*b* to header 906*b*. Line 908*b* is valved off, and the water in header 906*b* passes through line 910*b* to bioreactor 914. In bioreactor 914, organocarbon is converted to carbon dioxide to provide a treated water stream containing essentially no organocarbon. This treated water stream exits via line 924 and passes to treated water header 926 where it ultimately passes through the reverse osmosis unit to provide a desalinated water. At this point in time, line 918 is valved off.

Surge tank 938, which had previously been filled with treated water containing essentially no organocarbon, supplies water via line 940 into the occluded region of plenum 902 defined by movable flap 905 and screen 904*a*. The water is then passed through screen 904*a* into header 906*a*. Line 910*a* is valved off so that water does not enter bioreactor 914, but line 908*a* is valved open such that the treated water passes through the bioreactor 912. The water then exits bioreactor 912 via line 916 to be returned by recycle header 920 to surge tank 938. At this point in time, line 922 is valved off. As can be seen, the cycling of treated water through screen 904*a*, header and line 906*a* and 908*a* and bioreactor 912 serve to provide a cleaning cycle. The use of movable flap 905 enables the treated water to contact the flap to similarly attenuate the growth of macroorganisms on the flap.

Upon the completion of the cleaning cycle for screen 904*a*, header 906*a* and bioreactor 912, movable flap 905 is moved to permit flow of raw water through screen 904*a* and occlude the flow of raw water to screen 904*b*. The same valving positions are maintained for headers 906*a* and 906*b* which results in bioreactor 912 treating the raw water. Effluent line 916 is valved off and effluent line 922 is valved open to pass the treated water to treated water header 926. Bioreactor 914 is subjected to a cleaning cycle as is screen 904*b*, header 906*b* and line 910*b*. Effluent line 924 from bioreactor 914 is valved off, and effluent line 918 is valved open and passes the water to recycle header 920. Water from surge tank 938 is passed via line 940 to the occluded region defined by movable flap 905 and screen 904*b* in the plenum. The side of the plenum that had been exposed to raw water during the prior cycle is now exposed to the water having an essential absence of organocarbon. Thus, the apparatus facilitates maintaining both sides of movable flap 905 relatively free of macroorganisms.

In the next cycle, line 908*a* is valved off, line 908*b* is valved open and bioreactor 912 is subjected to a cleaning cycle. At the same time, line 910*a* is valved open, line 910*b* is valved off and bioreactor 914 serves to treat raw water to remove organocarbon. In this cycle, effluent line 918 is valved off and effluent line 924 is valved open and passes treated water to treated water header 926. Also, effluent line 922 from bioreactor 912 is valved off, and the water is passed via line 916 to recycle header 920.

In the last of the four cycles, movable flap 905 is moved to occlude flow of raw water to screen 904*a* and permit flow of raw water to screen 904*b*. Thus, bioreactor 914 treats raw water, and effluent line 918 is valved closed and effluent line 924 is valved open to direct the treated water to treated water header 926. Bioreactor 912 is subjected to a cleaning cycle with effluent line 916 valved opened and effluent line 922 valved closed. Line 940 directs the water from surge tank 938 to the occluded region defined by movable flap 905 and screen 904*a*.

The apparatus depicted in FIG. 9 can also be used in a sequential bed mode. In a first cycle movable flap 905 provides an occluded region upstream from screen 904*a* in plenum 902. Raw water entering plenum 902 passes through screen 904*b* and into header 906*b*. Line 908*b* is valved closed, and the water passes through line 910*b* into bioreactor 914 for treatment to remove organocarbon. The treated water is passed via line 918 to recycle header line 920. Line 924 is valved closed. Thus surge tank 938 receives a treated water which is then passed via line 940 the occluded region in advance of screen 904*a*. Since the treated water has substantially no organocarbon, the water is useful for a cleaning cycle. This water enters header 906*a* and is passed to bioreactor 912 via line 908*a* which is valved open. Line 910*a* is valved closed. Any residual or additional organocarbon is us subjected to biocatalyst in bioreactor 912 for additional bioconversion to carbon dioxide. The water from bioreactor 912 is passed via line 918 to treated water header 926. Effluent line 916 is valved closed.

In a manner consistent with the description of the first mode of operation of the apparatus, the movable flap positioning and valving to each of the bioreactors can be cycled such that all lines and reactors are passed through a cleaning cycle.

iv. Aerobic Catabolysis of Ammonium Ion to Nitrogen

As discussed above biological processes for removal of ammonium cation from aqueous streams oxidize ammonium cation typically conducted in an aerobic environment. The oxidation effluent contains nitrate anions and possibly nitrite anions, especially where the oxidation is not complete. Often over 4 kilograms of oxygen are consumed per kilogram of ammonium nitrogen removed and the nitrification and denitrification processes and increase power consumption for a typical facility by 30 percent or more.

The resulting nitrate and nitrite ions are also contaminants and are preferably removed from the water prior to discharge to the environment. Bioconversion processes for denitrification are also well known. Typically the reduction of these oxyanions to nitrogen requires an anoxic or anaerobic environment and electron donor. Hence, some facilities add a donor such as methanol or even raw sewage. The need for fundamentally different conditions for ammonium oxidation and nitrate reduction contributes to the capital and operating expense of adopting a system to bioconvert ammonium to nitrogen. The anaerobic conditions for the nitrate reduction can also lead to the production of hydrogen sulfide and other sulfhydryl compounds.

Also discussed above is the anammox process.

By this aspect of the invention, the biocatalysts of this invention enable ammonium cation to be bioconverted in an aerobic environment to nitrogen using microorganisms contained in activated sludge (herein referred to as an "N/D microorganism". Since the biocatalyst of this invention is used, no solids are generated by the microorganisms in the biocatalyst. In the broad aspects, the contacting between water containing ammonium cation and the biocatalyst is under metabolic conditions for a time sufficient to provide a treated water having a concentration of ammonium less than about 50, preferably less than about 90, percent of that in wherein the nitrate concentration of the feed water and a concentration of nitrate ion less than about 1 milligram per liter. Further, this reduction of nitrate and nitrite anions in the treated water can occur even in the presence significant amounts of oxygen, e.g., greater than 5 or 8 milligrams of oxygen per liter, in the water. In preferred embodiments of this aspect of the invention, the treated water contains sufficient water that it need not be aerated for discharge to the environment, e.g., contains at least about 0.5, preferably at least about 1, milligram of oxygen per liter. Moreover, no hydrogen sulfide or other sulfhydryl compounds are generated by the process.

The water may be from any source including municipal wastewater, ground water and surface water. The ammonium cation content of the water to be treated can also vary over a wide range and is often between about 5 or 10 and 250, more frequently between about 25 and 200, milligrams per liter. The water to be treated may contain other components including, but not limited to, sulfur compounds, phosphorus compounds, inorganic salts and solubilized metals. Often, the oxygen concentration in the water to be treated is in the range of from about 0.5 to 10 or more milligrams per liter.

The biocatalyst of this invention used in these processes contain N/D microorganisms Suitable N/D microorganisms may or may not exhibit both nitrification and denitrification metabolic activities when in a free suspension in an aqueous medium. While not wishing to be limited to theory, it is believed that a phenotypic alteration occurs in some instances that contributes to the performance of N/D microorganisms. The N/D microorganisms can be obtained from activated sludge. Preferably, the activated sludge is acclimated under aerobic conditions under Typical Mesophile Conditions and fed with bicarbonate anion. In some instances the pH is maintained at between about 6 and 8.

The ammonium biodegradation processes may be conducted in any suitable manner. The processes may be on a continuous, semi-continuous or batch mode of operation and use Typical Bioreactor Systems.

Any suitable metabolic conditions can be used including Typical Mesophile Conditions. In general, the pH is maintained between about 4 and 8.5, for instance, between 6.0 and 8.0. Buffers, if desired, may be used to maintain the water at a given pH value during the process. Carbon source nutrient may be required and may be any convenient carbon source such as a low molecular weight hydrocarbon or oxygenated hydrocarbon such as ethanol, acetate, and sugars.

The duration of the contact of the water and biocatalyst is for a time sufficient to obtain the sought reduction in ammonium. The duration can vary over a wide range depending upon the type of reactor, the biocatalyst and the concentration of the microorganism population in the bioreactor. In many instances, the duration of the contact may be less than 12, preferably less than 8, hours to achieve a reduction in ammonium concentration to less than about 1 milligram per liter, and sometimes, the contact is less than one hour. A significant advantage of the processes of this invention is that not only is ammonium converted to nitrogen, the treated water contains little, if any, nitrate or nitrite anion.

Example 218

A continuously stirred, aerated tank bioreactor is filled to about 70 percent of its height with a biocatalyst substantially as described in example 92 but using microorganisms derived from activated sludge acclimatized as set forth above and at a wet cell density of about 350 to 400 grams per liter. The biocatalyst is in the form of spheres having diameters of about 4 millimeters. The effluent from a primary treatment at the municipal wastewater plant at Union City, Calif., is used as the feed to the bioreactor. A series of batch runs are conducted in the bioreactor, each using the effluent with different ammonium cation concentrations: 100, 200 and 1000 milligrams of ammonium cation per liter. The ammonium cation concentrations are adjusted by the addition of ammonium hydroxide. The pH is adjusted to about 7 at the beginning of each run. Each run is conducted until the ammonium cation concentration is below about 0.1 milligram per liter. At the conclusion of each run, the wastewater is analyzed for nitrite and nitrate anion. The total nitrogen in the wastewater is below about 1 milligram per liter.

v. Nitrate and Perchlorate Removal from Water

The biocatalysts of this invention can be used to remove nitrate and remove perchlorate anion, and both when present together, from water. Nitrates are a contaminant in water, and the United States Environmental Protection Agency has set a limit of 10 milligrams of nitrate (based on the mass of nitrogen) in potable water. Perchlorate anion contamination of a number of sources of ground water and surface water has occurred. The concentration of perchlorate anion in these contaminated waters can vary widely. One health concern that arises due to the presence of perchlorate is its interference with the thyroid gland's ability to produce hormones which in turn can cause metabolism, growth and development problems. Due to concerns about the adverse effects of perchlorate, reduction of perchlorate levels to concentrations in the very low micrograms per liter are sought to be achieved. Often, water that is contaminated with perchlorate anion contains nitrate anion. The presence of nitrate in water contaminated with perchlorate poses challenges to a metabolic process in that not only is nitrate preferentially reduced, but also the concentration of perchlorate has to be reduced to very low levels.

In the broad aspects, the processes for reducing the concentration of nitrate anion or perchlorate anion or both when present in water comprises contacting the water with a biocatalyst of this invention containing a strain of microorganism capable of reducing said anions under metabolic conditions and for a time sufficient to bioconvert such anion. Nitrate and perchlorate-reducing microorganisms, especially bacteria, are readily obtainable from the environment and some prior workers have described self-inoculation systems for the biodegradation of these anions. See, for instance, U.S. Published Patent Application No. 2010/0089825. Representative of species of bacteria that are available in nature, especially creek and waste water, include *Vibrio dechloraticans, Cuznesove* B-1168, *Wolinella succi-* nogenes, *Acinetobacter thermotoleranticus, Ideonella dechloratas, Ralstonia eutrophia*, and GR-1, a strain identified to belong to the β subgroup of *Proteobacteria*. See, for instance, Coates, et al, Nature Rev. Microbiol., 2, pages 569-80 (2004), and Applied Environmental Microbiol., 65, pages 5234-41 (1999); and Wu, et al, Bioremediation Journal, 5, pages 119-30 (2001) for discussions of microorganisms capable of perchlorate respiration. It is understood that microorganisms used may be wild strains or may be genetically-modified recombinant microorganisms.

The concentration of nitrate in the water can vary widely depending upon source, and is often in the range of about 0.5, say, 1, to 100 or more milligrams per liter. In mining operations and aquaculture, wastewater can often contain 500 or more milligrams of nitrate per liter, and reduction of such high concentrations of nitrate anion to suitable levels for discharge has heretofore been problematic. The concentration of perchlorate in the water can vary widely depending upon source. In some reported instances, perchlorate concentrations greater than 10 milligrams per liter have been observed. However, in view of the concerns raised by perchlorate contamination, it may be desired to treat water that contains very low concentrations of perchlorate, e.g., as low as about 10 micrograms per liter. The water to be treated may contain other components including, but not limited to, sulfur compounds, phosphorus compounds, inorganic salts and solubilized metals. Often, the oxygen concentration in the water to be treated is in the range of from about 0.5 to 10 or more milligrams per liter.

The biocatalyst may contain any suitable microorganism. The biodegradation processes may be conducted in any suitable manner. The processes may be on a continuous, semi-continuous or batch mode of operation using suitable bioreactors including Typical Bioreactor Systems.

Suitable metabolic conditions are maintained such as Typical Mesophilic Conditions. The pH of the water to be treated will depend upon its source. In general, the pH is maintained between about 4 and 8.5, for instance, between 4 and 8.0. Lower pH tends to enhance the degradation of perchlorate anion.

If needed, electron donors can be added to the water to be treated. Electron donors include, but are not limited to, hydrogen, carbohydrates, hydrocarbons, alkanols, aldehydes, carboxylic acids, ketones, aldehydes, glycerides and the like. See, for instance, paragraph 0055 of U.S. Published Patent Application No. 2006/0263869. If electron donors are required, they may be added in any suitable manner. The addition of electron donors is typically based upon achieving the sought reduction in perchlorate rather than total electron acceptor in the water to be treated. Accordingly, where electron donor has to be provided, the processes of this invention require less electron donor than those where oxygen is preferentially consumed prior to any significant biodegradation of perchlorate anion.

The duration of the contact of the water and polymeric matrices is for a time sufficient to obtain the sought reduction in nitrate and perchlorate anion. The duration can vary over a wide range. As stated above, even though the concentration of perchlorate anion may be very low, e.g., less than 100 micrograms per liter, and oxygen is present, the duration of the contact may be relatively brief, even to achieve a treated water containing less than 5 micrograms of perchlorate per liter. In many instances, the duration of the contact may be less than several hours to achieve a reduction in perchlorate anion concentration of less than about 5 micrograms per liter, and sometimes, the contact is less than one hour, and often less than about 30, even less than about 5, minutes.

The treated water can contain oxygen as the use of the biocatalyst does not necessitate that oxygen be consumed prior to the biodegradation of perchlorate anion. In most instances, the oxygen concentration of the treated water is at least about 0.1, preferably at least about 0.5, and most preferably at least about 10 or even 50, milligrams per liter. Whether or not the dissolved oxygen concentration in the treated water is sufficiently high to be discharged without aeration will in part depend upon the oxygen concentration in the water to be treated. Filtration may be desired to remove any solids from, e.g., exogenous microorganisms that may be introduced with the water to be treated.

Example 219

An aqueous solution is prepared that contains perchlorate anion in an amount of 500 micrograms and nitrate anion (calculated as nitrogen) in an amount of 10 milligrams per liter of distilled water. Oxygen is removed to below 0.5 milligram per liter by sparging the aqueous solution with nitrogen. The volume of the aqueous solution is reduced by about 20 volume percent and contains 410 micrograms of perchlorate anion and 15 milligrams of nitrate anion per liter of aqueous solution. Sodium acetate is then added in an amount of 0.6 parts by mass of sodium acetate per part by mass of total perchlorate and nitrate anion in the aqueous solution. The pH of the aqueous solution is adjusted to about 7.

The aqueous solution is then added to a glass flask containing biocatalysts of Example 31 in an amount sufficient to immerse the biocatalyst. The aqueous solution and biocatalyst is maintained at room temperature, about 25° C. After 24 hours, the perchlorate concentration of is about 80 micrograms per liter of solution and the nitrate concentration is about 790 micrograms per liter of solution.

Example 220

An aqueous solution containing 128 milligrams of nitrate anion, 12 milligrams of nitrite anion, and about 9 milligrams of molecular oxygen per liter of water is continuously fed to an up-flow bioreactor at a rate that provides a hydraulic residence time of 25 minutes. The up-flow reactor contains the biocatalyst as substantially set forth in Example 52. The treated water from the bioreactor contains less than about 1.3 milligrams of nitrate anion and less than 0.01 milligrams of nitrite anion per liter of water.

Example 221

An aqueous solution containing about 12 to 15 milligrams of nitrate anion and about 0.4 milligrams of perchlorate anion and about 4 milligrams of molecular oxygen per liter of water is continuously fed to an up-flow bioreactor at a rate that provides a hydraulic residence time of 25 minutes. The up-flow bioreactor contains about 70 percent of it volume with biocatalyst substantially as described in Example 52. The biocatalyst contains *Paracoccus denitrificans*. The pH of the water being passed to the bioreactor is adjusted to about 7, and sodium acetate is added to the water as carbon source. The nitrate concentration of the effluent from the bioreactor is less than about 1 milligram per liter and perchlorate anion less than about 4 micrograms per liter.

Example 222

An aqueous solution containing between about 600 and 800 milligrams of nitrate anion per liter is continuously fed to two up-flow bioreactors in series. Each up-flow reactor is the same size, and each contains the biocatalyst as substantially set forth in Example 52. The hydraulic residence time is varied between 25 minutes and 30 minutes based upon the volume of both bioreactors. The treated water from the second bioreactor contains less than 10 parts per million nitrate anion and less than 1 part per million nitrite anion.

vi. Metals Removal

Soluble metal and semi-metal compounds can be found as contaminants in various water sources. These contaminants may be naturally occurring or can be the result of human activities such as manufacturing, mining, metal-refining, waste disposal, and the like. Some of these compounds pose health hazards and can adversely affect the environment.

The biocatalysts of this invention are beneficially useful for treating water containing at least one soluble compound of metal or semi-metal since the interior of the biocatalyst provides microenvironments that favor redox conditions for effecting the reduction of the metal or semi-metal to form a solid. These processes comprise:

(a) continuously introducing said water into a reaction zone containing biocatalyst of this invention;
(b) contacting the water with said biocatalyst which contains microorganism capable of reducing said soluble compound for a time sufficient to reduce the concentration of said at least one soluble compound in the water;
(c) maintaining said biocatalyst under metabolic conditions sufficient to metabolically reduce the oxidation state of the metal or semi-metal to form elemental metal or semi-metal or precipitated compound thereof; and
(d) withdrawing water having a reduced concentration of said at least one soluble compound from the bioreaction zone.

Frequently, the metal or semi-metal of the soluble compound comprises at least one of sulfur, phosphorus, selenium, tungsten, molybdenum, bismuth, strontium, cadmium, chromium, titanium, nickel, iron, zinc, copper, arsenic, vanadium, uranium, radium, manganese, germanium, indium, antimony mercury, and rare earth metals. The soluble compound will depend upon the particular metal or semi-metal, and may be an hydroxide, carbonate, nitrate, carboxylate (e.g., formate, acetate, or propionate); or an oxyanion of the metal or semi-metal that is soluble in water.

The metabolic conditions include the presence of a carbon source which is metabolized by the microorganisms in the biocatalyst. The metabolism of carbon source is believed to provide a gradient within the interior of the biocatalyst to enhance the activity of a portion of the microorganisms for the metabolic reduction of metals and semi-metals. Hence, the metabolic reduction can occur even where the water being treated contains oxygen. The metabolic reduction may provide an elemental material or a precipitated compound. The precipitated compound has the metal or semi-metal in a reduced oxidation state, and the precipitated compound may be one or more of oxides, carbonates, sulfides and hydroxides. The specific nature of the precipitated compound will depend upon the metal or semi-metal of which it is composed to provide the insolubility properties.

In some instances, the metabolic reduction of the metal or semi-metal may lag the accumulation of the soluble compound by the porous matrices and the microorganisms. In such situations, the bioreaction zone may be sized to permit a steady-state operation, or porous matrices may be cycled between a bioreaction zone to which the water to be treated is passed and bioreaction zone that is maintained under metabolic conditions where additional metabolic reduction occurs.

The metabolic processes may be conducted in any suitable manner including Typical Mesophilic Conditions and using Typical Bioreactor Systems. Carbon source nutrient may be required and may be any convenient carbon source such as a low molecular weight hydrocarbon or oxygenated hydrocarbon such as ethanol, acetate, and sugars.

The interior of the biocatalyst provides a plethora of microenvironments for microorganisms, and these microenvironments can vary within the biocatalyst. Thus, some microenvironments may change the composition of the water such that other microenvironments may be under conditions more favorable for the metabolic reduction. For instance, where the water contains oxygen, the microorganisms may metabolize the oxygen and provide an oxygen-depleted water that passes to other microenvironments where conditions favor metabolic reduction. Hence, the biocatalyst serves to provide a self-modulation of the metabolic reduction. In some embodiments of this invention, external modulation of the metabolic reduction conditions can be effected by the rate of supply of electron donor. In general, the more electron donor, the more acidic the pH within the biocatalyst. Since the modulation is within the interior of each biocatalyst structure, the biocatalytic activities of the biocatalysts in a reaction zone can be relatively uniform.

Often at least a portion of the solid metabolic product remains in the cell or otherwise in the biocatalyst. In other instances, the metabolic product is removable from the biocatalyst. If desired, the water from the bioreactor may be subjected to a solids removal unit operation such as ultrafiltration, settling, centrifugation, and the like. As described above, with some systems, it is possible to regenerate the porous matrices. Alternatively the biocatalyst can provide a concentrated source of the metal or semi-metal for disposal or recovery.

Representative reducing microorganisms include, but are not limited to, those of genera *Saccharomyces*; sulfur-reducing bacteria including genera *Proteus, Campylobacter, Pseudomonas, Salmonella, Desulfuromonas, Desulfovibrio, Desulfonema*; phosphorus reducing bacteria including genera *Acinetobacter, Phormidium, Rhodobacter*, and *Staphylococcus*; uranium reducing bacteria including *Desulfovibrio, Deinococcus, Geobacter, Cellulomonas, Shewanella*, and *Pseudomonas*; molybdate reducing organisms including genera *Serratia, Enterobacter*, and *Escherichia*; cadmium reducing bacteria including genera *Pseudomonas* and *Klebsiella*.

Some preferred microorganisms for specific types of soluble compounds are as follows. selenate-reducing bacteria including *Enterobacter cloacae, Planomicrobium mcmeekinii, Psuedomonas alcaligenes, Psuedomonas denitrificans, Psueomonas stutzeri*, and *Roseomonas genomospecies*; other selenium-reducing microorganisms including those disclosed in U.S. Pat. No. 7,815,801, herein incorporated by reference in its entirety; chromate-reducing organisms including *Enterobacter cloacae, Desulfovibrio vulgaris, Geobacter sulfurreducens, Psuedomonas chromatophilia, Psuedomonas fluorescens*, and *Swanella alga*; ferric ion reducing microorganisms including those from the genera *Ferribacterium, Geobacter*, and *Geothrix*; and arsenate reducing bacteria including those from the genera *Geobacter, Corynebacterium, Pseudomonas, Shewanella*, and *Hydrogenophaga*.

vii. Taste and Odor Removal from Water

Algal metabolites in sources of drinking water can result in a characteristic bad flavor and unpleasant odor. It is believed that the flavor and unpleasant odor is due to the presence of 2-methylisoboreal (MIB) and trans-1,10-dimethyl-trans-decalol (geosmin). Humans can detect levels of MIB as low as 5 to 10 parts per trillion. Geosmin is similarly detected at very low levels. Other possibilities for objectionable drinking water are halogenated organic substances, such as trihalomethanes, which are derived from a combination of chlorine and bromine with organic halogenated components of the water. Disinfection byproducts such as halogenated organic compounds may also be present, often at higher concentrations. The removal of these halogenated organic compounds is desirable for organoleptic and public health reasons. The removal of the algal metabolites and halogenated components from drinking water is particularly problematic due to the low concentrations to which these impurities must be lowered.

The biocatalysts of this invention are able to treat water containing ultra-low concentrations of contaminants including these algal metabolites and halogenated organic compounds, and reduce their concentrations to acceptable levels. Significantly, due to the phenotype alterations of the microorganisms in the biocatalyst, a stable, high population of microorganisms can exist within the without the need for excessive electron donor to support the microorganism population. The processes for using the biocatalysts of this invention for reducing the concentration of ultra-low contaminants in a water stream comprise:

a. continuously passing said water stream to a bioreactor, said bioreactor being maintained at metabolic conditions including the presence of the biocatalyst, said biocatalyst having microorganisms capable of bioconversion of said ultra-low contaminants irreversibly retained therein;

b. contacting said water stream with said biocatalyst for a time sufficient to reduce the concentration of said ultra-low contaminants; and c. withdrawing from said bioreactor a treated water stream having a reduced concentration of said ultra-low contaminants.

Preferably, each of the ultra-low contaminants is present in a concentration in the water stream the passed to the bioreactor in an amount of at least about 40, say at least about 50, nanograms per liter (ng/L) and less than about 50, often less than about 20, micrograms per liter (mcg/L). The ultra-low contaminants preferably comprise algal metabolites such as MIB and geosmin. The contaminants may also include halogenated organic compounds such as disinfection byproducts such as trihalomethanes (THM) and halo-acetic acid (HAA) each of which may be present in amounts of 1 to 1000 micrograms per liter. After treatment, the concentration of the ultra-low contaminants in the treated water is typically below about 40, preferably below about 20, and sometimes below about 10, nanograms per liter. Frequently, the halogenated organic compounds in the treated water are at concentrations of less than about 70, preferably less than 50, micrograms per liter.

The processes of this invention are suitable for use with any microorganism capable of low concentration bioconversions. The preferred microorganisms are from the genus *Rhodococcus*. The genus *Rhodococcus* is a very diverse group of bacteria that possesses the ability to degrade a large number of organic compounds. They have a capacity to acquire a remarkable range of diverse catabolic genes and have robust cellular physiology. *Rhodococcus* appear to have adopted a strategy of hyperrecombination associated with a large genome. Notably, they harbor large linear plasmids that contribute to their catabolic diversity by acting as 'mass storage' for a large number of catabolic genes.

In many instances the metabolic conditions do not require the addition of electron donor in order to maintain the metabolic activity of the porous matrices as the ultra-low contaminants and other contaminants in the water are sufficient to provide the needed electron donor. Where electron donor is desired to be added, it is preferably in a concentration that will be essentially completely metabolized by the biocatalyst, i.e., the electron donor will be provided in an amount insufficient to maintain the population of the microorganisms in the bioreactor.

In some instances the average hydraulic residence time of the water being treated in the bioreactor is less than about 5, preferably less than about 2, hours, and may be in the range of between about 10 and 50 minutes. Often the biocatalyst can retain metabolic activity for at least about 50, say, at least about 250, days. It is possible that the microorganisms can be maintained for decades or more. The preferred biocatalysts can maintain desired metabolic activity (e.g., within about 3 to 5 days of restart) after extended periods of shutdown, say, between about 100 and 500 days.

The metabolic processes may be conducted in any suitable manner and may be under Typical Mesophilic Conditions using Typical Bioreactor Systems. The process may be on a continuous, semi-continuous or batch mode of operation, but is preferably continuous. The oxygenation is preferably at least about 1, more preferably at least about 2, and sometimes between about 2 and 10 or more, milligrams of free oxygen per liter. If needed, electron donors can be added to the water to be treated. Electron donors include, but are not limited to, hydrogen, carbohydrates, hydrocarbons, alkanols, aldehydes, carboxylic acids, ketones, aldehydes, glycerides and the like. See, for instance, paragraph 0055 of U.S. Published Patent Application No. 2006/0263869. If electron donors are required, they may be added in any suitable manner. Usually the amount added is sufficient to provide the sought biodegradation.

The degradation products may be removed from the water in any suitable manner including using Typical Separation Techniques.

Example 223

A 4 liter capacity continuously stirred tank bioreactor is filled to about 30 percent of its volume with biocatalyst substantially as described in Example 72. A water feed stream is continuously passed to the bioreactor at room temperature (22° C.) at a rate sufficient to provide an approximate hydraulic residence time of about 30 minutes. The water is from a fresh water reservoir which has not been treated. MIB and geosmin are each provided in an amount of about 400 nanograms per liter (adding MIB and geosmin where required to approximate the target concentration levels). The fresh water does contain algal metabolites as can be detected by odor and taste. The water has a pH of about 7 and at least 4 parts per million by mass of dissolved oxygen per liter. The concentration of MIB is reduced to less than 5 nanograms per liter and geosmin to less than about 20 nanograms per liter. The treated water from the reactor has no detectible odor or taste.

The reactor is shut down for about 6 months (no water flow through the reactor) and maintained at room temperature. Upon restart by passing a similar water stream through the bioreactor under substantially the same conditions, within one day, the water discharged from the reactor does not have a detectible odor or taste. viii. 1,4-Dioxane Removal from Water Animal studies have shown that inhalation and ingestion of 1,4-dioxane can lead to the formation of nasal cavity and liver carcinomas along with neurotoxic effects. 1,4-Dioxane has come into water resources primarily from use as a solvent stabilizer for solvents used in various cleaning and degreasing applications, especially chlorinated solvents, such as trichloroethane (TCA) and trichloroethylene (TCE). 1,4-Dioxane is also detected in consumer products, such as shampoos, soaps, waxes and lotions, as a result of contamination of ethoxylated compounds, such as sodium laureth sulfate. States such as California, Massachusetts, Florida and North Carolina have set drinking water standards for 1,4-dioxane at low parts per billion (ppb) levels.

Biodegradation of 1,4-dioxane is problematic. The presence of chlorinated solvents has an inhibitory effect on microorganisms identified to degrade 1,4-dioxane; inducing compounds such as propane or tetrahydrofuran (THF) are required for many microorganisms to degrade 1,4-dioxane, but are themselves contaminants; and microorganisms that do not require inducing compounds tend to be less robust and slow growing.

The biocatalyst of this invention are particularly attractive for use in processes to reduce the concentration of 1,4-dioxane in a water stream. In some instances the use of an inducing compound is not required even though the water contains both 1,4-dioxane and a halogenated compound. These processes comprise:

a. continuously passing said water stream to a bioreactor, said bioreactor being maintained at metabolic conditions including aerobic conditions and the presence of biocatalyst of this invention containing microorganisms adapted to degrade 1,4-dioxane metabolically;
b. contacting said water stream with said biocatalyst for a time sufficient to reduce the concentration of said 1,4-dioxane in the water stream; and
c. withdrawing from said bioreactor a treated water stream having a reduced concentration of 1,4-dioxane.

The preferred microorganisms used in the biocatalyst are from the *Rhodococci* genus, *Pseudonocardia dioxanivorans*, and *Pseudonocardia benzenivorans*. Preferred processes include those where 1,4-dioxane is present in the water stream in an amount less than about 100 micrograms per liter and the treated water stream has a concentration of 1,4-dioxane of less than about 10 micrograms per liter. In some instances, 1,4-dioxane is present in the water stream in an amount greater than about 10 micrograms per liter and the treated water stream has a concentration of 1,4-dioxane of less than about 5 micrograms per liter.

In many instances, no additional carbon source is required to maintain the population of the microorganisms in the biocatalyst due to the microenvironment and phenotypic alterations. However, at low concentrations of 1,4-dioxane in the water to be treated, the addition of minor amounts of carbon source may be advantageous to support the energetic robustness of the population. Nevertheless, the metabolic activity of the biocatalysts can be sufficient to assure that substantially no biodegradable carbon is contained in the treated water.

The metabolic processes may be conducted in any suitable manner including Typical Mesophilic Conditions and using Typical Bioreactor Systems. The process may be on a continuous, semi-continuous or batch mode of operation, but is preferably continuous. The oxygenation is preferably at least about 1, more preferably at least about 2, and sometimes between about 2 and 10 or more, milligrams of free oxygen per liter. If needed, electron donors can be added to the water to be treated. Electron donors include, but are not limited to, hydrogen, carbohydrates, hydrocarbons, alkanols, aldehydes, carboxylic acids, ketones, aldehydes, glycerides and the like. Acetone or glucose is a convenient electron donor. See, for instance, paragraph 0055 of U.S. Published Patent Application No. 2006/0263869. If electron donors are required, they may be added in any suitable manner.

The degradation products may be removed from the water in any suitable manner including using Typical Separation Techniques.

Example 224

A 4 liter, airlift, downflow bioreactor with a perforated plate equipped with diffusers to provide uniform aeration of the bioreactor is loaded with 3000 grams of the biocatalyst of example 48. An air pump provides air to the bioreactor below the perforated plate in an amount sufficient to maintain the biocatalyst suspended. Water to be treated is continuously added to the liquid phase above the perforated plate using a variable-speed pump.

The water to be treated is deionized water to which components are added. Acetone, ammonium chloride and dipotassium biphosphate are added as necessary to maintain an atomic ratio of carbon:nitrogen:phosphorus in the water of 100:3:1. The atomic carbon is calculated as the total carbon in the components added to the water. The dissolved oxygen in the bioreactor is between about 5 and 7 milligrams per liter (as determined by an Oakton DO6 Acorn Series meter and probe). The bioreactor is operated at room temperature (about 21° to 25° C.) and an average hydraulic residence time of 5 hours, and a pH of between about 7 and 8 is maintained in the bioreactor.

The water is first spiked with about 71,000 micrograms per liter of 1,4-dioxane. After completion with that run, the water is spiked with 100 micrograms per liter of 1,4-dioxane and 50 micrograms of acetone per liter. The concentration of 1,4-dioxane in the efflux is determined by gas chromatography and is in both instances is below the non-detect limit of the gas chromatograph of about 2 micrograms per liter.

Additionally, unfiltered effluent from the bioreactor is plated on agar plates (LBB+glucose). After a 5-day incubation, colonies (if any) were counted. Substantially no colonies are observed indicating that the microorganisms are substantially irreversibly retained in the biocatalyst.

The results are indicative that the biocatalysts require very little induction time before effective removal of 1,4-dioxane occurs and that the 1,4-dioxane concentration can be reduced to non-detect levels at both higher and lower initial concentrations.

ix. Succinic Acid

The biocatalysts of this invention can be used to convert sugars to succinic acid. In the broad aspects, the processes for the bioconversion of sugar and optionally carbon dioxide using a biocatalyst containing succinic acid-producing microorganism comprise:

a. contacting an aqueous medium with said biocatalyst under metabolic conditions including temperature and the presence of sugar and other nutrients for the microorganism for a time sufficient to produce succinate anion and provide a succinate anion-containing aqueous medium;
b. removing at least a portion of said succinate anion-containing aqueous medium and said biocatalyst;

c. reusing in step (a) said biocatalyst from which at least a portion of said succinate anion-containing aqueous medium has been removed; and d. recovering succinate anion from said succinate anion-containing aqueous medium.

Examples of succinic anion-producing microorganisms heretofore disclosed include, but are not limited to, natural or genetically modified microorganisms such as *Mannheimia succiniciproducens, Anaerobiospirillum succiniciproducens, Actinobacillus succinogenes, Alcaligenes eutrophus, Aspergillus niger, Bacillus, Bacteroides fragilis, Bacteroides ruminicola, Bacteroides amylophilus, Brevibacterium ammoniagenes, Brevibacterium lactofermentum, Candida brumtii, Candida catenulate, Candida mycoderma, Candida zeylanoides, Candida paludigena, Candid sonorensis, Candida utilis, Candida zeylanoides, Citrobactor freundii, Corynebacterium glutamicum, Debaryomeces hansenii, Enterococcus faecalis, Escherichia coli* (*E. coli* strains SB550 MG pHL 413, KJ122 and TG400), *Fibrobacter succinogenes, Fusarium oxysporum, Gluconobacter oxydans, Glyconobacter asaii, Humical lanuginosa, Kloeckera apiculata, Kluyveromyces lactic, Kluyveromyces wickerhamii, Paecilomcyes varioti, Penicillum simplicissimum, Pichia anomala, Pichia besseyi, Pichia media, Picha guiliermondii, Pichia inositovora, Pichia stipidis, Rhizobium, Saccharomyces cerevisiae, Saccharomyces bayanus, Schizosaccharommyces, Schizosaccharomyces pombe, Torulopsos candida, Veillonella parvula, Wollinella succinogenes* and *Yarrowia lipolytica*.

The metabolic processes may be conducted in any suitable manner. The substrate comprises carbohydrate, including $C_5$ and $C_6$ sugars, and may include carbon dioxide. Due to the use of the biocatalyst, sugars less preferred for bioconversion may be effectively used by the microorganisms. The concentration of sugars used in the aqueous medium may fall within a wide range. Generally, sugars are present in a concentration in the aqueous medium of at least about 0.5, say, between about 1 and 200, grams per liter. Preferably, the amount of sugar provided in the aqueous medium is such that at least about 90, more preferably, at least about 95, mass percent is consumed during the metabolic process.

The carbon dioxide may be obtained from any suitable source; however, components that are unduly deleterious to the microorganisms should be removed prior to contact with the aqueous medium containing the biocatalyst. Generally carbon dioxide is supplied in gaseous form, although carbonate and bicarbonate salts can be used. Where supplied as a gas, the carbon dioxide concentration in the gas is typically the range of about 40 to 100, say, 70 to 100, volume percent. Sources of carbon dioxide include, but are not limited to, off gases from industrial and fermentation processes, exhaust gases from combustion of fuels and waste materials, natural gas streams containing carbon dioxide, streams from the gasification of biomass, e.g., to produce syngas, and the like.

The aqueous medium contains water which may be provided from any suitable source including, but not limited to, water, demineralized water, distilled water, and process or waste water streams. Any suitable metabolic conditions can be used including Typical Mesophilic Conditions. Where gaseous substrates are used, higher pressures tend to increase the amount of substrate dissolved in the culture liquid and thus enhance mass transfer. Often the pH is between about 3 and 8.5, say, 3.5 to 7. The metabolic conditions for the bioconversion of sugars and carbon dioxide to succinate anion are typically anaerobic, and preferably, the aqueous medium has a dissolved molecular oxygen concentration of less than about 0.5 milligrams per liter. Where the biocatalyst is cycled to different aqueous media, and one of the aqueous media is intended to provide metabolic activities to enhance the viability of the microorganisms, the dissolved molecular oxygen concentration may be in excess of about 2, say, about 2 to 10, milligrams per liter.

The duration of contact between the aqueous medium and biocatalyst can also fall within a wide range and will depend, in part, upon the concentration of substrate, the concentration of succinate anion sought in the aqueous medium, the type of bioreactor, the other metabolic conditions used, the nature of the microorganism used, and the type of microorganism and cell density in the biocatalyst. For batch operations, the contact is often in the range of about 5 minutes to 100 hours, say, about 1 to 50, hours, and in continuous operations, the liquid hourly space velocity is typically in the range of about 0.01 to 50 $hr^{-1}$.

The bioconversion may be on a continuous, semi-continuous or batch mode of operation. Any suitable bioreactor design may be used including Typical Bioreactor Systems.

In preferred aspects, the biocatalyst is subjected to two or more aqueous environments to enhance the bioconversion of sugars, reduce the presence of non-consumed sugars in the succinic acid-containing fermentation product, and enhance the use of carbon dioxide as a co-substrate.

In one embodiment of the preferred processes, the contacting of the aqueous medium with the biocatalyst occurs in at least two reaction zones having different metabolic conditions. In one aspect of this embodiment, aqueous medium from a first reaction zone containing the biocatalyst is passed to a subsequent reaction zone for further contact with biocatalyst. Substantially no additional sugar is added to the aqueous medium either immediately prior to passing to the subsequent reaction zone or during its residence time in the subsequent reaction zone. Thus, the sugar concentration in the aqueous medium is further depleted in the subsequent reaction zone, preferably to less than about 1, say, less than about 0.5, mass percent based upon the mass of succinate anion in the aqueous medium. Preferably, the first reaction zone and the subsequent reaction zone are cycled. In some instances, it may be desired to supply carbon dioxide substrate to the aqueous medium in the subsequent reaction zone to convert additional phosphoenolpyruvate in the microorganisms to succinate anion.

In another aspect of this preferred embodiment, a reaction zone containing the biocatalyst is cycled between using an aqueous sugar substrate and an aqueous or gaseous carbon dioxide substrate. For instance, sugar is provided in a first aqueous medium contacting the porous matrices in a the first reaction zone, which may be under conditions sufficient to generate phosphoenolpyruvate in the microorganisms under conditions not favoring conversion of the phosphoenolpyruvate to succinate anion which conditions may comprise micro-aerobic or aerobic conditions. The first aqueous medium is withdrawn. A second aqueous medium or gas is introduced into the first reaction zone under anaerobic conditions, including the presence of carbon dioxide, sufficient to bioconvert phosphoenolpyruvate to succinate anion. As the biocatalyst provides environments retaining nutrients for the microorganisms in the metabolic activity of the microorganisms in the second zone can be maintained. Preferably the second zone uses an aqueous medium that is substantially water such that succinate anion product passing into the second aqueous medium can more easily be recovered. Most preferably, the concentration of the succinate anion in the second aqueous medium is at least about 150, say, at least about 200 to as much as 300 or 400, grams per liter of aqueous medium. The second aqueous medium containing succinate anion is removed from the first reaction zone for recovery of the succinate anion. In some instances, succinic acid of high purity can be obtained by reducing the temperature of the aqueous medium sufficient to crystallize a succinic acid. After removal of the second aqueous medium, the first reaction zone can be contacted with a first aqueous medium. In some instances, a third or even further stages can be used. For example, after the removal of the second aqueous medium the first reaction zone can be contacted with a first aqueous medium from it or another reaction zone and maintained under conditions to reduce metabolites in the aqueous medium and generate more phosphoenolpyruvate. If desired, multiple reaction zones can be used in order to provide a semi-continuous process.

The succinic acid product may be recovered from the aqueous medium in any suitable manner. Various methods for recovery of succinic acid include precipitation, and membrane separations, sorption and ion exchange, electro dialysis, and liquid-liquid extraction. See, for instance, Davidson, et al., Succinic Acid Adsorption from Fermentation Broth and Regeneration, Applied Biochemistry and Biotechnology, Spring 2004, pages 653-669, for a discussion of sorbents for succinic acid recovery from fermentation broths. See also, Li, et al., Separation of Succinic Acid from Fermentation Broth Using Weak Alkaline Anion Exchange Adsorbents, Ind. Eng. Chem. Res., 2009, 48, pages 3595-3599. See, for instance, a multiple crystallization method for recovery of succinic acid disclosed in U.S. Patent Application Publication No. 2011/0297527. Hepburn, in his Masters thesis at the Queen's University, The Synthesis of Succinic Acid and its Extraction from Fermentation Broth Using a Two-Phase Partitioning Bioreactor (April 2011), discloses a process where such cynic acid is produced to inhibitory levels, and then the pH of the system was suggested below the $pK_{A2}$ of succinic acid using dissolved carbon dioxide gas to create undissociated product. Polymers with an affinity for succinic acid absorbed from the solution, and then the pH was returned to operational levels.

Figure 10:
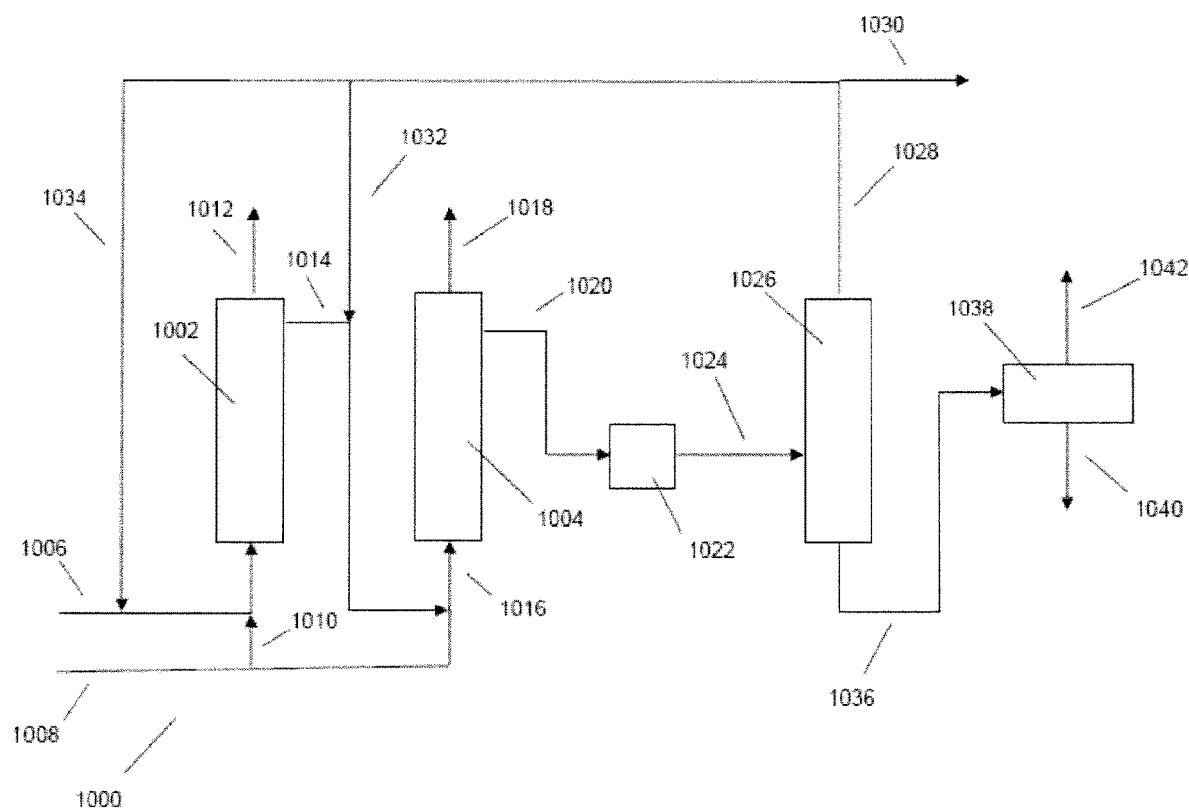
FIG. 10 is a schematic depiction of an apparatus suitable for using biocatalysts of this invention for making succinic acid, which apparatus uses sequential reactors.
Figure 11:
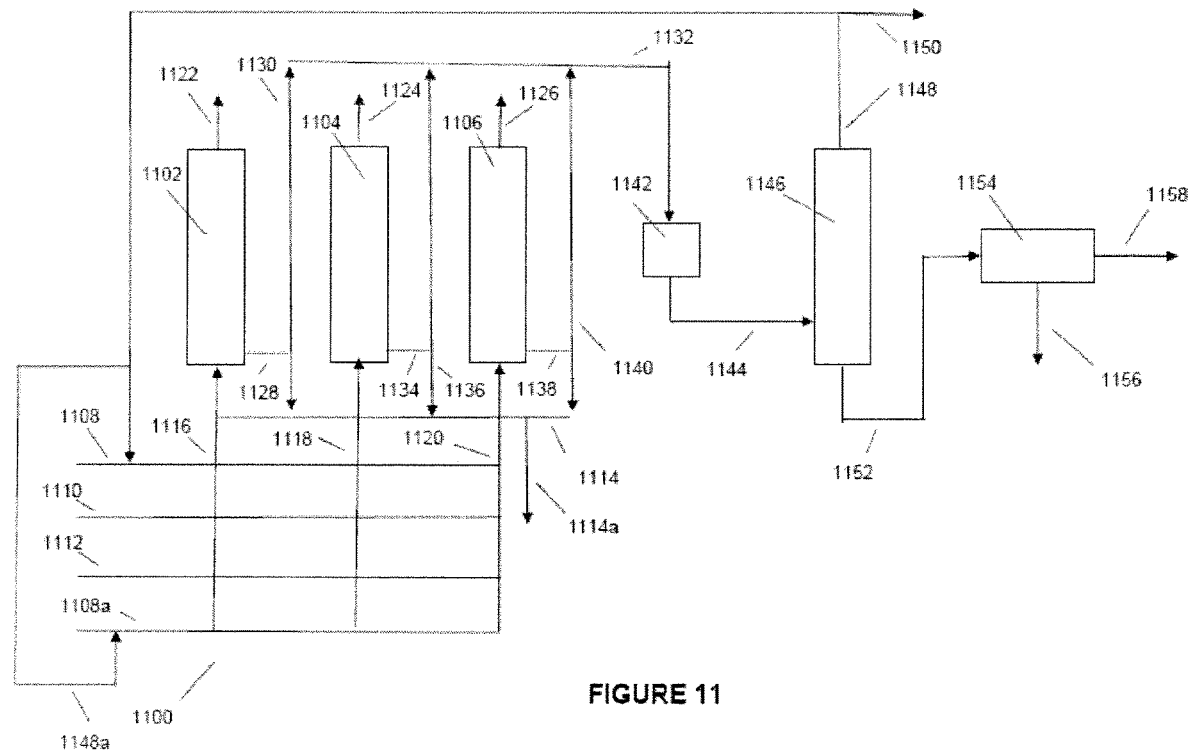
FIG. 11 is a schematic depiction of another apparatus suitable for making succinic acid wherein reactors are cycled from PEP generation to succinate anion generation using carbon dioxide.

A general understanding of this process may be facilitated by reference to the FIGS. 10 and 11. With reference to FIG. 10, apparatus 1000 is suitable for the biological production of succinic acid on a continuous basis. Apparatus 1000 is depicted as having a primary bioreactor 1002 and a polishing bioreactor 1004. Both bioreactors are fluidized bed reactors containing biocatalyst, e.g., substantially s described in Example 175. An aqueous stream containing sugar and other nutrients is supplied by line 1006 to bioreactor 1002. Carbon dioxide-containing gas is supplied to the apparatus 1000 via line 1008. A portion of the carbon dioxide-containing gas is passed by line 1010 to line 1006 into bioreactor 1002. Bioreactor 1002 is maintained under metabolic conditions sufficient for conversion of sugar and carbon dioxide to succinate anion. Off gases are removed from bioreactor 1002 by line 1012. A continuous stream of the aqueous medium in bioreactor 1002 is withdrawn by line 1014 and passed to a bioreactor 1004. Bioreactor 1002 is provided with a screen or other device to essentially prevent biocatalyst passing into line 1014. To bioreactor 1004 is provided carbon dioxide-containing gas from line 1008 and line 1016.

In a typical operation of apparatus 1000, the aqueous medium withdrawn from bioreactor 1002 via line 1014 contains unreacted sugars and metabolites that can be further bioconverted by the microorganisms. Bioreactor 1004 is operated to further reduce the concentration of the unreacted sugars and these metabolites and thus no additional sugar substrate is provided to a bioreactor 1004 in such an operation. It should be readily understood that if desired, additional sugar substrate could be added to the aqueous medium in bioreactor 1004.

Bioreactor 1004 is operated under metabolic conditions sufficient to convert substrate to succinate anion. Unreacted gases are withdrawn from bioreactor 1004 through line 1018. A continuous stream of aqueous medium from bioreactor 1004 is withdrawn via line 1020. Bioreactor 1004 is provided with a screen or other device to essentially prevent biocatalyst from being passed into line 1020. The withdrawn aqueous medium is directed to filtration assembly 1022 by line 1020. As the aqueous medium is substantially devoid of solids, it is practical for filtration assembly 1022 to be an ultrafiltration assembly. The aqueous medium is then passed from filtration assembly 1022 via line 1024 to distillation column assembly 1026. In the event that bioreactors 1002 and 1004 are operated substantially unbuffered, distillation column assembly 1026 serves to concentrate the aqueous medium to facilitate crystallization of the succinic acid. Where an ammonium hydroxide buffer is used, distillation column assembly 1026 also serves to convert ammonium salts of succinate anion to succinic acid with ammonia being released. Distillation column assembly 1026 may comprise one or more unit operations including neutralization and filtration of precipitates, intermediate crystallization and re-solvation such as disclosed in U.S. Patent Application Publication No. 2011/0297527, and the like.

As shown, the overhead from distillation column assembly 1026 exits via line 1028. A purge can be taken via line 1030 and the remaining overhead recycled to one or both of bioreactors 1002 and 1004 via lines 1034 and 1032, respectively. Where ammonium hydroxide buffer is used, the recycle reduces the amount of ammonium hydroxide required to be externally provided. It is also possible to operate bioreactor 1004 at a lower pH than that used in bioreactor 1002. Thus, in a buffered system, the predominant portion of the succinate anion will be the mono salt.

The bottoms stream from distillation column 1026 is passed via line 1036 to crystallization unit 1038. Typically, the concentration of succinic acid in the bottoms stream is greater than about 30%. The bottoms stream passing to the crystallization unit is often cooled to a temperature below about 15° C., say, between about 0° and 10° C. Crystalline succinic acid is removed from crystallization unit 1038 via line 1040. The supernatant liquid is removed via line 1042.

FIG. 11 depicts an apparatus 1100 having three bioreactors 1102, 1104, and 1106 that are operated on a sequential, cyclic routine to bioconvert sugar and carbon dioxide to succinic acid. Each of the reactors contain porous matrices having succinic acid-producing microorganisms irreversibly retained therein. The bioreactors have an internal liquid recycle system to be operated as fluid bed reactors.

Apparatus 1100 is provided with four headers: header 1108 which provides fresh aqueous medium containing sugar and other nutrients; header 1110 which provides carbon dioxide-containing gas; header 1112 which provides oxygen-containing gas and header 1114 which provides for fluid transport between the bioreactors. Line assemblies 1116, 1118, and 1120 connect each of the four headers 1108, 1110, 1112, and 1114 with bioreactors 1102, 1104, and 1106, respectively. Each of bioreactors 1102, 1104 and 1106 are provided with lines 1122, 1124 and 1126, respectively, to permit the egress of gas and are provided with lines 1128, 1134 and 1138, respectively, to drained aqueous medium from the bioreactors. The drained aqueous medium from a bioreactor is directed either to header 1132 or header 1114.

For bioreactor 1102 line 1128 is in flow communication with line 1130 which is adapted to direct the aqueous medium to one of these headers. For bioreactor 1104 line 1134 is in flow communication with line 1136 which is adapted to direct the aqueous medium to one of these headers. For bioreactor 1106 line 1138 is in flow communication with line 1140 which is adapted to direct the aqueous medium to one of these headers.

Each of bioreactors 1102, 1104 and 1106 are sequenced between a microaerobic stage, an anaerobic, sugar conversion stage, and a carbon dioxide conversion stage. In the microaerobic stage, fresh aqueous medium is supplied to a bioreactor that has completed the carbon dioxide conversion stage and has been drained of aqueous medium for purposes of succinic acid recovery. In this regard, small amounts of oxygen-containing gas, e.g., air, are provided from header 1112.

At the conclusion of the microaerobic stage, supply of oxygen-containing gas from header 1112 is ceased and the bioreactor enters the anaerobic, sugar conversion stage. The anaerobic, sugar conversion stage may be conducted with or without the addition of carbon dioxide from header 1110. The anaerobic, sugar conversion stage is conducted under metabolic conditions suitable for the production of succinate anion. In some embodiments, the metabolic conditions during the microaerobic stage and the anaerobic, sugar conversion stage enhance the formation of phosphoenolpyruvate with relatively little succinate anion being passed from the porous matrices into the surrounding aqueous medium.

The reactor then passes from the anaerobic, sugar conversion stage to the carbon dioxide conversion stage. In the carbon dioxide conversion stage carbon dioxide is supplied from header 1112 in an amount sufficient to enhance a portion of the succinate anion being derived from carbon dioxide substrate through the conversion of phosphoenolpyruvate. The bioreactor is maintained under metabolic conditions favoring the bioconversion of carbon dioxide substrate. At the conclusion of the carbon dioxide conversion stage, the aqueous medium is drained from the bioreactor and is passed to header 1132 for succinic acid recovery. The reactor then cycles back to the microaerobic stage.

As with the apparatus depicted in FIG. 10, apparatus 1100 passes the aqueous medium withdrawn from the bioreactor having gone through the carbon dioxide conversion stage to filtration assembly 1142 and then via line 1144 to distillation assembly 1146. The overhead from distillation assembly 1146 exits via line 1148 for recycle to header 1108. A purge is taken via line 1150. The bottoms stream from distillation assembly 1146 is passed via line 1152 to crystallization assembly 1154. Succinic acid is withdrawn via line 1156, and the supernatant liquid is removed via line 1158.

Apparatus 1100 can also be operated using a different sequence of stages. One such sequence uses water having a substantial absence of sugars and other nutrients in the carbon dioxide conversion stage. For description of this sequence, reference is made to header 1108a which supplies such a water stream.

In the microaerobic stage, the aqueous medium is supplied by another bioreactor that has completed the anaerobic, sugar conversion stage. At the conclusion of the microaerobic stage the bioreactor enters into the anaerobic, sugar conversion stage as described above, but under conditions that minimize the accumulation of succinate anion in the aqueous medium. Sugar and other nutrients are provided to the bioreactor via header 1108. The sugar and other nutrients are preferably dissolved or slurry in an aqueous medium at a sufficient concentration to maintain the sought amount of aqueous medium in the bioreactor as well as sufficient concentrations of the sugars and other nutrients for the metabolic activity of the microorganisms.

At the completion of the anaerobic, sugar conversion stage, the aqueous medium is withdrawn and passed to a bioreactor entering into the micro-aerobic stage. The aqueous medium is replaced with water having a substantial absence of sugar and other nutrients. In the carbon dioxide conversion stage, sufficient carbon dioxide is provided to provide, under metabolic conditions, succinate anion. Succinic anion passes into the water phase which will have reduced concentrations of sugars, other nutrients, and other metabolites as compared to the aqueous medium in the anaerobic, sugar conversion stage. Thus, the ability to obtain high purity succinic acid is facilitated. Moreover, by recycling the aqueous medium from the bioreactor completing the anaerobic, sugar conversion stage to the microaerobic stage, certain metabolites such as acetate anion may be consumed by the microorganisms for metabolic purposes thereby enhancing the conversion of sugars to succinate anion.

In this sequence, a purge stream is taken from header 1114 via line 1114a to prevent undue buildup of undesired components in the aqueous medium, and overhead from distillation assembly 1146 can be used to make up at least part of the water for the water supplied by header 1108a via line 1148a.

x. *Botyrococci*

*Botryococcus*, including, but not limited to, *Botryococcus braunii*, have been proposed for the photosynthetic conversion of carbon dioxide to various hydrocarbon and oxygenated organic compound bioproducts, often of 8 or 10 to 50 carbon atoms, and sometimes between about 20 and 40, carbon atoms ("oils"). *Botryococcus* species have been reported that have up to 75 percent of the dry mass of the microalgae constituting hydrocarbons whereas other microalgae may only contain up to about 10 mass percent hydrocarbons. *Botryococcus* species often have a high productivity of bioproducts. The bioproducts may be expressed from the cells and depending on the strain or race of the species can include odd-numbered hydrocarbons, n-alkadienes, trienes, triterpene hydrocarbons, and tetraterpene hydrocarbons. The hydrocarbons can contain oxygen in various functional groups.

Although *Botryococcus* species offer significant potential as a source of biochemicals and biofuels, the practical difficulties associated with providing and maintaining a sufficient population of *Botryococcus* species have hindered their adoption on a commercial scale. These difficulties include having:

a very slow growth rate;
an oil secretion is primarily in the non-growing phase thus proposals have been made to harvest the algae once a sufficient population has been obtained for oil recovery;
sensitivity to strong light causing chlorophyll degeneration which may be long lasting or permanent;
thick cell walls that are resistant to chemical degradation and hinder oil extraction;
sensitivity to hydrodynamic shear; and
an impracticability to use a bioreactor of sufficient size to be competitive for supplying oils free of contaminating microorganisms that may consume oils, compete for nutrients and produce algaecides.

The biocatalysts of this invention that contain *Botryococcus* species take advantage of the metabolic activity of *Botryococcus* species to provide enhanced process viability. In the broad aspects, the processes for the bioconversion of carbon dioxide to bioproducts using biocatalyst of this invention which contains microalgae comprising a species of *Botryococcus* comprises:

a. maintaining the biocatalyst in an aqueous medium, said aqueous medium being at metabolic conditions including temperature and the presence of nutrients for the microalgae;
b. contacting the aqueous medium with carbon dioxide for the bioconversion wherein the microalgae secretes bioproduct;
c. irradiating the aqueous medium with light at a frequency and intensity sufficient for the microalgae to photosynthesize carbon dioxide to bioproduct; and
d. removing bioproduct from the aqueous medium.

The bioconversion may be photosynthetic or heterotrophic where the microalgae have the ability to operate in such an environment, or both. Preferably the biocatalyst has a smallest dimension of less than about 15, preferably less than about 2, millimeters, say, between about 100 microns and 2 millimeters.

The processes of this invention use microalgae comprising species of *Botryococcus*. Preferably the microalgae consist essentially of species of *Botryococcus*, i.e., a monocultural environment exists for the photosynthetic conversion of carbon dioxide to bioproduct, or a multicultural environment with bacteria that can enhance the performance of *Botryococcus* species such as disclosed in Wang, et al., Effect of nutrient conditions on the growth of *Botryococcus braunii*, Chinese Journal of Process Engineering, 3:141-145 (1996), hereby incorporated by reference in its entirety. The species of *Botryococcus* can be a wild type (naturally occurring) or a recombinant microalgae. Examples of species of *Botryococcus* include, but are not limited to, *Botryococcus braunii*. Numerous strains of *Botryococcus braunii* are known such as *horridus, minor, perarmatus, validus, Showa* and *Ninsei*. Other species of *Botryococcus* include, *B. australis, B. calcareous, B. canadensis, B. comperei, B. fernanoi, B. giganteus, B. miromorus, B. neglectus* and *B. pila*. Strains can be further categorized into races such as *Botryococcus braunii* race A, *Botryococcus braunii* race B, and *Botryococcus braunii* race L. Strains of *Botryococcus braunii* are typically preferred due to bioproduct production and rates, especially those of the A and B races, and strains of *Botryococcus braunii* race B are most preferred where bioproducts not containing oxygen atoms are desired.

One advantageous species of *Botryococcus* comprises genetically modified *Botryococcus* containing enzyme for metabolizing carbohydrates source, such as sugar, for heterotrophic growth. This genetic modification facilitates obtaining a large population of *Botryococcus* to be incorporated into the biocatalyst. The population increase may be facilitated through the use of alternative carbon sources such as carbohydrates where the microalgae contain suitable enzymes and transporters. *Botryococcus braunii* typically have transporters for glucose.

The biocatalysts of this invention are used in photosynthetic processes to bioconvert carbon dioxide to bioproducts. The composition of the bioproducts can vary depending upon the strain of *Botryococcus* used, and can be branched or cyclic hydrocarbons, including but not limited to terpenoids of 10 to 50 carbons, and may be substituted with oxygen containing moieties such as hydroxyl, alkoxy, acyl, and carboxyl. The bioproducts can include biodiesel and other glycerides. The bioproducts are expressed from the microalgae, and pass from the porous matrices into the aqueous medium containing the porous matrices. A solvent can be used to facilitate collection of the bioproducts. A preferred solvent is one that is immiscible with water, solubilizes the hydrocarbons or other bioproducts, has a low boiling point, has a density significantly different than water, is readily available and inexpensive, is reusable and recyclable, and is not extremely toxic to the organisms. Heptane is an example of such a solvent.

The metabolic processes may be conducted in any suitable manner. The substrate comprises carbon dioxide and may include carbohydrate, including $C_5$ and $C_6$ sugars. The carbon dioxide may be obtained from any suitable source; however, components that are unduly deleterious to the microalgae should be removed prior to contact with the biocatalyst. Generally carbon dioxide is supplied in gaseous form, although carbonate and bicarbonate salts can be used but are less preferred. Where supplied as a gas, the carbon dioxide concentration in the gas is typically the range of about 40 to 100, say, 70 to 100, volume percent. Sources of carbon dioxide include, but are not limited to, off gases from industrial and fermentation processes, exhaust gases from combustion of fuels and waste materials, natural gas streams containing carbon dioxide, streams from the gasification of biomass, e.g., to produce syngas, and the like.

Suitable metabolic conditions using light radiation in an intensity sufficient to provide photo-biocatalytic activity include culture liquid can be used including Typical Mesophilic Conditions. The light intensity can vary, but is preferably relatively strong, e.g., at least about 20, say, between about 20 and 200 or more, microEinsteins per square meter per second, for light within the wave range of 400 to 800 nanometers. The pressure is not critical and may be ambient, reduced or elevated pressure. Where gaseous substrates are used, higher pressures tend to increase the amount of substrate dissolved in the culture liquid and thus enhance mass transfer. Often the pH is between about 6.5 and 8.5, say, 6.5 to 8.0. The metabolic conditions may include the presence of molecular oxygen, and if present, in an amount of between about 5 to 50 volume percent based upon the volume of carbon dioxide fed to the aqueous medium.

Usually, the bioconversion activity can be maintained for at least about 30, and often for at least about, 300 or more days.

The chemical product may be recovered from the culture liquid in any suitable manner. Continuous or frequent discontinuous removal of the bioproduct is preferred as the bioproduct.

xi. Butanol

The biocatalyst of this invention is attractive for the conversion of substrate to butanol which may be isobutanol or n-butanol. Both isomers of butanol are toxic at relatively low concentrations to microorganisms producing butanol, typically less than about 3 percent by mass per liter of aqueous medium. The processes using the biocatalyst of this invention permit higher titers of butanol to be produced thereby reducing costs of the water/butanol separation. See, for instance, Tracy, "Improving Butanol Fermentation to Enter the Advanced Biofuel Market, mbio.asm.org, vol. 3, 6, November/December 2012, and Kaminski, et al., Biobutanol—Production and Purification Methods, Ecological Chemistry and Engineering S, 18:1, pp. 31-37 (2011).

In the broad aspects, the processes for bioconverting substrate to butanol comprise:

a. contacting an aqueous medium with a biocatalyst of this invention, said biocatalyst containing microorganisms capable of bioconverting said substrate to butanol, wherein said aqueous medium is maintained under metabolic conditions including the presence of nutrients for said microorganisms and contains said substrate;

b. maintaining the contact between the aqueous medium and biocatalyst for a time sufficient to bioconvert at least a portion of said substrate to butanol; and c. recovering butanol from said aqueous medium.

The butanol may be either isobutanol or n-butanol depending upon the microorganism used in the process. The microorganism to be used will also define the substrate. Substrates that have found application in producing butanol include carbon dioxide, sugars, glycerol and syngas. Microorganisms capable to producing butanol are butyrogens and include, but are not limited to, wild-type or recombinant *Clostridia*, such as *C. acetobutylicum, C. beijerinckii, C. pasteurianum, C. saccharobutylicum, C. saccharoperbutylacetonicum; Oeneococcus oeni*; and *Ralstonia eutropha*, and recombinant microorganisms such as *E. coli* into which pathways for making butanol have been added. See, for instance, United States published patent application no 20100143993 for a more extensive discussion of other microorganisms for making butanol. Genetically enhanced photoautotrophic cyanobacteria, algae, and other photoautotrophic organisms have been adapted to bioconvert carbohydrates internal to the microorganism directly to butanol. For example, genetically modified cyanobacteria having constructs comprising DNA fragments encoding pyruvate decarboxylase (pdc) and alcohol dehydrogenase (adh) enzymes are described in U.S. Pat. No. 6,699,696.

Bioconversion conditions are often within Typical Mesophilic Bioconversion Conditions, and Typical Bioreactor Systems can be used. Continuous processes are preferred especially since the biocatalysts of this invention can provide high cell densities and thus, together with the enhanced bioconversion rate, provide for high conversion efficiencies of substrate with relatively brief average residence times in the bioreactor, e.g., often less than about 3 or 4 hours, and sometimes less than about 30 minutes.

Figure 12:
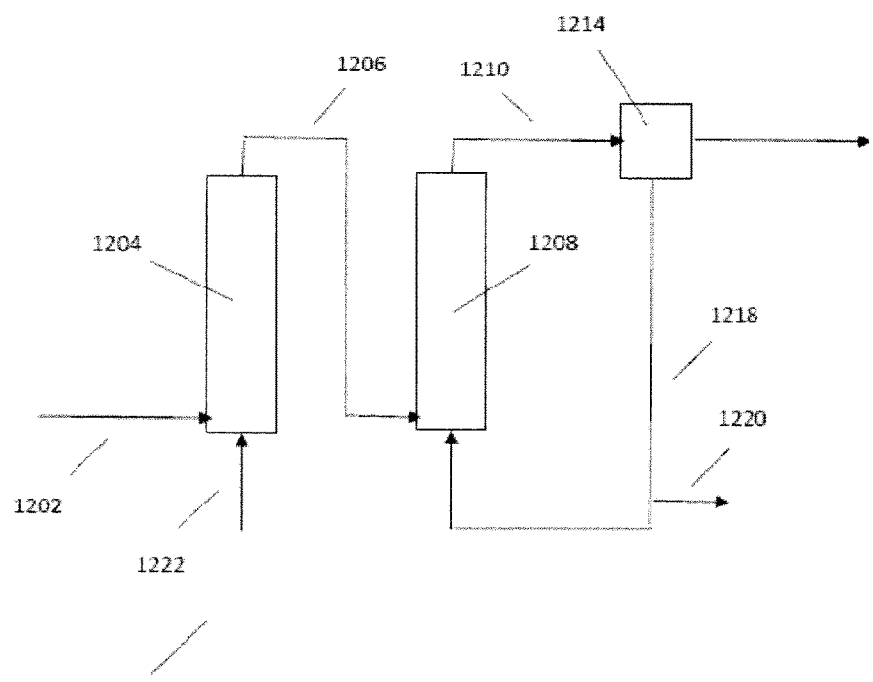
FIG. 12 is a schematic depiction of an apparatus for making butanol in which the butanol is phase separated for recovery.

One aspect of this process is further illustrated in FIG. 12 which is a schematic depiction of a bioreactor assembly 1200 for the production of n-butanol. A sugar-containing feedstock is provided via line 1202 to first bioreactor 1204 which is an up-flow bioreactor containing an aqueous fermentation medium and biocatalyst for the bioconversion of sugar to n-butanol. The biocatalyst contains. In bioreactor 1204, the supply of sugar is such that only a portion is bioconverted to butanol and thus provides an aqueous medium containing about 6 to 8 volume percent butanol. Aqueous medium from first bioreactor 1204 is passed via line 1206 to second bioreactor 1208 where the remaining sugars are bioconverted. Second bioreactor 1208 is a fluidized bed bioreactor. Second bioreactor 1208 contains an aqueous medium with biocatalyst containing *Clostridia acetobutyricum*. In second bioreactor, some of the remaining sugar is bioconverted to provide an aqueous medium containing about 10 volume percent butanol. Due to the higher concentration of butanol in second reactor 1208, the bioconversion rate to butanol is less than about 50 percent of that in first bioreactor 1204. Aqueous medium is withdrawn from second bioreactor 1208 and passed to decanter 1214 via line 1210 to provide an upper phase containing n-butanol which is passed via line 1216 to product recovery. The high concentration of butanol in line 1216 facilitates the recovery of butanol with a substantial saving in energy costs.

A butanol-saturated aqueous phase is returned via line 1218 from decanter 1214 to second bioreactor 1208 and contains about 7 to 8 volume percent butanol and unreacted sugars, ethanol and acetone. A purge is removed via line 1220 to maintain steady-state conditions. This stream can be used for product recovery to obtain ethanol, acetone and butanol. Second bioreactor 1208 can be operated such that with the recycle rate of the aqueous medium, only a portion of the sugar is bioconverted, but that converted to butanol goes to a butanol phase for recovery. If required, additional water and nutrients can be provided to first bioreactor 1204 via line 1222.

The bioreactor assembly, while described in connection with making n-butanol, is useful for the bioconversion of substrates where the bioconversion activity of the biocatalyst decreases with increased bioproduct concentration in the aqueous medium and where the bioproduct can form a separate liquid phase. In its broad aspects, these continuous processes for the bioconversion of substrate to bioproduct using a microorganism capable of such bioconversion wherein the bioproduct is toxic to the microorganism comprise:

a. continuously supplying substrate and aqueous medium to at least one first bioreactor containing aqueous medium, said at least one first bioreactor having therein biocatalyst of this invention comprising said microorganism;

b. maintaining said at least one first bioreactor under metabolic conditions and continuously withdrawing a first reactor effluent from said at least one first bioreactor at a rate sufficient to maintain steady-state conditions and provide a hydraulic residence time sufficient to bioconvert a portion of the substrate, said a first bioreactor effluent containing unconsumed substrate and bioproduct, wherein the bioconversion activity to said bioproduct in said at least one first bioreactor is at a first rate;

c. continuously supplying the withdrawn first bioreactor effluent to at least one subsequent bioreactor containing aqueous medium, said at least one subsequent bioreactor having therein biocatalyst of this invention comprising said microorganism;

d. maintaining said at least one subsequent bioreactor under metabolic conditions and continuously withdrawing a subsequent bioreactor effluent from said at least one subsequent bioreactor at a rate sufficient to maintain steady-state conditions and provide a hydraulic residence time sufficient to bioconvert at least a portion of the substrate, said a subsequent bioreactor effluent containing bioproduct, wherein the bioconversion activity to said bioproduct in said at least one subsequent bioreactor is at a second rate which is lower than the first rate;

e. continuously separating a bioproduct-rich stream from said withdrawn subsequent bioreactor effluent for product recovery and provide a residual aqueous stream; and f. continuously recycling at least a portion of the residual aqueous stream to at least one subsequent bioreactor.

In many instances the subsequent bioreactor effluent contains substrate. In preferred aspects of this process, the at least one subsequent bioreactor comprises a fluidized bed bioreactor. The separation of step (e) may be by any suitable separation technique, including but not limited to, Typical Separation Techniques. In preferred aspects, the bioproduct is capable of forming a separate liquid phase in the aqueous medium and at least in the at least one subsequent bioreactor, the concentration of the bioproduct forms a separate liquid phase and the subsequent bioreactor effluent is subjected to phase separation to provide a bioproduct-containing phase and the residual aqueous phase. In some preferred aspects, especially where the bioproduct forms a separate liquid phase, the subsequent bioreactor effluent and the recycle of the residual aqueous stream are at rates sufficient to maintain a desired second rate of bioconversion activity and form the second liquid phase. Often, only a portion of the substrate is bioconverted in said at least one subsequent bioreactor, and a sufficient concentration of substrate is maintained in the aqueous medium in the at least one subsequent bioreactor to enhance the rate of conversion of substrate to bioproduct.

Examples 225 to 231

A series of seven batch fermentation experiments are conducted using the following general procedure. In each experiment, a biocatalyst substantially as described in Example 93 is used which has a nominal diameter of about 4 millimeters and is maintained under an anaerobic environment of nitrogen. A batch medium is prepared in accordance with ATCC® Medium 2107, a modified reinforced Clostridial agar/broth medium, as follows:

Combine 38 grams of reinforced clostridial medium BD 218081 (ATCC, Manassas, Va.); 14.5 g of agar and 1000 milliliters of deionized water and boil to dissolve the agar, Separately prepare a solution of 10 grams of peptone, 10 grams of beef extract, 3 grams of yeast extract, 5 grams of dextrose, 5 grams of sodium chloride, 1 gram of soluble starch, 0.5 gram of L-cysteine hydrochloride, 3 grams of sodium acetate and 4 milliliters of Resazurin (0.025%) in 1000 milliliters of deionized water, and Combine the solutions.

Glucose is added to the combined solution at either 60 or 120 grams per liter, and the solution is adjusted to a pH of about 5.5 with 5N sodium hydroxide. The batch medium is then made anaerobic by autoclaving at 121° C. for 20 minutes while sparging with nitrogen that had been passed through a 0.2 micron filer. Each batch fermentation is conducted in a sealed tank reactor and about 2 milliliters of the batch medium is used per gram of biocatalyst. Into some of the reactors, n-butanol is injected to determine the effect of n-butanol on the biocatalysts and the fermentation. The fermentations are conducted at a temperature of about 37° C., and samples of the fermentation broth are taken periodically and analyzed by gas chromatography. The fermentations continue for 48 hours. The data are summarized in Table VI.

TABLE VI

| Example | Glucose added, g/L | n-Butanol added, vol % | Comments |
| --- | --- | --- | --- |
| 225 | 120 | 0 | Butanol being produced |
| 226 | 120 | 2 | Butanol being produced |
| 227 | 120 | 5 | Butanol being produced |
| 228 | 120 | 10 | Butanol being produced at reduced rate, two phases in broth |
| 229 | 60 | 10 | Butanol being produced at reduced rate, two phases in broth |
| 230 | 120 | 15 | Butanol being produced at reduced rate, two phases in broth |
| 231 | 120 | 22 | Butanol being produced at reduced rate, two phases in broth | xii. Ethanol

The biocatalyst of this invention is attractive for the conversion of substrate to ethanol. The maximum titer of ethanol in fermentation broths using yeasts is typically about 15 to 18 percent, and the conversion efficiency of substrate such as sugars and syngas to ethanol in commercial processes using yeasts is typically less than about 95 percent of theoretical. With other ethanol-producing microorganisms such as cyanobacteria and *Clostridia*, their sensitivity to ethanol concentrations may be much greater than those of yeasts. For instance, it has been reported that 1.5 volume percent ethanol causes a 50 percent growth decrease in *Synechocystis* sp. PCC 6803. Hence, processes using these alternative microorganisms generate very dilute ethanol-containing broths. U.S. Pat. No. 7,682,821 B2 discloses a closed photobioreactor using daily ambient temperature swings as a means to reduce the cost of ethanol separation. The processes using the biocatalyst of this invention permit higher titers of ethanol to be produced thereby reducing costs of the water/ethanol separation, and the conversion efficiency approaches nearly the theoretical efficiency due to the phenotypic changes to the microorganism in the biocatalysts of this invention.

In the broad aspects, the processes for bioconverting substrate to ethanol comprise:
a. contacting an aqueous medium with a biocatalyst of this invention, said biocatalyst containing microorganisms capable of bioconverting said substrate to ethanol, wherein said aqueous medium is maintained under metabolic conditions including the presence of nutrients for said microorganisms and contains said substrate;
b. maintaining the contact between the aqueous medium and biocatalyst for a time sufficient to bioconvert at least a portion of said substrate to ethanol; and
c. recovering ethanol from said aqueous medium.

The microorganism to be used will define the substrate. Substrates that have found application in producing ethanol include carbon dioxide, sugars and syngas. Microorganisms capable to producing ethanol included, but are not limited to, wild-type or recombinant bacteria and yeasts, e.g., *Clostridia*, such as *C. ljungdahlii*, *Clostridium aceticum*, and *C. thermoaceticum*, *Acetogenium kivui*, *Acetobacterium woodii*, *Acetoanaerobium noterae*, *Butyribacterium methylotrophicum*, *Eubacterium limosum*, *Zymomonas mobilis*, *Zymomonas palmae*, mesophilic yeasts such as *Pichia stipitis*, *Pichia segobiensis*, *Candida shehatae*, *Candida tropicalis*, *Candida boidinii*, *Candida tenuis*, *Pachysolen tannophilus*, *Hansenula polymorpha*, *Candida famata*, *Candida parapsilosis*, *Candida rugosa*, *Candica sonorensis*, *Issatchenkia terricola*, *Kloeckera apis*, *Pichia barkeri*, *Pichia cactophila*, *Pichia deserticola*, *Pichia norvegensis*, *Pichia membranefaciens*, *Pichia mexicana*, *Sacchrimyces cervisea* and *Torulaspora delbrueckii* and thermophilic yeasts such as *Candida bovina*, *Candida picachoensis*, *Candida emberorum*, *Candida pintolopesii*, *Candida thermophila*, *Kluyveromyces marxianus*, *Kluyveromyces fragilis*, *Kazachstania telluris*, *Issatchenkia orientalis* and *Lachancea thermotolerans*. Thermophylic bacteria include, among others, *Clostridium thermocellum*, *Clostridium thermohydrosulphuricum*, *Clostridium thermosaccharolyticum*, *Thermoanaerobium brockii*, *Thermobacteroides acetoethylicus*, *Thermoanaerobacter ethanolicus*, *Clostridium thermoaceticum*, *Clostridium thermoautotrophicum*, *Acetogenium kivui*, *Desulfotomaculum nigrificans* and *Desulvovibrio thermophilus*, *Thermoanaerobacter tengcongensis*, *Bacillus stearothermophilus* and *Thermoanaerobacter mathranii*. Genetically enhanced photoautotrophic cyanobacteria, algae, and other photoautotrophic organisms have been adapted to bioconvert carbohydrates internal to the microorganism to ethanol. For example, genetically modified cyanobacteria having constructs comprising DNA fragments encoding pyruvate decarboxylase (pdc) and alcohol dehydrogenase (adh) enzymes are described in U.S. Pat. No. 6,699,696. cyanobacteria are photosynthetic bacteria which require light, inorganic elements, water, and a carbon source, generally carbon dioxide, to metabolize and grow. The production of ethanol using genetically engineered cyanobacteria has also been described in PCT Published Patent Application WO 2007/084477. See also United States published patent application no. 20120301937 for a listing of ethanol-producing microorganisms.

Bioconversion conditions are often within Typical Mesophilic Bioconversion Conditions, and Typical Bioreactor Systems can be used. Continuous processes are preferred especially since the biocatalysts of this invention can provide high cell densities and thus, together with the enhanced bioconversion rate, provide for high conversion efficiencies of substrate with relatively brief average residence times in the bioreactor, e.g., often less than about 3 or 4 hours, and sometimes less than about 30 minutes.

For photosynthetic processes, the combination of high concentrations of cells per unit volume of liquid culture medium, the essential absence of debris from the microorganisms thus providing a clearer culture medium and the phenotypic changes associated with the biocatalysts of this invention, enables a significant increase in ethanol that can be generated per unit time per unit surface area. Hence, smaller footprints are required for the photobioreactors, and the closed processes such as disclosed in U.S. Pat. No. 7,682,821 can generated even higher concentrations of ethanol in the condensate. Additionally, since in situ sterilization can be used, more reliable operations can occur as the population of any contaminating microorganisms can be controlled. The photobioreactor can contain a liquid culture medium with the biocatalysts therein. The substrate, e.g., carbon dioxide, can be dissolved in the culture medium, or the biocatalyst can be contacted with gaseous substrate and then ethanol can be removed from the biocatalyst, for instance, by evaporation or by contact with an extractant for ethanol such as water.

Example 232

A fluidized bed bioreactor is charged to about 75 volume percent of its capacity with biocatalyst substantially as described in example 147. A continuous flow of water containing glucose at a concentration of either 120 grams per liter or 250 grams per liter is provided to the bioreactor at various rates to provide hydraulic residence times of either 4 or 10 hours. The bioreactor is maintained at a temperature of about 37° C. The effluent from the bioreactor is periodically analyzed for ethanol and glucose concentrations. At the 4 hour hydraulic retention time, the conversion of sugars yields about 95 to 97 percent of theoretical ethanol production at each glucose concentration. At the 10 hour hydraulic retention time, the conversion of sugars yields about 98 to 99 percent of theoretical ethanol production at each glucose concentration.

xiii. Anaerobic Digestion

As discussed above, municipal wastewater is often subjected to an aerobic bioconversion. Supplying oxygen to the bioreactor is a significant expense, even is air is used as the oxygen-containing gas, to the municipal wastewater facility and often is at least about 30 percent of the overall costs. Moreover, where tertiary treatment is required, an anaerobic bioconversion is used, and thus the oxygen concentration in the water being treated must be lowered. To meet regulatory requirements established in a number of jurisdictions, the wastewater treatment must reduce the organic content as well as reduce or substantially eliminate pathogens.

Mesophilic anaerobic digestion has been proposed. While eliminating the costs of oxygen supply, such processes suffer from a number of drawbacks. Maintaining effective populations of microorganisms has proven difficult, especially since both acidogenesis and methanogenesis must be supported. The residence time is long, often in the range of 15 days, and the process often does not provide sufficient reduction of pathogens.

Thermophilic anaerobic digestion does provide an advantage of a shorter residence time and a better ability to treat pathogens. See, for instance, United States published patent application no. 2013010539. Maintaining the population of microorganisms still remains problematic, and the wastewater must be brought up to and maintained at a temperature of at least 45° C. for operation of the thermophilic microorganisms.

The biocatalysts of this invention provide for improvements in the anaerobic digestion of wastewater in that not only can the thermophilic microorganisms be targeted for the biocatalyst as opposed to conventional systems where the microorganisms are often derived from the sludge, but also the biocatalyst can provide a high concentration of the thermophilic microorganisms per unit of bioreactor volume. The rate of bioconversion, and thus the hydraulic residence time, can be reduced. More importantly, since the thermophilic anaerobic bioconversion is exothermic, the high concentration of microorganisms effectively serves as a heat source to obtain and maintain thermophilic bioconversion temperatures. Also, as the thermophiles are in the biocatalyst of this invention, the processes are useful even for treating waste water having a low organic content.

The processes for thermophilic anaerobic digestion of wastewater containing organic compound comprise:

a. contacting under thermophilic conditions said wastewater with biocatalyst of this invention containing thermophilic microorganisms suitable for the bioconversion of organic compounds to methane, preferably said thermophilic conditions comprise a temperature of at least about 45° C., say, between about 47° C. and 65° C. or 70° C., for a time sufficient to reduce the concentration of organic compound, preferably to a BOD of less than about 10, preferably less than about 4, milligrams of oxygen per liter, to provide a treated water and a biogas, b. separating the biogas from the wastewater and c. separating the treated water from the biocatalyst.

Preferably the microorganism used in the biocatalyst comprises a methanogen, especially one or more of the following microorganisms *Methanosarcina acetivorans, Methanothermobacter thermautotrophicus, Methanobrevibacter smithii, Methanospirillum hungatei, Candidatus Brocadia anammoxidans, Kuenenia* sp., *Anammoxoglobus* sp., *Jettenia* sp., and *Scalindua* sp. The cell concentration in the biocatalyst is preferably at least about 100 or 200 grams per liter. Usually the bioconversion conditions include maintaining a pH in the range of about 6.5 to 9, say, about 7 to 8.5. Often the oxygen concentration in the wastewater to be contacted with the biocatalyst is less than about 2 milligrams per liter. Any suitable bioreactor configuration can be used including, but not limited to, Typical Bioreactor Systems. Preferably the bioreactor contains sufficient biocatalyst to provide at least about 100 grams of cells per liter of capacity.

xiv. Other Applications

The properties of the biocatalysts of this invention enable a wide range of specific applications. For instance, the ability to achieve a high population of microorganisms with a stable population make the biocatalysts of this invention useful for biological detection devices; coatings including but not limited to, antifouling paint and coatings such as for ship hulls and other surfaces immersed in surface water; and filters to remove undesirable components from gases and liquids. The biocatalysts can be used in biological fuel cells.

The biocatalysts of this invention can be used for producing hydrogen or hydrogen equivalents using mesophilic or thermophilic, anaerobic or facultative anaerobic microorganisms. The hydrogen can be recovered or used in another chemical or metabolic process. In one such process, methane can be used to produce hydrogen and then the hydrogen used to reduce sulfate to sulfide using sulfate-reducing microorganisms. Since the microorganisms are irreversibly retained in the biocatalysts, co-cultures, either in the same or different biocatalysts, can be maintained.

The biocatalysts of this invention can find application in methanogenesis of carbonaceous substrates especially to methane. The microorganisms having this bioactivity are typically syntrophs, and the biocatalyst enhances the stability of the syntrophic system.

The biocatalysts of this invention can be used to produce alkenes such as ethylene, propylene, butene, butadiene and styrene from, e.g., carbohydrates such as sugars, syngas, and carbon dioxide. See, for instance, United States published patent application 20130122563.

The biocatalysts of this invention can be used for treatment of various ground, surface, municipal wastewater and industrial water streams as set forth above. Additionally, beneficial applications include anaerobic digestion, removal of sulfate and sulfite anions, and as a layered catalyst for conducting aerobic wastewater treatment.

APPENDIX A

Representative microorganisms include, without limitation, *Acetobacter* sp., *Acetobacter aceti*, *Achromobacter*, *Acidiphilium*, *Acidovorax delafieldi* P4-1, *Acinetobacter* sp. (*A. calcoaceticus*), *Actinomadura*, *Actinoplanes*, *Actinomycetes*, *Aeropyrum pernix*, *Agrobacterium* sp., *Alcaligenes* sp. (*A. dentrificans*), *Alloiococcus otitis*, *Ancylobacter aquaticus*, *Ananas comosus* (M), *Arthrobacter* sp., *Arthrobacter sulfurous*, *Arthrobacter* sp. (*A. protophormiae*), *Aspergillus* sp., *Aspergillus niger*, *Aspergillus oryze*, *Aspergillus melleus*, *Aspergillus pulverulentus*, *Aspergillus saitoi*, *Aspergillus sojea*, *Aspergillus usamii*, *Bacillus alcalophilus*, *Bacillus amyloliquefaciens*, *Bacillus brevis*, *Bacillus circulans*, *Bacillus clausii*, *Bacillus cereus*, *Bacillus lentus*, *Bacillus licheniformis*, *Bacillus macerans*, *Bacillus stearothermophilus*, *Bacillus subtilis*, *Beijerinckia* sp., *Bifidobacterium*, *Brevibacterium* sp. HL4, *Brettanomyces* sp., *Brevibacillus brevis*, *Burkholderia cepacia*, *Campylobacter jejuni*, *Candida* sp., *Candida cylindracea*, *Candida rugosa*, *Carboxydothermus* (*Carboxydothermus hydrogenoformans*), *Carica papaya* (L), *Cellulosimicrobium*, *Cephalosporium*, *Chaetomium erraticum*, *Chaetomium gracile*, *Chlorella* sp., *Citrobacter*, *Clostridium* sp., *Clostridium butyricum*, *Clostridium acetobutylicum*, *Clostridium kluyveri*, *Clostridium carboxidivorans*, *Clostridium thermocellum*, *Cornynebacterium* sp. strain m15, *Corynebacterium* (*glutamicum*), *Corynebacterium efficiens*, *Deinococcus radiophilus*, *Dekkera*, *Dekkera bruxellensis*, *Escherichia coli*, *Enterobacter* sp., *Enterococcus*, *Enterococcus faecium*, *Enterococcus gallinarium*, *Enterococcus faecalis*, *Erwinia* sp., *Erwinia chrysanthemi*, *Gliconobacter*, *Gluconacetobacter* sp., *Hansenula* sp., *Haloarcula*, *Humicola insolens*, *Humicola nsolens*, *Kitasatospora setae*, *Klebsiella* sp., *Klebsiella oxytoca*, *Klebsiella pneumonia*, *Kluyveromyces* sp., *Kluyveromyces fragilis*, *Kluyveromyces lactis*, *Kocuria*, *Lactlactis*, *Lactobacillus* sp., *Lactobacillus fermentum*, *Lactobacillus sake*, *Lactococcus*, *Lactococcus lactis*, *Leuconostoc*, *Methylosinus trichosporum* OB3b, *Methylosporovibrio methanica* 812, *Methanothrix* sp. *Methanosarcina* sp., *Methanomonas* sp., *Methylocystis*, *Methanospirilium*, *Methanolobus siciliae*, *Methanogenium organophilum*, *Methanobacerium* sp., *Methanobacterium bryantii*, *Methanococcus* sp., *Methanomicrobium* sp., *Methanoplanus* sp., *Methanosphaera* sp., *Methanolobus* sp., *Methanoculleus* sp., *Methanosaeta* sp., *Methanopyrus* sp., *Methanocorpusculum* sp., *Methanosarcina*, *Methylococcus* sp., *Methylomonas* sp., *Methylosinus* sp., *Microbacterium imperiale*, *Micrococcus* sp., *Micrococcus lysodeikticus*, *Microlunatus*, *Moorella* (e.g., *Moorella* (*Clostridium*) *thermoacetica*), *Moraxella* sp. (strain B), *Morganella*, *Mucor javanicus*, *Mycobacterium* sp. strain GP1, *Myrothecium*, *Neptunomonas naphthovorans*, *Nitrobacter*, *Nitrosomonas* (*Nitrosomonas europea*), *Nitzchia* sp., *Nocardia* sp., *Pachysolen* sp., *Pantoea*, *Papaya carica*, *Pediococcus* sp., *Pediococcus halophilus*, *Penicillium*, *Penicillium camemberti*, *Penicillium citrinum*, *Penicillium emersonii*, *Penicillium roqueforti*, *Penicillum lilactinum*, *Penicillum multicolor*, *Phanerochaete chrysoporium*, *Pichia* sp., *Pichia stipitis*, *Paracoccus pantotrophus*, *Pleurotus ostreatus*, *Propionibacterium* sp., *Proteus*, *Pseudomonas* (*P. pavonaceae*, *Pseudomonas* ADP, *P. stutzeri*, *P. putida*, *Pseudomonas* Strain PS1, *P. cepacia* G4, *P. medocina* KR, *P. picketti* PK01, *P. vesicularis*, *P. paucimobilis*, *Pseudomonas* sp. DLC-P11, *P. mendocina*, *P. chichhori*, strain IST 103), *Pseudomonas fluorescens*, *Pseudomonas denitrificans*, *Pyrococcus*, *Pyrococcus furiosus*, *Pyrococcus horikoshii*, *Ralstonia* sp., *Rhizobium*, *Rhizomucor miehei*, *Rhizomucor pusillus* Lindt, *Rhizopus*, *Rhizopus delemar*, *Rhizopus japonicus*, *Rhizopus niveus*, *Rhizopus oryzae*, *Rhizopus oligosporus*, *Rhodococcus*, (*R. erythropolis*, *R. rhodochrous* NCIMB 13064), *Salmonella*, *Saccharomyces* sp., *Saccharomyces cerevisiae*, *Schizochytriu* sp., *Sclerotina libertina*, *Serratia* sp., *Shigella*, *Sphingobacterium multivorum*, *Sphingobium* (*Sphingbium chlorophenolicum*), *Sphingomonas* (*S. yanoikuyae*, S. sp. RW1), *Streptococcus*, *Streptococcus thermophilus* Y-I, *Streptomyces*, *Streptomyces griseus*, *Streptomyces lividans*, *Streptomyces murinus*, *Streptomyces rubiginosus*, *Streptomyces violaceoruber*, *Streptoverticillium mobaraense*, *Synechococcus* sp., *Synechocystis* sp., *Tetragenococcus*, *Thermus*, *Thiosphaera pantotropha*, *Trametes*, *Trametes versicolor*, *Trichoderma*, *Trichoderma longibrachiatum*, *Trichoderma reesei*, *Trichoderma viride*, *Trichosporon* sp., *Trichosporon penicillatum*, *Vibrio alginolyticus*, *Xanthomonas*, *Xanthobacter* sp. (*X. autotrophicus* GJ10, X *flavus*), yeast, *Yarrow lipolytica*, *Zygosaccharomyces rouxii*, *Zymomonas* sp., *Zymomonus mobilis*, *Geobacter sulfurreducens*, *Geobacter lovleyi*, *Geobacter metallireducens*, *Bacteroides succinogens*, *Butyrivibrio fibrisolvens*, *Clostridium cellobioparum*, *Ruminococcus albus*, *Ruminococcus flavefaciens*, *Eubacterium cellulosolvens*, *Clostridium cellulosolvens*, *Clostridium cellulovorans*, *Clostridium thermocellum*, *Bacteroides cellulosolvens*, and *Acetivibrio cellulolyticus* *Gliricidia* sp., *Albizia* sp., or *Parthenium* sp. *Cupriavidus basilensis*, *Cupriavidus campinensis*, *Cupriavidus gilardi*, *Cupriavidus laharsis*, *Cupriavidus metallidurans*, *Cupriavidus oxalaticus*, *Cupriavidus pauculus*, *Cupriavidus pinatubonensis*, *Cupriavidus respiraculi*, *Cupriavidus taiwanensis*, *Oligotropha carboxidovorans*, *Thiobacillus* sp., *Thiobacillus denitrificans*, *Thiobacillus thioxidans*, *Thiobacillus ferrooxidans*, *Thiobacillus concretivorus*, *Acidithiobacillus albertensis*, *Acidithiobacillus caldus*, *Acidithiobacillus cuprithermicus*, *Rhodopseudomonas*, *Rhodopseudomonas* palustris, Rhodobacter sphaeroides, Rhodopseudomonas capsulate, Rhodopseudomonas acidophila, Rhodopseudomonas viridis, Desulfotomaculum, Desulfotomaculum acetoxidans, Desulfotomaculum kuznetsovii, Desulfotomaculum nigrificans, Desulfotomaculum reducens, Desulfotomaculum carboxydivorans, Methanosarcina barkeri, Methanosarcina acetivorans, Moorella thermoacetica, Carboxydothermus hydrogenoformans, Rhodospirillum rubrum, Acetobacterium woodii, Butyribacterium methylotrophicum, Clostridium autoethanogenum, Clostridium ljungdahlii, Eubacterium limosum, Oxobacter pfennigii, Peptostreptococcus productus, Rhodopseudomonas palustris P4, Rubrivivax gelatinosus, Citrobacter sp Y19, Methanosarcina acetivorans C2A, Methanosarcina barkeri, Desulfosporosinus orientis, Desulfovibrio desulfuricans, Desulfovibrio vulgaris, Moorella thermoautotrophica, Carboxydibrachium pacificus, Carboxydocella thermoautotrophica, Thermincola carboxydiphila, Thermolithobacter carboxydivorans, Thermosinus carboxydivorans, Methanothermobacter thermoautotrophicus, Desulfotomaculum carboxydivorans, Desulfotomaculum kuznetsovii, Desulfotomaculum nigrificans, Desulfotomaculum thermobenzoicum subsp. thermosyntrophicum, Syntrophobacter fumaroxidans, Clostridium acidurici, Desulfovibrio africanus, C. pasteurianum, C. pasteurianum DSM 525, Paenibacillus polymyxa, Acanthoceras, Acanthococcus, Acaryochloris, Achnanthes, Achnanthidium, Actinastrum, Actinochloris, Actinocyclus, Actinotaenium, Amphichrysis, Amphidinium, Amphikrikos, Amphipleura, Amphiprora, Amphithrix, Amphora, Anabaena, Anabaenopsis, Aneumastus, Ankistrodesmus, Ankyra, Anomoeoneis, Apatococcus, Aphanizomenon, Aphanocapsa, Aphanochaete, Aphanothece, Apiocystis, Apistonema, Arthrodesmus, Artherospira, Ascochloris, Asterionella, Asterococcus, Audouinella, Aulacoseira, Bacillaria, Balbiania, Bambusina, Bangia, Basichlamys, Batrachospermum, Binuclearia, Bitrichia, Blidingia, Botrdiopsis, Botrydium, Botryococcus, Botryosphaerella, Brachiomonas, Brachysira, Brachytrichia, Brebissonia, Bulbochaete, Bumilleria, Bumilleriopsis, Caloneis, Calothrix, Campylodiscus, Capsosiphon, Carteria, Catena, Cavinula, Centritractus, Centronella, Ceratium, Chaetoceros, Chaetochloris, Chaetomorpha, Chaetonella, Chaetonema, Chaetopeltis, Chaetophora, Chaetosphaeridium, Chamaesiphon, Chara, Characiochloris, Characiopsis, Characium, Charales, Chilomonas, Chlainomonas, Chlamydoblepharis, Chlamydocapsa, Chlamydomonas, Chlamydomonopsis, Chlamydomyxa, Chlamydonephris, Chlorangiella, Chlorangiopsis, Chlorella, Chlorobotrys, Chlorobrachis, Chlorochytrium, Chlorococcum, Chlorogloea, Chlorogloeopsis, Chlorogonium, Chlorolobion, Chloromonas, Chlorophysema, Chlorophyta, Chlorosaccus, Chlorosarcina, Choricystis, Chromophyton, Chromulina, Chroococcidiopsis, Chroococcus, Chroodactylon, Chroomonas, Chroothece, Chrysamoeba, Chrysapsis, Chrysidiastrum, Chrysocapsa, Chrysocapsella, Chrysochaete, Chrysochromulina, Chrysococcus, Chrysocrinus, Chrysolepidomonas, Chrysolykos, Chrysonebula, Chrysophyta, Chrysopyxis, Chrysosaccus, Chrysophaerella, Chrysostephanosphaera, Clodophora, Clastidium, Closteriopsis, Closterium, Coccomyxa, Cocconeis, Coelastrella, Coelastrum, Coelosphaerium, Coenochloris, Coenococcus, Coenocystis, Colacium, Coleochaete, Collodictyon, Compsogonopsis, Compsopogon, Conjugatophyta, Conochaete, Coronastrum, Cosmarium, Cosmioneis, Cosmocladium, Crateriportula, Craticula, Crinalium, Crucigenia, Crucigeniella, Cryptoaulax, Cryptomonas, Cryptophyta, Ctenophora, Cyanodictyon, Cyanonephron, Cyanophora, Cyanophyta, Cyanothece, Cyanothomonas, Cyclonexis, Cyclostephanos, Cyclotella, Cylindrocapsa, Cylindrocystis, Cylindrospermum, Cylindrotheca, Cymatopleura, Cymbella, Cymbellonitzschia, Cystodinium Dactylococcopsis, Debarya, Denticula, Dermatochrysis, Dermocarpa, Dermocarpella, Desmatractum, Desmidium, Desmococcus, Desmonema, Desmosiphon, Diacanthos, Diacronema, Diadesmis, Diatoma, Diatomella, Dicellula, Dichothrix, Dichotomococcus, Dicranochaete, Dictyochloris, Dictyococcus, Dictyosphaerium, Didymocystis, Didymogenes, Didymosphenia, Dilabifilum, Dimorphococcus, Dinobryon, Dinococcus, Diplochloris, Diploneis, Diplostauron, Distrionella, Docidium, Draparnaldia, Dunaliella, Dysmorphococcus, Ecballocystis, Elakatothrix, Ellerbeckia, Encyonema, Enteromorpha, Entocladia, Entomoneis, Entophysalis, Epichrysis, Epipyxis, Epithemia, Eremosphaera, Euastropsis, Euastrum, Eucapsis, Eucoccneis, Eudorina, Euglena, Euglenophyta, Eunotia, Eustigmatophyta, Eutreptia, Fallacia, Fischerella, Fragilaria, Fragilariforma, Franceia, Frustulia, Curcilla, Geminella, Genicularia, Glaucocystis, Glaucophyta, Glenodiniopsis, Glenodinium, Gloeocapsa, Gloeochaete, Gloeochrysis, Gloeococcus, Gloeocystis, Gloeodendron, Gloeomonas, Gloeoplax, Gloeothece, Gloeotila, Gloeotrichia, Gloiodictyon, Golenkinia, Golenkiniopsis, Gomontia, Gomphocymbella, Gomphonema, Gomphosphaeria, Gonatozygon, Gongrosia, Gongrosira, Goniochloris, Gonium, Gonyostomum, Granulochloris, Granulocystopsis, Groenbladia, Gymnodinium, Gymnozyga, Gyrosigma, Haematococcus, Hafniomonas, Hallassia, Hammatoidea, Hannaea, Hantzschia, Hapalosiphon, Haplotaenium, Haptophyta, Haslea, Hemidinium, Hemitoma, Heribaudiella, Heteromastix, Heterothrix, Hibberdia, Hildenbrandia, Hillea, Holopedium, Homoeothrix, Hormanthonema, Hormotila, Hyalobrachion, Hyalocardium, Hyalodiscus, Hyalogonium, Hyalotheca, Hydrianum, Hydrococcus, Hydrocoleum, Hydrocoryne, Hydrodictyon, Hydrosera, Hydrurus, Hyella, Hymenomonas, Isthmochloron, Johannesbaptistia, Juranyiella, Karayevia, Kathablepharis, Katodinium, Kephyrion, Keratococcus, Kirchneriella, Klebsormidium, Kolbesia, Koliella, Komarekia, Korshikoviella, Kraskella, Lagerheimia, Lagynion, Lamprothamnium, Lemanea, Lepocinclis, Leptosira, Lobococcus, Lobocystis, Lobomonas, Luticola, Lyngbya, Malleochloris, Mallomonas, Mantoniella, Marssoniella, Martyana, Mastigocoleus, Gastogloia, Melosira, Merismopedia, Mesostigma, Mesotaenium, Micractinium, Micrasterias, Microchaete, Microcoleus, Microcystis, Microglena, Micromonas, Microspora, Microthamnion, Mischococcus, Monochrysis, Monodus, Monomastix, Monoraphidium, Monostroma, Mougeotia, Mougeotiopsis, Myochloris, Myromecia, Myxosarcina, Naegeliella, Nannochloris, Nautococcus, Navicula, Neglectella, Neidium, Nephroclamys, Nephrocytium, Nephrodiella, Nephroselmis, Netrium, Nitella, Nitellopsis, Nitzschia, Nodularia, Nostoc, Ochromonas, Oedogonium, Oligochaetophora, Onychonema, Oocardium, Oocystis, Opephora, Ophiocytium, Orthoseira, Oscillatoria, Oxyneis, Pachycladella, Palmella, Palmodictyon, Pnadorina, Pannus, Paralia, Pascherina, Paulschulzia, Pediastrum, Pedinella, Pedinomonas, Pedinopera, Pelagodictyon, Penium, Peranema, Peridiniopsis, Peridinium, Peronia, Petroneis, Phacotus, Phacus, Phaeaster, Phaeodermatium, Phaeophyta, Phaeosphaera, Phaeothamnion, Phormidium, Phycopeltis, Phyllariochloris, Phyllocardium, Phyllomitas, Pinnularia, Pitophora, Placoneis, Planctonema, Planktosphaeria, Planothidium, Plectonema, Pleodorina, Pleurastrum, Pleurocapsa, Pleurocladia, Pleurodiscus, Pleurosigma, Pleurosira, Pleurotaenium, Pocillomonas, Podohedra, Polyblepharides, Polychaeto-

*phora, Polyedriella, Polyedriopsis, Polygoniochloris, Polyepidomonas, Polytaenia, Polytoma, Polytomella, Porphyridium, Posteriochromonas, Prasinochloris, Prasinocladus, Prasinophyta, Prasiola, Prochlorphyta, Prochlorothrix, Protoderma, Protosiphon, Provasoliella, Prymnesium, Psammodictyon, Psammothidium, Pseudanabaena, Pseudenoclonium, Psuedocarteria, Pseudochate, Pseudocharacium, Pseudococcomyxa, Pseudodictyosphaerium, Pseudokephyrion, Pseudoncobyrsa, Pseudoquadrigula, Pseudosphaerocystis, Pseudostaurastrum, Pseudostaurosira, Pseudotetrastrum, Pteromonas, Punctastruata, Pyramichlamys, Pyramimonas, Pyrrophyta, Quadrichloris, Quadricoccus, Quadrigula, Radiococcus, Radiofilum, Raphidiopsis, Raphidocelis, Raphidonema, Raphidophyta, Peimeria, Rhabdoderma, Rhabdomonas, Rhizoclonium, Rhodomonas, Rhodophyta, Rhoicosphenia, Rhopalodia, Rivularia, Rosenvingiella, Rossithidium, Roya, Scenedesmus, Scherffelia, Schizochlamydella, Schizochlamys, Schizomeris, Schizothrix, Schroederia, Scolioneis, Scotiella, Scotiellopsis, Scourfieldia, Scytonema, Selenastrum, Selenochloris, Sellaphora, Semiorbis, Siderocelis, Diderocystopsis, Dimonsenia, Siphononema, Sirocladium, Sirogonium, Skeletonema, Sorastrum, Spermatozopsis, Sphaerellocystis, Sphaerellopsis, Sphaerodinium, Sphaeroplea, Sphaerozosma, Spiniferomonas, Spirogyra, Spirotaenia, Spirulina, Spondylomorum, Spondylosium, Sporotetras, Spumella, Staurastrum, Stauerodesmus, Stauroneis, Staurosira, Staurosirella, Stenopterobia, Stephanocostis, Stephanodiscus, Stephanoporos, Stephanosphaera, Stichococcus, Stichogloea, Stigeoclonium, Stigonema, Stipitococcus, Stokesiella, Strombomonas, Stylochrysalis, Stylodinium, Styloyxis, Stylosphaeridium, Surirella, Sykidion, Symploca, Synechococcus, Synechocystis, Synedra, Synochromonas, Synura, Tabellaria, Tabularia, Teilingia, Temnogametum, Tetmemorus, Tetrachlorella, Tetracyclus, Tetradesmus, Tetraedriella, Tetraedron, Tetraselmis, Tetraspora, Tetrastrum, Thalassiosira, Thamniochaete, Thorakochloris, Thorea, Tolypella, Tolypothrix, Trachelomonas, Trachydiscus, Trebouxia, Trentepholia, Treubaria, Tribonema, Trichodesmium, Trichodiscus, Trochiscia, Tryblionella, Ulothrix, Uroglena, Uronema, Urosolenia, Urospora, Uva, Vacuolaria, Vaucheria, Volvox, Volvulina, Westella, Woloszynskia, Xanthidium, Xanthophyta, Xenococcus, Zygnema, Zygnemopsis, Zygonium, Chloroflexus, Chloronema, Oscillochloris, Heliothrix, Herpetosiphon, Roseiflexus, Thermomicrobium, Chlorobium, Clathrochloris, Prosthecochloris, Allochromatium, Chromatium, Halochromatium, Isochromatium, Marichromatium, Rhodovulum, Thermochromatium, Thiocapsa, Thiorhodococcus, Thiocystis, Phaeospirillum, Rhodobaca, Rhodobacter, Rhodomicrobium, Rhodopila, Rhodopseudomonas, Rhodothalassium, Rhodospirillum, Rodovibrio, Roseospira, Nitrobacteraceae* sp., *Nitrobacter* sp., *Nitrospina* sp., *Nitrococcus* sp., *Nitrospira* sp., *Nitrosomonas* sp., *Nitrosococcus* sp., *Nitrosospira* sp., *Nitrosolobus* sp., *Nitrosovibrio* sp., *Thiovulum* sp., *Thiobacillus* sp., *Thiomicrospira* sp., *Thiosphaera* sp., *Thermothrix* sp., *Hydrogenobacter* sp., *Siderococcus* sp., *Aquaspirillum* sp. *Methanobacterium* sp., *Methanobrevibacter* sp., *Methanothermus* sp., *Methanococcus* sp., *Methanomicrobium* sp., *Methanospirillum* sp., *Methanogenium* sp., *Methanosarcina* sp., *Methanolobus* sp., *Methanothrix* sp., *Methanococcoides* sp., *Methanoplanus* sp., *Thermoproteus* sp., *Pyrodictium* sp., *Sulfolobus* sp., *Acidianus* sp., *Bacillus subtilis, Saccharomyces cerevisiae, Streptomyces* sp., *Ralstonia* sp., *Rhodococcus* sp., *Corynebacteria* sp., *Brevibacteria* sp., *Mycobacteria* sp., oleaginous yeast, *Arabidopsis thaliana, Panicum virgatum, Miscanthus giganteus, Zea mays* (plants), *Botryococcus braunii, Chlamydomonas reinhardtii* and *Dunaliela salina* (algae), *Synechococcus* sp PCC 7002, *Synechococcus* sp. PCC 7942, *Synechocystis* sp. PCC 6803, *Thermosynechococcus elongatus BP*-1 (cyanobacteria), *Chlorobium tepidum* (green sulfur bacteria), *Chloroflexus auranticusl, Chromatium tepidum* and *Chromatium vinosum* (purple sulfur bacteria), *Rhodospirillum rubrum, Rhodobacter capsulatus,* and *Rhodopseudomonas palusris* (purple non-sulfur bacteria).

It is claimed:

1. A process for treating water containing at least one soluble compound of metal or semi-metal comprising:
   (a) continuously introducing said water into a reaction zone containing a biocatalyst, said biocatalyst comprising a solid structure of hydrated hydrophilic polymer defining an interior structure having a plurality of interconnected major cavities having a smallest dimension of between 5 and 100 microns and wherein said biocatalyst has a Hydration Expansion Volume (HEV), which is calculated in volume percent, of 1000 or more and a population of microorganisms for reducing said at least one soluble compound of metal or semi-metal, wherein the population is irreversibly retained in the interior structure, wherein the concentration of the population of microorganisms in the interior structure is about 60 grams per liter or more based upon the volume defined by the exterior of the solid structure when fully hydrated, and wherein the microorganisms maintain their population such that the population does not decrease by more than 50 percent nor increase by more than 400 percent;
   (b) contacting the water with said biocatalyst for a time sufficient to reduce the concentration of said at least one soluble compound of metal or semi-metal in the water;
   (c) maintaining said biocatalyst under metabolic conditions sufficient to metabolically reduce the oxidation state of the metal or semi-metal of the at least one soluble compound of metal or semi-metal to form an elemental metal or a semi-metal or a precipitated compound thereof; and
   (d) withdrawing water having a reduced concentration of said at least one soluble compound of metal or semi-metal from the reaction zone.

2. The process of claim 1 wherein the HEV of the biocatalyst is at least 20,000 and the concentration of the population of microorganisms in the interior of the solid structure is at least 100 grams per liter based upon the volume defined by the exterior of the solid structure.

3. The process of claim 1 wherein the solid structure of the biocatalyst defines an external skin having pores of an average diameter of between 1 and 10 microns and wherein the pores comprise 1 to 30 percent of the surface area of the external skin.

4. The process of claim 1 wherein the major cavities of the biocatalyst are quiescent.

5. The process of claim 1 wherein the biocatalyst contains an exo-network of said population of microorganisms, wherein the microorganisms are spaced-apart in the form of individual cells or biofilms that are interconnected by an extracellular polymeric substance in the form of strands to form the exo-network.

6. The process of claim 1 wherein the biocatalyst further comprises polysaccharide.

7. The process of claim 1 wherein the biocatalyst further comprises a solid sorbent.

8. The process of claim 1 wherein the population of microorganisms irreversibly retained in the biocatalyst is a population of photosynthetic microorganisms and the biocatalyst further comprises a phosphorescent material.

9. The process of claim 1 wherein the biocatalyst further comprises at least one isolated enzyme.

10. The process of claim 1 wherein the microorganism population irreversibly retained in the biocatalyst exhibits at least one phenotypic change selected from the group consisting of metabolic shift, enhanced rate of bioconversion, enhanced toxin resistance, strain stability, and stasis capability, as compared to a planktonic population of said microorganism.

\* \* \* \* \*